(12) United States Patent
Gessner et al.

(10) Patent No.: US 8,029,919 B2
(45) Date of Patent: Oct. 4, 2011

(54) PHENOTHIAZINES, S-OXIDES, AND S,S-DIOXIDES AS WELL AS PHENOXAZINES AS EMITTERS FOR OLEDS

(75) Inventors: Thomas Gessner, Heidelberg (DE); Hans-Werner Schmidt, Bayreuth (DE); Mukundan Thelakkat, Bayreuth (DE); Markus Baete, Kulmain (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 895 days.

(21) Appl. No.: 11/720,274

(22) PCT Filed: Nov. 25, 2005

(86) PCT No.: PCT/EP2005/012647
§ 371 (c)(1),
(2), (4) Date: Feb. 22, 2008

(87) PCT Pub. No.: WO2006/056465
PCT Pub. Date: Jan. 6, 2006

(65) Prior Publication Data
US 2010/0308714 A1    Dec. 9, 2010

(30) Foreign Application Priority Data

Nov. 25, 2004 (DE) .......................... 10 2004 057 086

(51) Int. Cl.
*H01L 51/00* (2006.01)
(52) U.S. Cl. ........ 428/690; 428/917; 313/504; 313/505; 313/506; 257/40
(58) Field of Classification Search .................. 429/690, 429/917; 313/504, 505, 506; 257/40
See application file for complete search history.

(56) References Cited

U.S. PATENT DOCUMENTS

| | | | |
|---|---|---|---|
| 5,942,615 A | | 8/1999 | Kobayashi et al. |
| 2002/0034659 A1* | | 3/2002 | Nishi et al. ............ 428/690 |
| 2003/0137239 A1* | | 7/2003 | Matsuura et al. ........... 313/503 |
| 2004/0127666 A1* | | 7/2004 | Inbasekaran et al. ......... 528/8 |

FOREIGN PATENT DOCUMENTS

| | | | |
|---|---|---|---|
| DE | 198 46 767 A1 | | 4/2000 |
| DE | 101 43 249 A1 | | 3/2003 |
| DE | 10 2004 020 046 A1 | | 7/2005 |
| EP | 0 517 542 A | | 12/1992 |
| EP | 0 535 672 A2 | | 4/1993 |
| EP | 0 562 883 A2 | | 9/1993 |
| EP | 1 400 578 A1 | | 3/2004 |
| GB | 2 083 488 | | 3/1982 |
| JP | 7-109449 | | 4/1995 |
| JP | 7-120056 | | 5/1995 |
| JP | 09-310066 | * | 12/1997 |
| JP | 11-158165 | | 6/1999 |
| JP | 2000-328052 | | 11/2000 |
| JP | 2003-7466 | | 1/2003 |
| JP | 2004-75750 | | 3/2004 |
| KR | 2003-0029394 | | 4/2003 |

* cited by examiner

*Primary Examiner* — D Lawrence Tarazano
*Assistant Examiner* — Gregory Clark
(74) *Attorney, Agent, or Firm* — Oblon, Spivak, McClelland, Maier & Neustadt, L.L.P.

(57) ABSTRACT

The use of phenoxazine, phenothiazine, phenothiazine S-oxide or phenothiazine S,S-dioxide derivatives as emitter substances in organic light-emitting diodes, an organic light-emitting diode comprising a light-emitting layer, the light-emitting layer comprising at least one phenoxazine, phenothiazine, phenothiazine S-oxide or phenothiazine S,S-dioxide derivative as an emitter substance, and a light-emitting layer comprising or consisting of the aforementioned phenoxazine, phenothiazine-phenothiazine, phenothiazine S-oxide or phenothiazine S,S-dioxide derivative as an emitter substance, a hole- and exciton-blocking layer comprising or consisting of the aforementioned phenoxazine derivative, phenothiazine derivative, phenothiazine S-oxide derivative or phenothiazine S,S-dioxide derivative, and a device which comprises an inventive organic light-emitting diode. The present invention further relates to specific phenothiazine S,S-dioxide derivatives, phenothiazine S-oxide derivatives and phenothiazine derivatives and production processes thereof, and to their use in organic light-emitting diodes.

34 Claims, No Drawings

PHENOTHIAZINES, S-OXIDES, AND S,S-DIOXIDES AS WELL AS PHENOXAZINES AS EMITTERS FOR OLEDS

The present invention relates to the use of phenoxazine derivatives, phenothiazine derivatives, phenothiazine S-oxide derivatives or phenothiazine S,S-dioxide derivatives as emitter substances or hole and exciton blockers in organic light-emitting diodes, to an organic light-emitting diode comprising a light-emitting layer, the light-emitting layer comprising at least one phenoxazine derivative, phenothiazine derivative, phenothiazine S-oxide derivative or phenothiazine S,S-dioxide derivative as an emitter substance, and to a light-emitting layer comprising or consisting of the aforementioned phenoxazine derivative, phenothiazine derivative, phenothiazine S-oxide derivative or phenothiazine S,S-dioxide derivative as an emitter substance, to a hole- and exciton-blocking layer comprising or consisting of the aforementioned phenoxazine derivative, phenothiazine derivative, phenothiazine S-oxide derivative or phenothiazine S,S-dioxide derivative, and to a device which comprises an inventive organic light-emitting diode. The present invention further relates to specific phenothiazine S,S-dioxide derivatives, phenothiazine S-oxide derivatives and phenothiazine derivatives and production processes thereof, and to their use in organic light-emitting diodes.

In organic light-emitting diodes (OLEDs), the property of materials to emit light when they are excited by electrical current is utilized. OLEDs are of particular interest as an alternative to cathode ray tubes and liquid-crystal displays for the production of flat visual display units. Owing to the very compact design and the intrinsically low electricity consumption, devices comprising LEDs are suitable especially for mobile applications, for example for applications in mobile telephones, laptops, etc.

Numerous materials have been proposed which emit light on excitation by electrical current.

According to the prior art, phenoxazine and phenothiazine derivatives are used generally as charge transport materials.

For instance, EP-A 0 517 542 relates to aromatic amino compounds which are notable for good heat stability and can have units including a phenothiazine unit. These aromatic amino compounds are used as hole transport materials in OLEDs.

EP-A 0 562 883 likewise relates to hole transport materials which are used in OLEDs and which have a high heat stability. The hole transport materials used are trisphenothiazinyltriphenylamine derivatives or trisphenoxazinyltriphenylamine derivatives.

DE-A 101 43 249 relates to a process for preparing conjugated oligo- and polyphenothiazines and to their use as hole conductors in organic light-emitting diodes and field-effect transistors. The oligo- and polyphenothiazines are prepared by means of cross-coupling of functionalized phenothiazine derivatives.

EP-A 0 535 672 discloses an electrophotographic photoreceptor which comprises an organic conductive material in its photosensitive layer. Suitable organic conductive materials include compounds which have phenothiazine structural units.

U.S. Pat. No. 5,942,615 and JP-A 11-158165 relate to phenothiazine and phenoxazine derivatives, to a charge transport material which comprises these derivatives, and to an electrophotographic photoreceptor which comprises the disclosed charge transport material. The phenothiazine or phenoxazine derivatives are derivatives of the following formula:

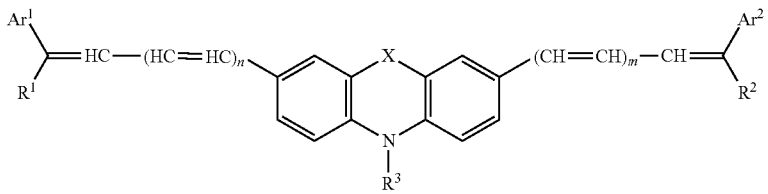

where $Ar^1$ and $Ar^2$ are each aryl groups, $R^1$ and $R^2$ are each H, lower alkyl or aryl, $R^3$ is lower alkyl, an alicyclic hydrocarbon radical having from 5 to 7 carbon atoms, aryl or aralkyl, X is S or O, and m and n are each 0 or 1. With regard to luminescence, especially electroluminescence, of the aforementioned compounds, neither U.S. Pat. No. 5,942,615 nor JP-A 11-158165 comprises any information.

The prior art discloses only a few very specific phenothiazine and phenoxazine derivatives which are used as luminescent materials in the light-emitting layer of an OLED.

JP-A 2003-007466 relates to an OLED which has a long lifetime and high illumination density which comprises, as a luminescent material, a polymer which has repeat units based on phenothiazine or phenoxazine derivatives.

JP-A 2000-328052 relates to luminescent material which emits light in the yellow to red region of the electromagnetic spectrum and is formed from a monocyclic or fused polycyclic compound which has two specific substituents. These specific substituents are substituents of the following formula:

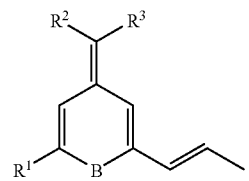

In this formula,

B is S or O, $R^1$ is H, alkyl or aryl and $R^2$ and $R^3$ are each independently selected from H, CN, halogen, alkylcarbonyl and alkoxycarbonyl; $R^2$ and $R^3$ are preferably each CN.

Phenothiazine and phenoxazine derivatives are mentioned as fused polycyclic compounds.

KR 2003-0029394 relates to red luminophores which are suitable for organic electroluminescence. These luminophors have a phenocyanidine group which has good hole transport properties, and an anthracenyl radical which has good electron transport capability. Depending on the substitution pattern of the luminophors, they may exhibit luminescence not only in the yellow and red, but also in the green region, of the electromagnetic spectrum. These specific luminophores have one of the following formulae

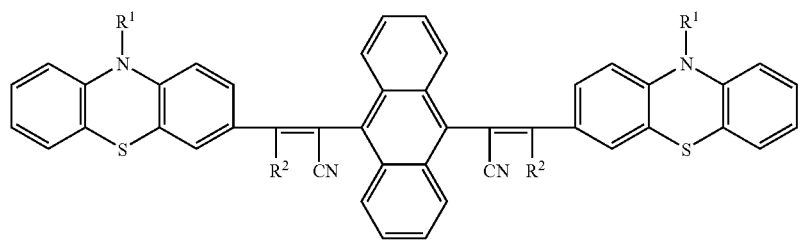

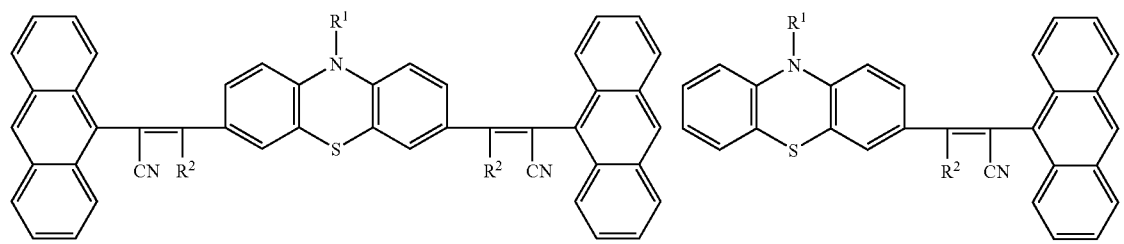

The $R^1$ and $R^2$ radicals may be H, aryl, heteroaryl, halogen or saturated or unsaturated hydrocarbons. A special feature of these compounds which is emphasized is that they have not only light emission properties, but also hole transport properties and electron transport properties, owing to their particular substitution pattern.

JP-A 2004-075750 relates to phenoxazine derivatives of the formula

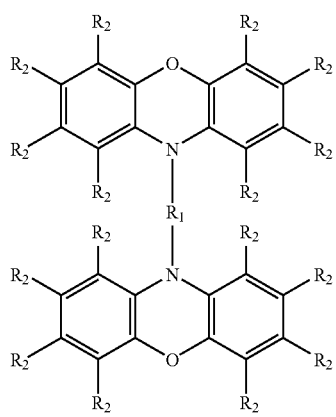

where $R_1$ is an aromatic or aliphatic joining group and $R_2$ is an alkyl, alkenyl, alkyl ether, alkoxy, amino, aryl or aryloxy group. The phenoxazine derivatives are used as fluorescent substances in the light-emitting layer of an OLED.

It is an object of the present application to provide further emitter substances, especially blue-emitting substances, for use in OLEDs, which are readily obtainable and have good illumination densities and quantum yields when used in OLEDs, and can preferably be used in substance in the light-emitting layer in OLEDs, without incorporation into a matrix material. It is a further object of the present application to provide substances which are suitable as hole and exciton blockers.

These objects are achieved by the use of compounds of the formula I

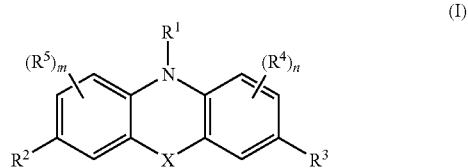

in which:
X is S, $SO_2$, O, SO, preferably S or $SO_2$, more preferably $SO_2$;
$R^1$ is H, alkyl, aryl, heteroaryl, preferably H, methyl, ethyl, unsubstituted phenyl or 4-alkoxyphenyl;
or

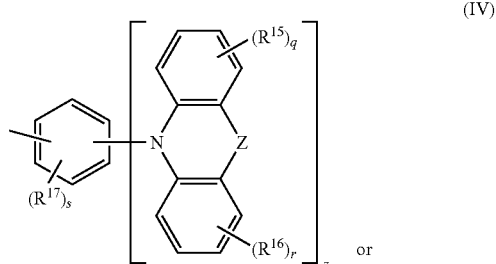

or

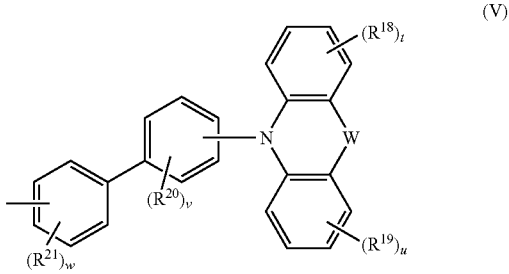

$R^2$,
$R^3$ are each independently H, alkyl, aryl, $NR^{22}R^{23}$ or $COR^{31}$, where $R^2$ and $R^3$ are not at the same time H, preferably H or aryl, more preferably H, unsubstituted phenyl, 1-naphthyl or 2-naphthyl, or
at least one of the R² or R³ radicals is a radical of the formula II

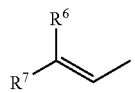
(II)

where the further R² or R³ radical has the same definition or is H, alkyl, aryl, NR²²R²³, preferably H, NR²²R²³ or aryl, most preferably H, NPh₂ or unsubstituted phenyl; the further R² or R³ radical is preferably likewise a radical of the formula II or one of the R² or R³ radicals is a radical of the formula III

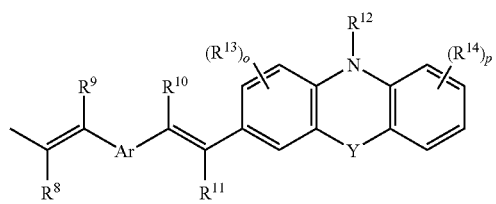
(III)

where the further R² or R³ radical is H, alkyl, aryl, NR²²R²³, preferably H, NR²²R²³ or aryl, most preferably H, NPh₂ or unsubstituted phenyl;

$R^4, R^5, R^{13}, R^{14}, R^{15}, R^{16}, R^{18}, R^{19}, R^{20}, R^{21}$
are each independently alkyl, aryl, alkenyl, alkynyl or alkylaryl, preferably alkyl or aryl;

$R^{17}$ is halogen, alkoxy, alkyl, aryl, alkenyl, alkynyl or alkylaryl, preferably fluorine, alkoxy, alkyl or aryl;

m, n are each 0, 1, 2 or 3, preferably 0 or 1, more preferably 0;

o, p, q, r, s, t, u, v, w
are each 0, 1, 2, 3 or 4, preferably 0 or 1, more preferably 0;

z is 1 or 2, preferably 1;

$R^6, R^7$
are each independently H, alkyl, aryl, alkenyl, alkynyl, alkylaryl, alkoxy, aryloxy or NR²²R²³, preferably H, alkyl or aryl, more preferably alkyl or aryl, most preferably methyl or unsubstituted phenyl;

$R^8, R^9, R^{10}, R^{11}$
are each independently H, alkyl, aryl, alkenyl, alkynyl or alkylaryl, preferably H, alkyl or aryl, more preferably H or alkyl, most preferably H;

$R^{12}$ is H, alkyl or aryl, preferably H, methyl, ethyl, unsubstituted phenyl or 4-alkoxyphenyl;

$R^{22}, R^{23}$
are each independently H, alkyl, aryl, preferably aryl, or
$R^{22}$ and $R^{23}$ together form a cyclic radical, preferably a 5- or 6-membered radical;

Y, Z, W are each S, SO₂, O, SO, preferably S or SO₂; and

Ar is arylene, preferably phenylene, naphthylene or biphenylene;

$R^{31}$ is H, alkyl or aryl;

as emitter substances, especially substances emitting in the blue region of the electromagnetic spectrum, or hole and exciton blockers, in organic light-emitting diodes.

The emitter substances of the formula I which are used in accordance with the invention are readily obtainable and have good illumination densities and quantum yields when used in OLEDs. They are especially notable as emitter substances with good illumination properties even when they are used in substance, i.e. without matrix material, in the light-emitting layer of an OLED. As a result, no costly and inconvenient coevaporation with a matrix material is required to apply the light-emitting layer of the OLED. Thus, the process for producing OLEDs which have the emitter substances of the formula I used in accordance with the invention can be carried out inexpensively.

In addition, the compounds of the formula I can be used as hole and exciton blockers in organic light-emitting diodes.

The alkyl, alkenyl and alkynyl radicals, and also the alkyl radicals of the alkoxy groups, according to the present application may be straight-chain, branched, cyclic and/or optionally substituted by substituents selected from the group consisting of aryl, alkoxy, NR²²R²³ and halogen, where R²² and R²³ are as defined above.

Suitable halogen substituents are fluorine, chlorine, bromine and iodine, preferably fluorine, chlorine and bromine, more preferably fluorine and chlorine.

Suitable aryl substituents are specified below. The alkyl, alkenyl and alkynyl radicals are preferably unsubstituted.

Examples of suitable alkyl groups are methyl, ethyl, propyl, butyl, pentyl, hexyl, heptyl and octyl. This includes both the n-isomers of these radicals and branched isomers such as isopropyl, isobutyl, isopentyl, sec-butyl, tert-butyl, neopentyl, 3,3-dimethylbutyl, etc. Preferred alkyl groups are methyl and ethyl.

Cyclic alkyl radicals (cycloalkyl radicals) refer to cycloalkyl and also cycloalkylalkyl (alkyl which is in turn substituted by cycloalkyl), where cycloalkyl has at least three carbon atoms. Examples of cycloalkyl radicals are: cyclopropyl, cyclobutyl, cyclopentyl, cyclohexyl, cycloheptyl, cyclooctyl, cyclononyl and cyclodecyl. If appropriate, they may also be polycyclic ring systems such as decalinyl, norbornanyl, bornanyl or adamantyl. The cycloalkyl radicals may be unsubstituted or optionally substituted by one or more further radicals as listed above by way of example for the alkyl radicals.

Examples of alkenyl and alkynyl groups are: vinyl, 1-propenyl, 2-propenyl (allyl), 2-butenyl, 2-methyl-2-propenyl, 3-methyl-2-butenyl, ethynyl, 2-propynyl (propargyl), 2-butynyl or 3-butynyl.

Suitable alkoxy groups have the general formula —OR²⁴ where $R^{24}$ is an alkyl radical as defined above. Suitable alkoxy substituents are selected from the group consisting of OCH₃, OC₂H₅, OC₃H₇ and OC₄H₉. In this context, the terms C₃H₇ and C₄H₉ comprise both the n-isomers and branched isomers such as isopropyl, isobutyl, sec-butyl and tert-butyl. Particular preference is given to methoxy and ethoxy. In addition, $R^{24}$ may be an aralkyl radical, for example benzyl or phenylethyl.

In the present invention, aryl denotes radicals which are derived from monocyclic or bicyclic aromatics which do not comprise any ring heteroatoms. When the radicals are not monocyclic systems, the saturated form (perhydro form) or the partly unsaturated form (for example the dihydro form or tetrahydro form) are also possible for the second ring in the term aryl, as long as the particular forms are known and stable. This means that the term aryl in the present invention also includes, for example, bicyclic radicals in which either both radicals are aromatic or bicyclic radicals in which only one ring is aromatic. Examples of aryl are phenyl, naphthyl, indanyl, 1,2-dihydronaphthenyl, 1,4-dihydronaphthenyl, indenyl or 1,2,3,4-tetrahydronaphthyl. Aryl is more preferably phenyl or naphthyl, most preferably phenyl. In the context of the present application, Ph means phenyl.

The aryl radicals may be unsubstituted or substituted by one or more further radicals. Suitable further radicals are selected from the group consisting of alkyl, aryl, alkoxy, $NR^{22}R^{23}$ and halogen. In addition, suitable radicals are those of the formula $OC(O)R^{32}$ where $R^{32}$ is H, alkyl or aryl, preferably aryl, more preferably phenylcarbonyloxy, and radicals of the formula $OR^{33}$ where $R^{33}$ is H, alkyl or aryl, preferably H, and heteroaryl radicals and aryloxy radicals. Preferred alkyl, aryl, alkoxy and halogen radicals and heteroaryl radicals and aryloxy radicals and definitions of the $R^{22}$, $R^{23}$ radicals have already been specified above. The aryl radicals are preferably unsubstituted or substituted by one or more alkoxy groups. Aryl is more preferably unsubstituted phenyl or 4-alkoxyphenyl. Aryl is most preferably unsubstituted phenyl.

Heteroaryl refers to heteroaryl radicals which differ from the aforementioned aryl radicals in that at least one carbon atom has been replaced by a heteroatom in the basic skeleton of the aryl radicals. Preferred heteroatoms are N, O and S. Very particular preference is given to one, two or three carbon atoms of the basic skeleton of the aryl radicals being replaced by heteroatoms. The basic skeleton is especially preferably selected from systems such as pyridyl, pyridazinyl, pyrimidinyl, pyrazinyl, triazinyl, cyclic esters, cyclic amides and 5-membered heteroaromatics such as triazolyl, imidazolyl, pyrazolyl, thienyl, pyrrolyl and furyl, and fused systems such as benzimidazolyl. The basic skeleton may be substituted at one of, a plurality of or all substitutable positions of the basic skeleton. Suitable substituents are the same as have already been specified for aryl.

Suitable aryloxy groups have the general formula $-OR^{25}$ where $R^{25}$ is an aryl radical as defined above. Particular preference is given to phenoxy.

According to the present application, arylene refers to a phenylene, naphthylene or biphenylene group which may be unsubstituted or substituted by the substituents specified for the aryl radicals. The arylene group is preferably unsubstituted. Preferred phenylene groups are 1,3- or 1,4-phenylene, particular preference being given to 1,4-phenylene; preferred naphthylene groups are 1,5-, 1,6-, 2,6- or 2,7-naphthylene, preference being given to 1,5- or 2,6-naphthylene; preferred biphenylene groups are 4,4'-biphenylene.

Suitable amino groups have the formula $NR^{22}R^{23}$ where $R^{22}$ and $R^{23}$ are each independently H, alkyl or aryl, preferably aryl. In addition, $R^{22}$ and $R^{23}$ together with the nitrogen atom of the amino group may form a cyclic radical, preferably a 5- or 6-membered cyclic radical. This may comprise further heteroatoms selected from N, O and S as well as the nitrogen atom.

In a preferred embodiment, the present invention relates to the use of emitter substances or hole and exciton blockers of the formula I in which the symbols and radicals are each defined as follows:

X is S or $SO_2$, preferably $SO_2$;
$R^1$ is H, methyl, ethyl, unsubstituted phenyl or 4-alkoxyphenyl or phenyl or pyridyl substituted by one OH, OC(O)Ph, $OCH_2Ph$ or N-phenyl-benzimidazolyl group, three $CH_3$ groups or two F radicals;

or

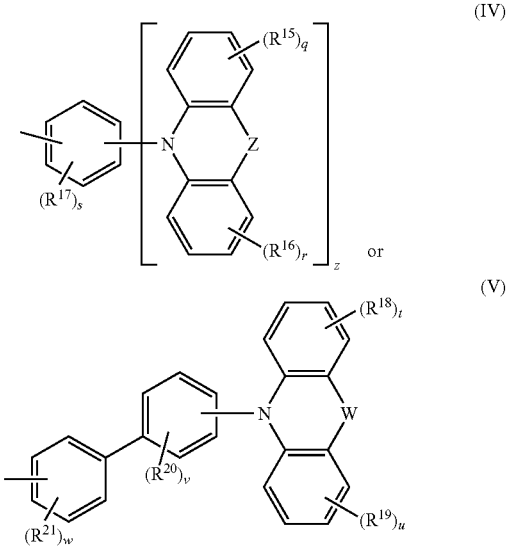

$R^2$, $R^3$ are each H, unsubstituted phenyl, 1-naphthyl, 2-naphthyl or $NR^{22}R^{23}$ or CHO, where at least one of the $R^2$ or $R^3$ radicals is unsubstituted phenyl, 1-naphthyl, 2-naphthyl or $NR^{22}R^{23}$ or CHO,
or
$R^2$ and $R^3$ are each

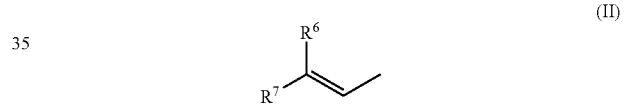

or
$R^2$ is H and $R^3$ is

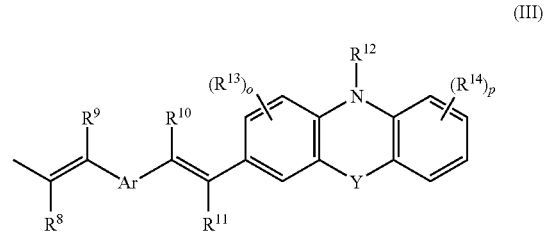

m, n, o, p, q, r, s, t, u, v and w
  are each 0, 1 or 2, preferably 0;
z is 1 or 2, preferably 1;
$R^6$, $R^7$ are each unsubstituted phenyl;
$R^8$, $R^9$, $R^{10}$, $R^{11}$
  are each H;
$R^{12}$ is H, methyl, ethyl, unsubstituted phenyl or 4-alkoxyphenyl or phenyl substituted by three $CH_3$ groups;
$R^{17}$ is alkyl, alkoxy, preferably methoxy;
$R^{22}$, $R^{23}$ are each aryl;
Y, Z, W are each S or $SO_2$, preferably $SO_2$; and
Ar is phenylene, naphthylene or biphenylene.

The emitter substance of the formula I is more preferably selected from the group consisting of compounds of the formulae Ia, Ib, Ic, Id, Ie, If and Ig

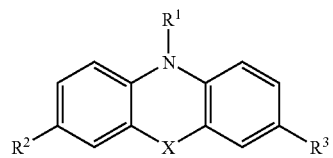 (Ia)

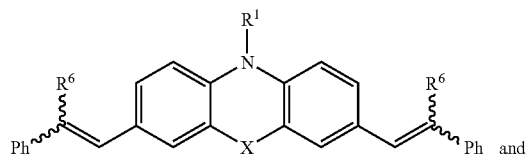 (Ib) and (Ic)

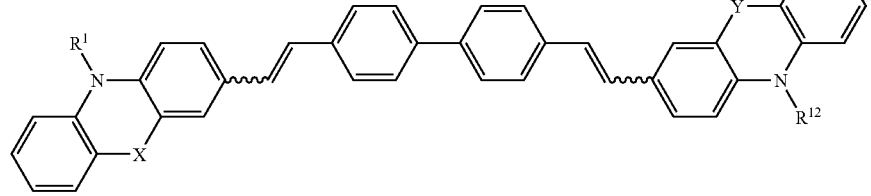

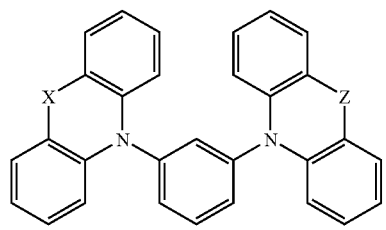 (Id)

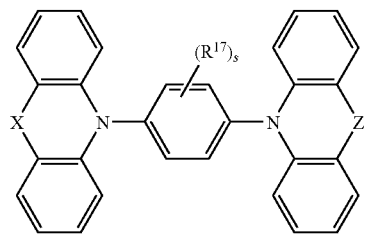 (Ie)

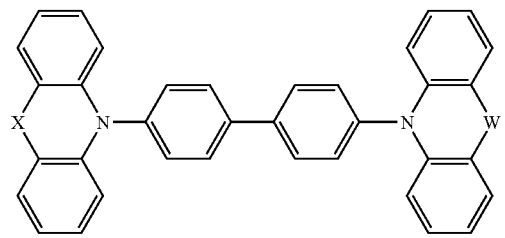 (If)

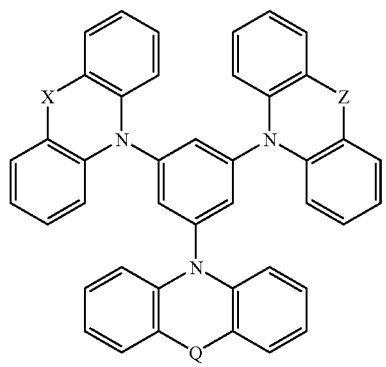 (Ig)

in which:

X, Y, Z, W, Q
  are each independently S or $SO_2$, preferably $SO_2$; and
$R^1$, $R^{12}$ are each H, methyl, ethyl or unsubstituted phenyl;
$R^2$, $R^3$ are each H or unsubstituted phenyl, where at least $R^2$ or $R^3$ is unsubstituted phenyl;
$R^6$ is methyl or unsubstituted phenyl;
$R^{17}$ is methoxy;
s is 0 or 2, where the substituents, in the case that s=2, are preferably arranged in the 2- and the 5-position;
Ph is unsubstituted phenyl.

The compounds of the formulae Ia, Ib and Ic are more preferably symmetrical, i.e. $R^2$ and $R^3$ in the compound of the formula Ia are more preferably identical, both $R^6$ radicals in the compound of the formula Ib are more preferably identical, and $R^1$ and $R^{12}$, and X and Y, in the compound of the formula Ic are preferably identical; X and Z in the compounds of the formulae Id and Ie are more preferably identical, X and W in the compound of the formula If are more preferably identical, and X, Z and Q in the compound of the formula Ig are more preferably identical.

In a further preferred embodiment, emitter substance of the formula I is selected from the group consisting of compounds of the formulae Ih and Ii

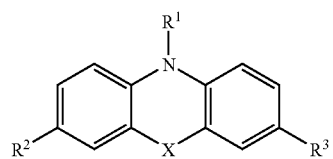 (Ih)

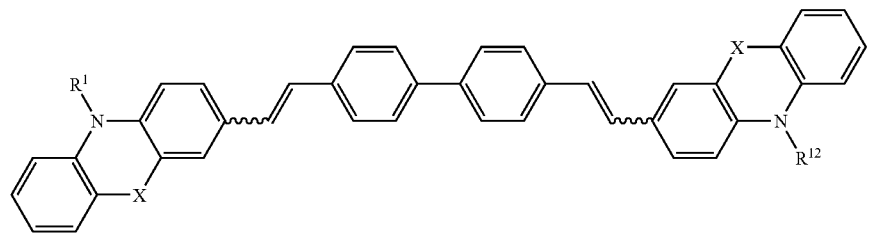
(Ii)

in which
X, Y are each independently S or SO$_2$, preferably SO$_2$;
R$^1$ is phenyl, 4-methoxyphenyl, thienyl or pyridyl substituted by one OH, OC(O)Ph, OCH$_2$Ph or N-phenylbenzimidazolyl group, three CH3 groups or two F radicals;
R$^2$ is H;
R$^3$ is H or CHO, preferably H,
R$^{12}$ is phenyl substituted by three CH$_3$ groups.

Preferred compounds of the formula I used as hole and exciton blockers are selected from the group consisting of compounds of the formulae Ia, Id, Ie, Ig and Ih; more preferably, the hole and exciton blockers are selected from compounds of the formulae Ia and Ih.

The aforementioned phenoxazine, phenothiazine, phenothiazine S-oxide or phenothiazine S,S-dioxide derivatives of the formula I used in accordance with the invention may be prepared by processes known to those skilled in the art.

The compounds of the formula I in which X, Y, Z, W and Q are each S or O may be prepared either by appropriate substitution of the commercially available phenoxazine or phenothiazine basic skeleton in which R$^1$, R$^2$, R$^3$, R$^4$ and R$^5$ are each H. When they are not H, the R$^2$, R$^3$, R$^4$ and R$^5$ radicals are introduced by electrophilic aromatic substitution. Suitable reaction conditions are known to those skilled in the art. When the R$^1$ radical is not H, it is introduced by electrophilic substitution on the nitrogen, for example, by reaction with a suitable alkyl or aryl halide. In a further preferred reaction with a suitable alkyl or aryl halide. In a further preferred embodiment, the basic skeleton is functionalized, for example halogenated or functionalized with aldehyde groups. The functionalized basic skeleton is subsequently reacted with the appropriate compounds bearing the R$^2$, R$^3$, R$^4$ and R$^5$ radicals by a coupling reaction or by Wittig reaction to give the desired phenoxazines or phenothiazines.

Alternatively, the compounds of the formula I may be prepared starting from already functionalized building blocks suitable for the preparation of phenoxazine derivatives, phenothiazine derivatives, phenothiazine S-oxide derivatives or phenothiazine S,S-dioxide derivatives. For example, the phenoxazine derivatives used in accordance with the invention may be prepared by heating o-aminophenol functionalized with the R$^2$ and R$^4$ radicals with its hydrochloride functionalized with the R$^3$ and R$^5$ radicals. The functionalized building blocks are prepared by the process known to those skilled in the art. The phenothiazine derivatives used in accordance with the invention may be prepared starting from diphenylamine derivatives functionalized with the R$^2$, R$^3$, R$^4$ and R$^5$ radicals by heating with sulfur. The preparation of the functionalized diphenylamine derivatives is known to those skilled in the art.

Preference is given to preparing the compounds of the formula I used in accordance with the invention starting from the commercially available phenoxazine and phenothiazine basic skeletons.

The compounds of the formula I in which X is SO$_2$ or SO are prepared, for example, by oxidation of the corresponding functionalized phenothiazine Suitable processes for oxidizing phenothiazines to phenothiazine S-oxides and phenothiazine S,S-dioxides are known to those skilled in the art and specified, for example, in M. Tosa et al. Heterocyclic Communications, Vol. 7, No. 3, 2001, p. 277 to 282.

The oxidation to phenothiazine S-oxide derivatives is effected, for example, by means of H$_2$O$_2$ in ethanol or ethanol-acetone mixtures, H$_2$O$_2$ in oxalic acid, ammonium persulfate, nitric acid, nitrous acid, inorganic nitrogen oxides, NO$_2$/O$_2$, NO$^+$BF$_4^-$/O$_2$, CrO$_3$ in pyridine, ozone, tetramethyloxirane, perfluoroalkyloxaziridines or by means of electrochemical methods. In addition, the appropriately functionalized phenothiazines of the formula I can be oxidized to the corresponding phenoxazine S-oxide derivatives of the formula I by means of m-chloroperbenzoic acid in CH$_2$Cl$_2$ at temperatures of from 0 to 5° C. or by means of a mixture of fuming nitric acid and glacial acetic acid in CCl$_4$ (see, for example, M. Tosa et al. Heterocyclic Communications, Vol. 7, No. 3, 2001, p. 277 to 282).

The oxidation to phenothiazine S,S-dioxide derivatives is effected, for example, by means of peracids such as peracetic acid which is formed, for example, from H$_2$O$_2$ and AcOH, or m-chloroperbenzoic acid, sodium perborate, NaOCl or heavy metal systems such as KMnO$_4$/H$_2$O, Et$_3$PhN$^+$MnO$_4^-$ in organic media, OsO$_4$/N-methylmorpholine N-oxide. For example, the appropriately functionalized phenothiazines of the formula I can be oxidized to the corresponding phenothiazine S,S-dioxide derivatives of the formula I by means of an aqueous solution of KMnO$_4$ and C$_{16}$H$_{35}$N(CH$_3$)$_3^+$Cl$^-$ in CHCl$_3$ at room temperature or by means of m-chloroperbenzoic acid in CH$_2$Cl$_2$ at room temperature (see, for example, M. Tosa et al. Heterocyclic Communications, Vol. 7, No. 3, 2001, p. 277-282).

To prepare phenothiazine S,S-dioxide derivatives in which X is SO$_2$, the phenothiazine derivative and the oxidizing agent, preferably m-chloroperbenzoic acid are used in a molar ratio of generally from 1:1.8 to 1:4, preferably from 1 to 1.9 to 1:3.5, more preferably from 1:1.9 to 1:3.

To prepare phenothiazine S-oxide derivatives in which X is SO, the phenothiazine derivative and the oxidizing agent are used in a molar ratio of generally from 1:0.8 to 1:1.5, preferably 1:1 to 1:1.3. Oxidizing agents with which no further oxidation to the corresponding S,S-dioxide derivatives occurs, for example H$_2$O$_2$, may be used in a larger excess than that specified above in relation to the phenothiazine derivative.

The oxidation is effected generally in a solvent, preferably in a solvent selected from the group consisting of halogenated hydrocarbons such as methylene chloride and dipolar aprotic solvents such as acetonitrile or sulfolane.

In general, the oxidation to the phenothiazine S-oxide derivatives is carried out at a temperature of from −10° C. to +50° C., preferably from −5° C. to +30° C., more preferably from 0° C. to +20° C. Typically, the oxidation is effected at standard pressure. The reaction time of the oxidation is generally from 0.25 to 24 hours, preferably from 1 to 15 hours, more preferably from 2 to 10 hours.

The oxidation to the phenothiazine S,S-dioxide derivatives is effected generally at a temperature of from +0 to +100° C. Typically, the oxidation is effected at standard pressure.

In a preferred embodiment, the phenothiazine S-oxide derivatives of the formula I are prepared by oxidizing the corresponding phenothiazine derivatives of the formula I with m-chloroperbenzoic acid as the oxidizing agent in $CH_2Cl_2$ at from 0 to 20° C.

The phenothiazine S,S-dioxide derivatives of the formula I are prepared preferably by oxidizing the corresponding phenothiazine derivatives of the formula I with m-chloroperbenzoic acid as the oxidizing agent in $CH_2Cl_2$ at from 0 to 40° C.

The resulting phenothiazine S-oxides and phenothiazine S,S-dioxides are isolated and worked up by processes known to those skilled in the art.

The preparation of the compounds of the formula I used in accordance with the invention will be illustrated below by way of example with reference to preparation processes of the compounds of the formulae Ia, Ib, Ic, Id, Ie, If and Ig used with preference, and of the compounds of the formulae Ih and Ii used with preference. On the basis of this information and with knowledge of the prior art, the person skilled in the art is in a position to prepare the further compounds used in accordance with the invention.

a) Preparation of the Compounds of the Formulae Ia and Ih Used with Preference

The compounds of the formulae Ia and Ih used with preference are prepared, for example, starting from a basic skeleton of the following formula VI

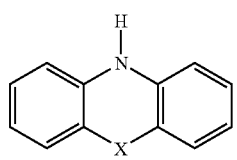

VI in which X is S or $SO_2$,
by
aa) N-alkylation or N-arylation of the basic skeleton of the formula VI,
ab) halogenation, and
ac) coupling reaction with the precursor compounds corresponding to the desired $R^2$ and $R^3$ radicals;
ad) if appropriate oxidation in the case that X=S;
the step aa) being carried out only when $R^1$ is not H.

Suitable reaction conditions for carrying out steps aa), ab), ac) and ad) are known to those skilled in the art. Preferred embodiments of steps aa), ab), ac) and ad) are specified below.

Step aa)

The N-alkylation or N-arylation is effected preferably by reacting the basic skeleton of the formula VI with an alkyl halide or aryl halide of the formula $R^1$-Hal where $R^1$ has already been defined above and Hal is Cl, Br or I, preferably I.

The N-alkylation or N-arylation is carried out in the presence of a base. Suitable bases are known to those skilled in the art and are preferably selected from the group consisting of alkali metal and alkaline earth metal hydroxides such as NaOH, KOH, $Ca(OH)_2$, alkali metal hydrides such as NaH, KH, alkali metal amides such as $NaNH_2$, alkali metal or alkaline earth metal carbonates such as $K_2CO_3$, and alkali metal alkoxides such as NaOMe, NaOEt. Also suitable are mixtures of the aforementioned bases. Particular preference is given to NaOH, KOH or NaH.

The N-alkylation (for example disclosed in M. Tosa et al., Heterocycl. Communications, Vol. 7, No. 3, 2001, p. 277-282) or N-arylation (for example disclosed in H. Gilman and D. A. Shirley, J. Am. Chem. Soc. 66 (1944) 888; D. Li et al., Dyes and Pigments 49 (2001) 181-186) is preferably carried out in a solvent. Suitable solvents are, for example, polar aprotic solvents such as dimethyl sulfoxide, dimethylformamide or alcohols. It is likewise possible to use an excess of the alkyl or aryl halide used as a solvent, preference being given to the use of an excess of alkyl or aryl iodides. The reaction may additionally be carried out in a nonpolar aprotic solvent, for example toluene, when a phase transfer catalyst, for example tetra-n-butylammonium hydrogensulfate, is present (as disclosed, for example, in I. Gozlan et al., J. Heterocycl. Chem. 21 (1984) 613-614).

The N-arylation may be effected, for example, by copper-catalyzed coupling of the compound of the formula VI with an aryl halide, preferably an aryl iodide (Ullmann reaction). A suitable process for N-arylating phenothiazine in the presence of copper bronze is disclosed, for example, in H. Gilman et al., J. Am. Chem. Soc. 66 (1944) 888-893.

The molar ratio of the compound of the formula VI to the alkyl halide or aryl halide of the formula $R^1$-Hal is generally from 1:1 to 1:2, preferably from 1:1 to 1:1.5.

The N-alkylation or N-arylation is carried out generally at a temperature of from 0 to 220° C., preferably from 20 to 200° C. The reaction time is generally from 0.5 to 48 h, preferably from 1 to 24 h. In general, the N-alkylation or N-arylation is carried out at standard pressure.

The resulting crude product is worked up by processes known to those skilled in the art.

If $R^1$ in the compound of the formula Ia is H, step aa) is not required.

Step ab)

The halogenation may be carried out by processes known to those skilled in the art. Preference is given to brominating or iodinating in the 3- and 7-position of the basic structure of the formula VI which has been N-alkylated or N-arylated if appropriate.

The basic structure of the formula VI which has been N-alkylated or N-arylated in step aa) if appropriate may be brominated in the 3- and 7-position of the basic skeleton, for example, according to M. Jovanovich et al. J. Org. Chem. 1984, 49, 1905-1908 by reacting with bromine in acetic acid. In addition, a bromination may be effected according to the process disclosed in C. Bodea et al. Acad. Rep. Rom. 13 (1962) 81-87.

The basic skeleton of the formula VI which has been N-alkylated or N-arylated in step aa) if appropriate may be iodinated in the 3- and 7-position of the basic skeleton, for example, according to the process disclosed in M. Sailer et al. J. Org. Chem. 2003, 68, 7509-7512. In this process, the corresponding 3,7-dibromo-substituted basic skeleton of the formula VI which has been N-alkylated or N-arylated if appropriate is initially lithiated and the lithiated product is subsequently iodinated.

The lithiation may be carried out with a lithium base selected from the group consisting of n-butyllithium and lithium diisopropylamide at temperatures of generally from −78 to +25° C., preferably from −78 to 0° C., more preferably −78° C., by the process known to those skilled in the art.

Subsequently, the reaction mixture is warmed to room temperature and worked up by processes known to those skilled in the art.

Step ac)

The phenothiazine derivatives of the formula Ia used in accordance with the invention are prepared preferably by coupling reaction with the precursor compounds corresponding to the desired $R^2$ and $R^3$ radicals. Suitable coupling reactions are, for example, the Suzuki coupling and the Yamamoto coupling, preference being given to the Suzuki coupling.

In the Suzuki coupling, compounds which have been halogenated, especially brominated, at the 3 and 7 positions of the phenothiazine basic skeleton of the formula VI which has been N-alkylated or N-arylated if appropriate may be reacted with the boronic acids or boronic esters corresponding to the desired $R^2$ and $R^3$ radicals under Pd(0) catalysis in the presence of a base to give the corresponding 3,7-$R^2$, $R^3$-substituted compounds.

Instead of the boronic acids or boronic esters corresponding to the desired $R^2$ and $R^3$ radicals, it is also possible to use other boron compounds which bear the desired $R^2$ and $R^3$ radicals in the reaction with the halogenated phenothiazine derivatives. The boron compounds are cyclic compounds of the general formulae $R^2$—B(—O—[C($R^{27}$)$_2$]$_n$—O—) and $R^3$—B(O)—[C($R^{27}$)$_2$]$_n$—O—) where $R^2$ and $R^3$ each have the definitions specified for $R^2$ and $R^3$, $R^{27}$ is the same or different and is selected from hydrogen or $C_1$-$C_{20}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-decyl, n-dodecyl or n-octadecyl; preferably $C_1$-$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl or n-decyl, more preferably $C_1$-$C_4$-alkyl such as methyl, ethyl, n-propyl, isopropyl, n-butyl, isobutyl, sec-butyl and tert-butyl, most preferably methyl; and n is an integer from 2 to 10, preferably from 2 to 5.

The boronic acids, boronic esters and boron compounds corresponding to the desired $R^2$ and $R^3$ radicals may be prepared by processes disclosed in the prior art or are commercially available. For example, it is possible to prepare the boronic acids and boronic esters by reacting Grignard or lithium reagents with boranes, diboranes or borates.

Suitable Pd(0) catalysts are all customary Pd(0) catalysts. For example, it is possible to use tris(dibenzylideneacetone) dipalladium(0) or tetrakis(triphenylphosphine)palladium(0). In addition, it is possible to use a Pd(II) salt in a mixture with a ligand, for example Pd(ac)$_2$ or PdCl$_2$ and PPh$_3$, in which case Pd(0) is formed in situ. To carry out the coupling, an excess of PPh$_3$ may be added. The catalysts are used generally in an amount of from 0.001 to 15 mol %, preferably from 0.01 to 10 mol %, more preferably from 0.1 to 5 mol %, based on the halogenated phenothiazine derivative used.

In the Suzuki coupling all bases used customarily in the Suzuki coupling may be used. Preference is given to using alkali metal carbonates such as sodium carbonate or potassium carbonate. The base is used generally in a molar excess of from 2 to 200 times, preferably from 2 to 100 times, more preferably from 2 to 80 times, based on the halogenated phenothiazine derivative used.

The component corresponding to the desired $R^2$ and $R^3$ radicals (boronic acid, the corresponding boric ester or the other suitable boron compounds) is used in a ratio to the halogenated phenothiazine derivative of from 100 to 400 mol %, preferably from 100 to 300 mol %, more preferably from 100 to 150 mol %.

The reaction is effected generally at a temperature of from 40 to 140° C., preferably from 60 to 120° C., more preferably from 70 to 100° C. The pressure is generally standard pressure.

The reaction is carried out generally with exclusion of oxygen. Typically, the reaction is effected in a solvent selected from the group consisting of benzene, toluene, tetrahydrofuran, 1,4-dioxane, dimethoxyethane, ethanol and petroleum ether. It is likewise possible to use a mixture of tetrahydrofuran, dimethoxyethane or ethanol and water as the solvent.

In an advantageous variant of the process, a halogenated phenothiazine derivative is initially charged in solution under protective gas and admixed with the base which is preferably present in dissolved form, for example in a dimethoxyethane/water mixture, and a boronic acid corresponding to the desired $R^2$ and $R^3$ radicals. Afterward, the Pd(0) catalyst is added under protective gas. The mixture is stirred at the aforementioned temperatures and pressures over a period of generally from 3 to 120 hours, preferably from 4 to 72 hours, more preferably from 6 to 48 hours. Afterward, the reaction mixture is worked up by processes known to those skilled in the art.

The phenothiazine derivatives of the formula Ia used in accordance with the invention may be prepared, in addition to the Suzuki coupling, by other processes known to those skilled in the art, in particular other coupling reactions.

In a further embodiment of the present invention, the inventive phenothiazine derivatives of the formula Ia are obtained by reacting phenothiazines which have a basic skeleton of the formula VI, have been N-alkylated or N-arylated if appropriate and are halogenated, especially brominated, at the 3 and 7 positions with the halogen compounds corresponding to the desired $R^2$ and $R^3$ radicals, in particular bromine compounds, under Ni(0) catalysis (Yamamoto coupling).

In a preferred embodiment of the Yamamoto coupling, a solution, preferably a DMF solution, of the catalyst is prepared under exclusion of oxygen from an Ni(0) compound, preferably Ni(COD)$_2$, and bipyridyl in equimolar amounts. Under exclusion of oxygen, the halogenated, preferably brominated, phenothiazine derivative and the bromine compounds corresponding to the desired $R^2$ and $R^3$ radicals are added in a solvent, preferably toluene, to this solution.

The reaction conditions such as temperature, pressure, solvent and ratio of the halogenated, preferably brominated, phenothiazine derivative to the component corresponding to $R^2$ and $R^3$ in the preparation of the phenothiazine derivatives of the formula Ia by means of Yamamoto coupling correspond to those of the Suzuki coupling.

Suitable Ni(0) compounds for preparing the catalyst are all customary Ni(0) compounds. For example, it is possible to use Ni($C_2H_4$)$_3$, Ni(1,5-cyclooctadiene)$_2$ ("Ni(COD)$_2$"), Ni(1,6-cyclodecadiene)$_2$ or Ni(1,5,9-all-trans-cyclododecatriene)$_2$. The catalysts are used generally in an amount of from 1 to 100 mol %, preferably from 5 to 80 mol %, more preferably from 10 to 70 mol %, based on the halogenated phenothiazine derivative used.

Suitable process conditions and catalysts, especially for the Suzuki coupling, are disclosed, for example, in Suzuki-Miyaura cross-coupling: A. Suzuki, J. Organomet. Chem. 576 (1999) 147-168; B-alkyl Suzuki-Miyaura cross-coupling: S. R. Chemler et al., Angew. Chem. 2001, 113, 4676-4701 and the literature cited therein.

Step ad)

Preferred oxidizing agents and process conditions for the oxidation of the phenothiazines to the corresponding phenothiazine S,S-dioxide derivatives are specified above and disclosed, for example, in M. Tosa et al., Heterocyclic Commun. 7 (2001) 277-282.

b) Preparation of the Compounds of the Formula Ib Used with Preference

The compounds of the formula Ib used with preference are prepared, for example, starting from a basic skeleton of the following formula VI

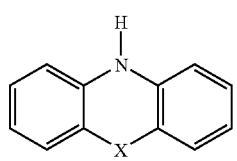

VI in which X is S or $SO_2$,
by
ba) N-alkylation or N-arylation of the basic skeleton of the formula VI, step ba) being carried out only when $R^1$ is not H;
bb) conversion of the resulting compound to a bisaldehyde of the formula VII

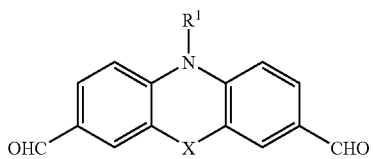

VII bc) reaction of the bisaldehyde of the formula VII with alkylphosphonic ester of the formula VIII

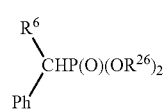

VIII where $R^{26}$ is $C_1$- to $C_6$-alkyl,
to obtain a phenothiazine of the formula Ib which is symmetrical, i.e. $R^6$ is in each case either Me or unsubstituted Ph.

An unsymmetrical compound of the formula Ib in which one $R^6$ is Me and the other is unsubstituted Ph may be obtained, for example, by reacting the bisaldehyde of the formula VII in step bc) first with one molar equivalent of an alkylphosphonic ester of the formula VIII in which $R^6$ is Me and then with one molar equivalent of an alkylphosphonic ester of the formula VIII in which $R^6$ is Ph, or first with one molar equivalent of an alkylphosphonic ester of the formula VIII in which $R^6$ is Ph and then with one molar equivalent of an alkylphosphonic ester of the formula VIII in which $R^6$ is Me.

In addition, it is also possible to obtain an unsymmetrical compound of the formula Ib by initially preparing a monoaldehyde by means of Vilsmeier-Haack reaction (for example by a process as disclosed in N. P. Buu-Hoi, N. Hoán, J. Chem. Soc. 1951, 1834-1836 or L. Gaina et al., Heterocycl. Commun. 7 (2001), 549-554) and reacting it with one molar equivalent of an alkylphosphonic ester of the formula VIII in which $R^6$ is Ph or Me. This affords a compound of the following formula IX in which X and $R^1$ are each as defined for formula Ib and $R^6$ is Ph or Me:

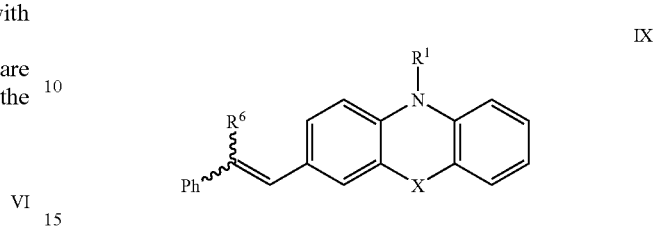

IX

Afterward, the resulting compound is converted by means of a further Vilsmeier-Haack reaction (for example by a process as disclosed in N. P. Buu-Hoi, N. Hoán, J. Chem. Soc. 1951, 1834-1836 or L. Gaina et al., Heterocycl. Commun. 7 (2001), 549-554) to an aldehyde of the following formula X in which X and $R^1$ are each as defined for formula Ib and $R^6$ is Ph or Me:

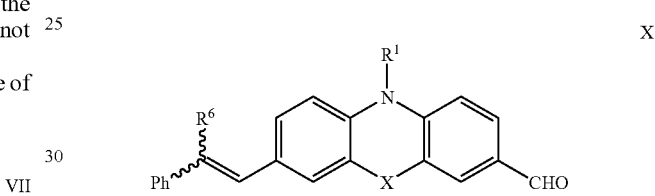

X

The aldehyde of the formula X is reacted with one molar equivalent of an alkylphosphonic ester of the formula VIII in which $R^6$ is Ph or Me, $R^6$ being different from the $R^6$ radical already present in the aldehyde of the formula X.

bd) Oxidation, if appropriate, of the phenothiazine derivative of the formula Ib to the corresponding phenothiazine S,S-oxide derivative of the formula Ib Suitable oxidizing agents and process conditions are specified above and disclosed, for example, in M. Tosa et al., Heterocyclis Commun. 7 (2001) 277-282.

Alternatively, it is possible after step bb) first to oxidize to the corresponding phenothiazine S,S-dioxide derivative (step bd) and then subsequently to react with an alkylphosphonic ester of the formula VIII (step bc).

Suitable reaction conditions for carrying out steps ba), bb) and bc) are known to those skilled in the art. Preferred embodiments of step ba), bb) and bc) are specified below.

Step ba)

The N-alkylation or N-arylation of the basic skeleton of the formula VI in step ba) preferably corresponds to the process for preparing a compound of the formula Ia) already described in step aa).

Step bb)

A suitable process for carrying out step bb) for preparing symmetrical bisaldehydes is disclosed, for example, in U.S. Pat. No. 5,942,615 and in H. Oelschläger and H. J. Peters, Arch. Pharm. (Weinheim) 320 (1987) 379-381. The bisaldehyde of the formula VII is preferably prepared by reacting the reaction product from step ba), in the case that $R^1$ is not H (if $R^1$ is H, the compound of the formula VI is used), with a formamide, e.g. N,N-dimethylformamide or N-methylformanilide, if appropriate in the presence of $POCl_3$ and of a Lewis acid or of a Brønsted acid, e.g. $ZnCl_2$. Preference is given to preparing the bisaldehydes by the process described in H. Oelschläger and H. J. Peters, Arch, Pharm. (Weinheim) 320 (1987) 379-381.

A suitable process for carrying out step bb) for the preparation of monoaldehydes which may be used to prepare unsymmetrical compounds of the formula Ib is disclosed, for example, in N. P. Buu-Hoi, N. Hoán, J. Chem. Soc. 1951, 1834-1836 and L. Gaina et al., Heterocycl. Commun. 7 (2001), 549-554. For example, the monoaldehyde may be obtained by reacting the phenothiazine basic skeleton of the formula VI which has been N-alkylated or N-arylated if appropriate with a formamide, for example N-methylformanilide or N,N-dimethylformamide, phosphorus oxychloride in o-dichlorobenzene or in the absence of solvents (in that case generally with an excess of formamide).

The reaction may be carried out in an organic solvent, for example in toluene, xylene, chlorobenzene, o-dichlorobenzene (for monoaldehyde) or in acetonitrile (for bisaldehyde).

Step bc)

A suitable process for carrying out step bc) is disclosed, for example, in U.S. Pat. No. 5,942,615. The bisaldehyde of the formula VII is reacted with an alkylphosphonic ester of the formula VIII preferably in the presence of a base.

Suitable bases are, for example, hydroxides such as NaOH, KOH, amides such as sodium amide, hydrides such as NaH, KH, and metal alkoxides such as NaOMe, NaOtBu, KOtBu.

The reaction may be carried out in a solvent. Suitable solvents are alcohols such as methanol, ethanol, ethers such as 1,2-dimethoxyethane, diethyl ether, tetrahydrofuran or dioxane, hydrocarbons such as toluene or xylene, polar aprotic solvents such as dimethyl sulfoxide, N,N-dimethylformamide, N,N-dimethylacetamide or N-methylpyrrolidone, or mixtures of the solvents mentioned.

The molar ratio between the bisaldehyde of the formula VII and the alkylphosphonic ester of the formula VIII for the preparation of symmetrical compounds of the formula Ib, i.e. compounds in which $R^6$ is in each case Ph or in each case Me, is generally 1:2. When an unsymmetrical compound of the formula Ib in which one $R^6$ is Me and the other is unsubstituted Ph is prepared, reaction is effected first with one molar equivalent of an alkylphosphonic ester of the formula VIII in which $R^6$ is Me and then with one molar equivalent of an alkylphosphonic ester of the formula VIII in which $R^6$ is Ph, or first with one molar equivalent of an alkylphosphonic ester of the formula VIII in which $R^6$ is Ph and then with one molar equivalent of an alkylphosphonic ester of the formula VIII in which $R^6$ is Me. This means that the molar ratio between the bisaldehyde of the formula VII and the alkylphosphonic ester of the formula VIII is generally 1:1. The resulting compound is subsequently reacted in a molar ratio of 1:1, based on the compound which has already been reacted with one molar equivalent of the alkylphosphonic ester and the further phosphonic ester different from the first alkylphosphonic ester.

In the case of reaction of a monoaldehyde with an alkylphosphonic ester of the formula VII to prepare a compound of the formula IX, the monoaldehyde and the alkylphosphonic ester are reacted in a molar ratio of generally 1:1. The further reaction of the compound of the formula IX to give a compound of the formula X and subsequently to give an unsymmetrical compound of the formula Ic is effected according to steps bb) and bc). The required molar ratios of the components used can be determined readily by those skilled in the art.

The molar ratio of the base used to the alkylphosphonic ester is generally from 1:1 to 1:2, preferably from 1:1.1 to 1:1.5.

The reaction temperature is generally from 0° C. to 150° C., preferably from 20° C. to 80° C. The reaction time is generally from 0.5 to 24 h, preferably from 1 to 10 h. Typically, the reaction is carried out at standard pressure.

The alkylphosphonic ester is prepared, for example, by heating a mixture of the corresponding aralkyl chloride or bromide and trialkyl phosphite, either in substance or in a solvent, for example toluene or xylene.

Step bd)

The oxidation of the phenothiazine of the formula Ib to the corresponding phenothiazine S,S-dioxide of the formula Ib has already been described above. Suitable oxidizing agents and process conditions are specified above and disclosed, for example, in M. Tosa et al., Heterocyclic Commun. 7 (2001) 277-282.

Alternatively, it is possible after step bb) first to oxidize to the corresponding phenothiazine S,S-dioxide (step bd) and then to react with an alkylphosphonic ester of the formula VIII (step bc).

c) Preparation of the Compounds of the Formulae Ic and Ii Used with Preference

The compounds of the formulae Ic and Ii used with preference are prepared, for example, likewise starting from a basic skeleton of the formula VI

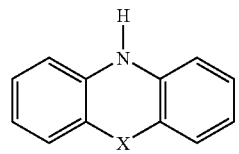

VI in which X is S or $SO_2$, by ca) N-alkylation or N-arylation of the basic skeleton of the formula VI, step ca) being carried out only when $R^1$ and $R^{12}$ are not H;

cb) conversion of the resulting compound to a monoaldehyde of the formula XIa or XIb by means of Vilsmeier-Haack reaction (see, for example, N. P. Buu-Hoi and N. Hoán, J. Chem. Soc. 1951, 1834-1836, Gaina et al., Heterocycl. Commun. 7 (2001), 549-554) or according to H. Oelschläger and H. J. Peters, Arch. Pharm. (Weinheim) 320 (1987) 379-381.

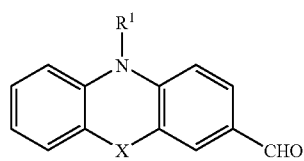

XIa

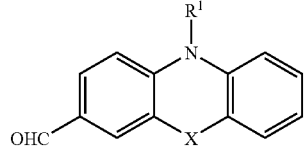

XIb cc) reaction of a compound of the formula XIa and a compound of the formula IXb with a phosphonic ester of the formula XII

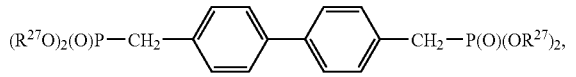

(XII)

$(R^{27}O)_2(O)P-CH_2-\phantom{}-\phantom{}-CH_2-P(O)(OR^{27})_2$, where $R^{27}$ is $C_1$- to $C_6$-alkyl
to obtain a phenothiazine derivative of the formula Ic.

cd) oxidation, if appropriate, of the phenothiazine derivative of the formula Ic to the corresponding phenothiazine S,S-dioxide.

Alternatively, the phenothiazine derivative which bears an aldehyde group and is obtained in step cb) may be converted to the corresponding phenothiazine S,S-dioxide derivatives (step cc'). These phenothiazine S,S-dioxide derivatives are subsequently converted by reaction with a phosphoric ester of the formula XII to the desired phenothiazine S,S-dioxide derivatives of the formula Ic (step cd').

Suitable reaction conditions for carrying out steps ca), cb), cc), cd), cc') and cd') are known to those skilled in the art. Preferred embodiments of steps ca), cb), cc), cd), cc') and cd') are specified below.

Step ca)

The N-alkylation or N-arylation of the basic skeleton of the formula VI in step ca) corresponds preferably to the process already described in step aa) for preparing a compound of the formula Ia. For the N-alkylation or N-arylation with an $R^{12}$ radical, instead of the alkyl halide or aryl halide of the formula $R^1$-Hal, an alkyl halide or aryl halide of the formula $R^{12}$-Hal is used under otherwise identical reaction conditions to those described in step aa) for the preparation of the compound Ia.

Step cb)

Step cb) may be carried out, for example, analogously to the processes disclosed in U.S. Pat. No. 5,942,615 and in N. P. Buu-Hoi and N. Hoán, J. Chem. Soc. 1951, 1834-1836, Gaina et al., Heterocycl. Commun. 7 (2001), 549-554) or according to H. Oelschläger and H. J. Peters, Arch. Pharm. (Weinheim) 320 (1987) 379-381 for preparing corresponding aldehydes. The N-alkylated or N-arylated compound which has a basic skeleton of the formula VI and is obtained after step ca), or the analogous compound in which the nitrogen atom is substituted by an $R^{12}$ radical, is preferably reacted with a formamide, e.g. N,N-dimethylformamide or N-methylformanilide, in the presence of $POCl_3$ and if appropriate of a Lewis acid or a Brønsted acid, e.g. $ZnCl_2$. If $R^1$ or $R^{12}$ is H, the compound of the formula VI is reacted directly in step cb) and step ca) is not required.

The preferred reaction conditions in step cb) correspond to the reaction conditions disclosed in step bb) for the preparation of the bisaldehyde of the formula VII.

The molar ratio of the N-alkylated or N-arylated compound which is obtained in step ca) or, in the case that $R^1$ or $R^{12}$ is H, of the compound of the formula VI and of the formamide is generally from 1:1 to 1:5, preferably from 1:1 to 1:2.

The molar ratio of the N-alkylated or N-arylated compound which is obtained in step ca) or, in the case that $R^1$ or $R^{12}$ is H, of the compound of the formula VI and $POCl_3$ is generally from 1:1 to 1:2, preferably from 1:1 to 1:1.5.

The molar ratio of the N-alkylated or N-arylated compound which is obtained in step ca) or, in the case that $R^1$ or $R^{12}$ is H, of the compound of the formula VI and of the Lewis acid or of the Brønsted acid is generally from 1:1 to 1:1.5, preferably from 1:1 to 1:1.2.

Step cc)

When the compounds of the formulae XIa and XIb are identical, symmetrical compounds of the formula Ic are obtained. In the case of different compounds of the formulae IXa and IXb, unsymmetrical compounds of the formula Ic are obtained.

To prepare symmetrical compounds of the formula Ic, a compound of the formula XIa or XIb is reacted with a phosphonic ester of the formula XII. The molar ratio between the aldehyde of the formula XIa or XIb and the alkylphosphonic ester of the formula XII for the preparation of symmetrical compounds of the formula Ic is generally about 2:1.

To prepare unsymmetrical compounds of the formula Ic, an aldehyde of the formula XIa (or XIb) is first reacted with a phosphonic ester of the formula XII. The molar ratio between the aldehyde of the formula XIa (or XIb) and the alkylphosphonic ester of the formula XII is generally about 1:1. The resulting compound is then reacted with an aldehyde of the formula XIb (or XIa) different from the first aldehyde to obtain unsymmetrical compounds of the formula Ic.

The reaction conditions for the reaction of the aldehydes with the alkylphosphonic esters correspond to the reaction conditions specified in step bc).

The alkylphosphonic ester of the formula XII is prepared by reacting the corresponding dichloride or dibromide of the formula XIII

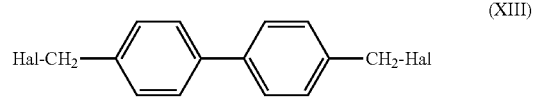

(XIII)

$Hal-CH_2-\phantom{}-\phantom{}-CH_2-Hal$ in which Hal is Cl or Br
with a trialkyl phosphite, either in substance or in a solvent such as toluene or xylene as described in U.S. Pat. No. 3,984,399.

Step cd)

To prepare the phenothiazine S,S-dioxide derivatives of the formula Ic, the phenothiazine derivatives of the formula Ic are oxidized. Suitable oxidizing agents and process conditions have already been specified above and are disclosed, for example, in M. Tosa et al. Heterocyclic Commun. 7 (2001) 277-282. It has to be taken into account that two sulfur atoms in the phenothiazine derivatives of the formula Ic are oxidized to the corresponding S,S-dioxides. Therefore, the molar ratio of the phenothiazine derivative of the formula Ic to the phenothiazine S,S-dioxide derivative of the formula Ic in which X and Y are each $SO_2$ is generally from 1:3.8 to 1:8, preferably from 1:3.9 to 1:6.

Alternatively to steps cc) and cd), the phenothiazine S,S-dioxide derivatives of the formula Ic may be obtained by steps cc') and cd') after step cb).

Step cc')

To prepare the phenothiazine S,S-dioxide derivatives, an oxidation of the aldehyde of the formula XIa and/or XIb in which X is S may be carried out. The oxidation is effected correspondingly to the process specified in step ad).

Step cd')

After step cc'), the resulting phenothiazine S,S-dioxide derivative of the formula XIa and/or XIb may be reacted with a phosphonic ester of the formula XII to obtain phenothiazine S,S-dioxide derivatives of the formula Ic. Suitable conditions and process variants of the reaction with the phosphonic ester of the formula XII correspond to the conditions and process variants specified in step cc).

d) Preparation of the Preferred Compounds of the Formula Id

The preferred compounds of the formula Id are prepared, for example, by the process which follows. 1,3-Dihalobenzene, preferably 1,3-diiodobenzene, is heated with generally from 1.8 to 2.2, preferably 2, molar equivalents of phenothiazine, phenothiazine S-oxide or phenothiazine S,S-dioxide in the presence of copper powder and alkali metal carbonate, preferably potassium carbonate, to generally 160-220° C., and kept at this temperature for 8-48 h. The reaction mixture is allowed to cool to approx. 140° C., ethyl acetate is added and the mixture is heated to boiling under reflux for about 1 h. The workup may be effected, for example, by the steps which follow. The solution is hot-filtered and, after cooling, admixed with alcohol, preferably methanol. The precipitate is filtered off with suction, dried and subsequently recrystallized.

In the aforementioned reaction, compounds of the formula Id in which X and Z have the same definition are formed. To prepare compounds of the formula Id in which X and Z have different definitions, it is possible first to react the 1,3-dihalobenzene with from 0.9 to 1.1 molar equivalents, preferably 1 molar equivalent, of phenothiazine, phenothiazine S-oxide or phenothiazine S,S-dioxide and then to react the resulting compound with from 0.9 to 1.1 molar equivalents, preferably 1 molar equivalent, of a further phenothiazine, phenothiazine S-oxide or phenothiazine S,S-dioxide different from the first phenothiazine, phenothiazine S-oxide or phenothiazine S,S-dioxide.

It is likewise possible to convert the compounds of the formula Id by reacting 1,3-difluorobenzene with generally from 1.8 to 2.2, preferably 2, molar equivalents of an NaH-deprotonated phenothiazine, phenothiazine S-oxide or phenothiazine S,S-dioxide. The workup is effected by processes known to those skilled in the art.

In the aforementioned reaction, compounds of the formula Id in which X and Z have the same definition are formed. To prepare compounds of the formula Id in which X and Z have different definitions, it is possible first to react the 1,3-difluorobenzene with from 0.9 to 1.1 molar equivalents, preferably 1 molar equivalent, of an NaH-deprotonated phenothiazine, phenothiazine S-oxide or phenothiazine S,S-dioxide and then to react the resulting compound with from 0.9 to 1.1 molar equivalents, preferably 1 molar equivalent, of a further NaH-deprotonated phenothiazine, phenothiazine S-oxide or phenothiazine S,S-dioxide different from the first deprotonated phenothiazine, phenothiazine S-oxide or phenothiazine S,S-dioxide.

e) Preparation of the Preferred Compounds of the Formula Ie

The preferred compounds of the formula Ie are prepared, for example, by the process which follows. 1,4-Dihalobenzene, preferably 1,4-diiodobenzene, is heated with generally from 1.8 to 2.2, preferably 2, molar equivalents of phenothiazine, phenothiazine S-oxide or phenothiazine S,S-dioxide in the presence of copper powder and alkali metal carbonate, preferably potassium carbonate, to generally 160-220° C. and kept at this temperature for 8-48 h. The reaction mixture is allowed to cool to approx. 100° C., hot water is added and the mixture is heated to boiling under reflux for about 1 h. The workup may be effected, for example, by the steps which follow. The solution is hot-filtered. The residue is dried and subsequently heated to boiling under reflux in methylene chloride for about 1 h. After cooling to room temperature, the suspension is filtered. The filtrate is chromatographed on silica gel in methylene chloride.

In the aforementioned reaction, correspondingly to the preparation of the compounds of the formula Id, compounds of the formula Ie in which X and Z have the same definition are formed. To prepare compounds of the formula Ie in which X and Z have different definitions, it is possible first to react the 1,4-dihalobenzene with from 0.9 to 1.1 molar equivalents, preferably 1 molar equivalent, of phenothiazine, phenothiazine S-oxide or phenothiazine S,S-dioxide and then to react the resulting compound with from 0.9 to 1.1 molar equivalents, preferably 1 molar equivalent, of a further phenothiazine, phenothiazine S-oxide or phenothiazine S,S-dioxide different from the first phenothiazine, phenothiazine S-oxide or phenothiazine S,S-dioxide.

It is likewise possible to convert the compounds of the formula Ie by reacting 1,4-difluorobenzene with an NaH-deprotonated phenothiazine, phenothiazine S-oxide or phenothiazine S,S-dioxide. Symmetrical (X and Z have the same definition) and unsymmetrical compounds of the formula Ie can be prepared correspondingly to the preparation of compounds of the formula Id.

j) Preparation of the Preferred Compounds of the Formula If

The compound of the formula If can be obtained in a corresponding manner to the compound of the formula Ie.

g) Preparation of the Preferred Compounds of the Formula Ig

The preferred compounds of the formula Ig are prepared, for example, by the process which follows: reaction of 1,3,5-trifluorobenzene with generally from 2.8 to 3.2, preferably 3, molar equivalents of an NaH-deprotonated phenothiazine, phenothiazine S-oxide or phenothiazine S,S-dioxide. The workup is effected by processes known to those skilled in the art.

In the aforementioned reaction, compounds of the formula Ig in which X, Z and Q each have the same definition are formed. Compounds of the formula Ig in which X, Z and Q have different definitions may be effected by sequentially reacting the 1,3-trifluorobenzene with different NaH-deprotonated phenothiazines, phenothiazine S-oxides or phenothiazine S,S-dioxides.

The phenoxazine, phenothiazine, phenothiazine S-oxide or phenothiazine S,S-dioxide derivatives of the formula I used in accordance with the invention are suitable for use in OLEDs. They are used as emitter substances in OLEDs since they exhibit luminescence (electroluminescence) in the visible region of the electromagnetic spectrum, preferably in the blue region of the electromagnetic spectrum. In the context of the present application, electroluminescence refers both to electrofluorescence and to electrophosphorescence. In a further embodiment of the present invention, the compounds of the formula I are used as hole or exciton blockers in OLEDs.

The aforementioned compounds of the formula I are outstandingly suitable for use as emitter substances or hole or exciton blockers in organic light-emitting diodes (OLEDs). The present invention therefore further provides organic light-emitting diodes comprising a light-emitting layer comprising or consisting of at least one emitter substance of the formula I. Preferred phenoxazine, phenothiazine, phenothiazine S-oxide or phenothiazine S,S-dioxide derivatives of the formula I have already been specified above. The present invention further provides organic light-emitting diodes comprising a blocking layer for holes and excitons, comprising or consisting of at least one compound of the formula I. Preferred compounds of the formula I are mentioned above.

Organic light-emitting diodes (OLEDs) are in principle formed from a plurality of layers, for example:
1. Anode
2. Hole-transporting layer
3. Light-emitting layer
4. Electron-transporting layer
5. Cathode Layer sequences which differ from the above-specified structure and are known to those skilled the art are also possible. For example, it is possible that the OLED does not have all of the layers mentioned; for example an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5) or the layers (1), (3), (4) and (5) are likewise suitable.

The phenoxazine, phenothiazine, phenothiazine S-oxide or phenothiazine S,S-dioxide derivatives of the formula I are used as emitter molecules in the light-emitting layer. The present application therefore further provides a light-emitting layer comprising at least one emitter substance of the formula I according to the present application.

The present invention further provides an organic light-emitting diode (OLED) comprising a blocking layer for holes and excitons, the blocking layer for holes and excitons comprising at least one compound of the formula I.

The phenoxazine, phenothiazine, phenothiazine S-oxide or phenothiazine S,S-dioxide derivatives of the formula I used in accordance with the invention may be present in the light-emitting layer in substance without further additives. However, it is likewise possible that, in addition to the phenoxazine, phenothiazine, phenothiazine S-oxide or phenothiazine S,S-dioxide derivatives of the formula I used in accordance with the invention, further compounds are present in the light-emitting layer. For example, a fluorescent dye may be present in order to change the emission color of the compound of the formula I used as an emitter molecule. In addition, a diluent material may be present. This diluent material may be a polymer, for example poly(N-vinylcarbazole) or polysilane. However, the diluent material may likewise be a small molecule, for example 4,4'-N,N'-dicarbazolebiphenyl (CBP=CDP) or tertiary aromatic amines. When a diluent material is used, the proportion of the phenoxazine, phenothiazine, phenothiazine S-oxide or phenothiazine S,S-dioxide derivatives of the formula I used in accordance with the invention in the light-emitting layer is generally less than 20% by weight, preferably from 0.5 to 10% by weight. In one embodiment of the present invention, the phenoxazine, phenothiazine, phenothiazine S-oxide or phenothiazine S,S-dioxide derivatives of the formula I used in accordance with the invention are used in substance, which avoids costly and inconvenient coevaporation of the compounds of the formula I with a matrix material (diluent material or fluorescent dye). For this purpose, it is essential that the phenoxazine, phenothiazine, phenothiazine S-oxide or phenothiazine S,S-dioxide derivatives of the formula I luminesce in the solid state. The compounds of the formula I used in accordance with the invention exhibit luminescence in the solid state. Thus, the light-emitting layer comprises, in one embodiment, at least one phenoxazine, phenothiazine, phenothiazine S-oxide or phenothiazine S,S-dioxide derivative of the formula I and no matrix material selected from diluent material and fluorescent dye. Particular preference is given to a light-emitting layer consisting of one or more emitter substances of the formula I.

The individual aforementioned layers of the OLED may in turn be composed of 2 or more layers. For example, the hole-transporting layer may be composed of one layer into which holes are injected from the electrode and one layer which transports the holes from the hole-injecting layer away into the light-emitting layer. The electron-transporting layer may likewise consist of a plurality of layers, for example one layer in which electrons are injected by the electrode and one layer which receives electrons from the electron-injecting layer and transports them into the light-emitting layer. These layers are each selected according to factors such as energy level, thermal resistance and charge carrier mobility, and also energy differential of the layers mentioned with the organic layers or the metal electrodes. Those skilled in the art are capable of selecting the structure of the OLED in such a way that it is adapted optimally to the organic compounds used as emitter substances in accordance with the invention.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer should be aligned to the work function of the cathode.

The present application further provides an OLED comprising at least one inventive light-emitting layer comprising or consisting of one of more emitter substances of the formula I. The further layers in the OLED may be composed of any material which is typically used in such layers and is known to those skilled in the art.

The anode (1) is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals include the metals of groups Ib, IVa, Va and VIa of the Periodic Table of the Elements, and also the transition metals of group VIM. When the anode is to be transparent, mixed metal oxides of groups IIb, IIIb and IVb of the Periodic Table of the Elements (old IUPAC version) are generally used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed.

Suitable hole-transporting materials for the layer (2) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole-transporting material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis [(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), α-phenyl-4-N,N-diphenylamino-styrene (TPS), p-(diethylamino)benzaldehyde diphenylhydrazone (DEH), triphenylamine (TPA), bis[4-(N,N-diethylamino)-2-methylphenyl)] (4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4',4',4"-tris(N,N-diphenylamino)triphenylamine (TDTA) and porphyrin compounds, and also phthalocyanines such as copper phthalocyanines. Customarily used hole-transporting polymers are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

Suitable electron-transporting materials for the layer (4) of the inventive OLEDs include metals chelated with oxinoid compounds, such as tris(8-quinolinolato)-aluminum (Alq3), compounds based on phenanthroline such as 2,9-dimethyl-4,7-diphenyl-1,10-phenanthroline (DDPA=BCP) or 4,7-diphenyl-1,10-phenanthroline (DPA) and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). The layer (4) may serve both to ease the electron transport and as a buffer layer or as a barrier layer in order to prevent quenching of the exciton at the interfaces of the layers of the OLED. The layer (4) preferably improves the mobility of the electrons and reduces quenching of the exciton.

Of the materials specified above as hole-transporting materials and electron-transporting materials, some can fulfill a plurality of functions. For example, some of the electron-conducting materials are simultaneously hole-blocking materials when they have a low-lying HOMO.

The charge transport layers may also be electronically doped in order to improve the transport properties of the materials used, in order firstly to make the layer thicknesses more generous (avoidance of pinholes/short circuits) and secondly to minimize the operating voltage of the device. For example, the hole-transporting materials may be doped with electron acceptors; for example, phthalocyanines or arylamines such as TPD or TDTA may be doped with tetrafluorotetracyanoquinodimethane (F4-TCNQ). The electron-transporting materials may, for example, be doped with alkali metals, for example $Alq_3$ with lithium. Electronic doping is known to those skilled in the art and is disclosed, for example, in W. Gao, A. Kahn, J. Appl. Phys., Vol. 94, No. 1, Jul. 1, 2003 (p-doped organic layers); A. G. Werner, F. Li, K. Harada, M. Pfeiffer, T. Fritz, K. Leo, Appl. Phys. Lett., Vol. 82, No. 25, Jun. 23, 2003 and Pfeiffer et al., Organic Electronics 2003, 4, 89-103.

The cathode (5) is an electrode which serves to introduce electrons or negative charge carriers. The cathode may be any metal or nonmetal that has a lower work function than the anode. Suitable materials for the cathode are selected from the group consisting of alkali metals of group Ia, for example Li, Cs, alkaline earth metals of group IIa, metals of group IIb of the Periodic Table of the Elements (old IUPAC version), including the rare earth metals and the lanthanides and actinides. In addition, metals such as aluminum, indium, calcium, barium, samarium and magnesium, and combinations thereof, may also be used. In addition, lithium-containing organometallic compounds or LiF may be applied between the organic layer and the cathode in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to layers (1) to (5), comprises at least one of the further layers mentioned below:
  a hole injection layer between the anode (1) and the hole-transporting layer (2);
  a blocking layer for electrons between the hole-transporting layer (2) and the light-emitting layer (3);
  a blocking layer for holes between the light-emitting layer (3) and the electron-transporting layer (4);
  an electron injection layer between the electron-transporting layer (4) and the cathode (5).

However, it is also possible that the OLED does not have all of the layers (1) to (5) specified; for example, an OLED having the layers (1) (anode), (3) (light-emitting layer) and (5) (cathode) is likewise suitable, in which case the functions of the layers (2) (hole-transporting layer) and (4) (electron-transporting layer) are assumed by the adjacent layers. OLEDs which have the layers (1), (2), (3) and (5) or the layers (1), (3), (4) and (5) are likewise suitable.

Those skilled in the art know how suitable materials have to be selected (for example on the basis of electrochemical investigations). Suitable materials for the individual layers are known to those skilled in the art and disclosed, for example, in WO 00/70655.

Furthermore, each of the specified layers of the inventive OLED may be composed of two or more layers. In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the inventive OLED is produced by successive vapor deposition of the individual layers onto a suitable substrate. Suitable substrates are, for example, glass or polymer films. For the vapor deposition, customary techniques may be used, such as thermal evaporation, chemical vapor deposition and others. In an alternative process, the organic layers may be coated from solutions or dispersions in suitable solvents, in which case coating techniques known to those skilled in the art are employed.

In general, the different layers have the following thicknesses: anode (1) from 500 to 5000 Å, preferably from 1000 to 2000 Å; hole-transporting layer (2) from 50 to 1000 Å, preferably from 200 to 800 Å; light-emitting layer (3) from 10 to 1000 Å, preferably from 100 to 800 Å; electron-transporting layer (4) from 50 to 1000 Å, preferably from 200 to 800 Å; cathode (5) from 200 to 10 000 Å, preferably from 300 to 5000 Å. The position of the recombination zone of holes and electrons in the inventive OLED and thus the emission spectrum of the OLED may be influenced by the relative thickness of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

Use of the phenoxazine, phenothiazine, phenothiazine S-oxide or phenothiazine S,S-dioxide derivatives of the formula I used in accordance with the invention in the light-emitting layer of the inventive OLEDs allows OLEDs having a high efficiency to be obtained. The efficiency of the inventive OLEDs may additionally be improved by optimizing the other layers. For example, highly efficient cathodes such as Ca, Ba or LiF may be used. Shaped substrates and novel hole-transporting materials which bring about a reduction in the operating voltage or an increase in the quantum efficiency are likewise usable in the inventive OLEDs. Furthermore, additional layers may be present in the OLEDs in order to adjust the energy level of the different layers and to ease electroluminescence. In addition, the phenoxazine derivatives, phenothiazine derivatives, phenothiazine S-oxide or phenothiazine S,S-dioxide derivatives of the formula used in accordance with the invention are suitable as hole and exciton blockers and can be used in accordance with the invention in the hole- and exciton-blocking layer of an OLED.

The inventive OLEDs may be used in all devices in which electroluminescence is useful. Suitable devices are preferably selected from stationary and mobile visual display units (VDUs). Stationary VDUs are, for example, VDUs of computers, televisions, VDUs in printers, kitchen appliances and advertising panels, illuminations and information panels. Mobile VDUs are, for example, VDUs in mobile telephones, laptops, digital cameras, vehicles and destination displays on buses and trains.

In addition, the phenoxazine, phenothiazine, phenothiazine S-oxide or phenothiazine S,S-dioxide derivatives of the formula I used in accordance with the invention may be used in OLEDs having inverse structure. In these inverse OLEDs, preference is given to using the compounds of the formula I used in accordance with the invention again in the light-emitting layer, more preferably as the light-emitting layer without any further additives, or in the hole- and exciton-blocking layer. The structure of inverse OLEDs and the materials customarily used therein are known to those skilled in the art.

The present invention further provides phenothiazine S,S-dioxide derivatives selected from the group consisting of compounds of the formulae XIV, XV, XVI, XVII, XVIII, XIX, XX, XXI and XXII

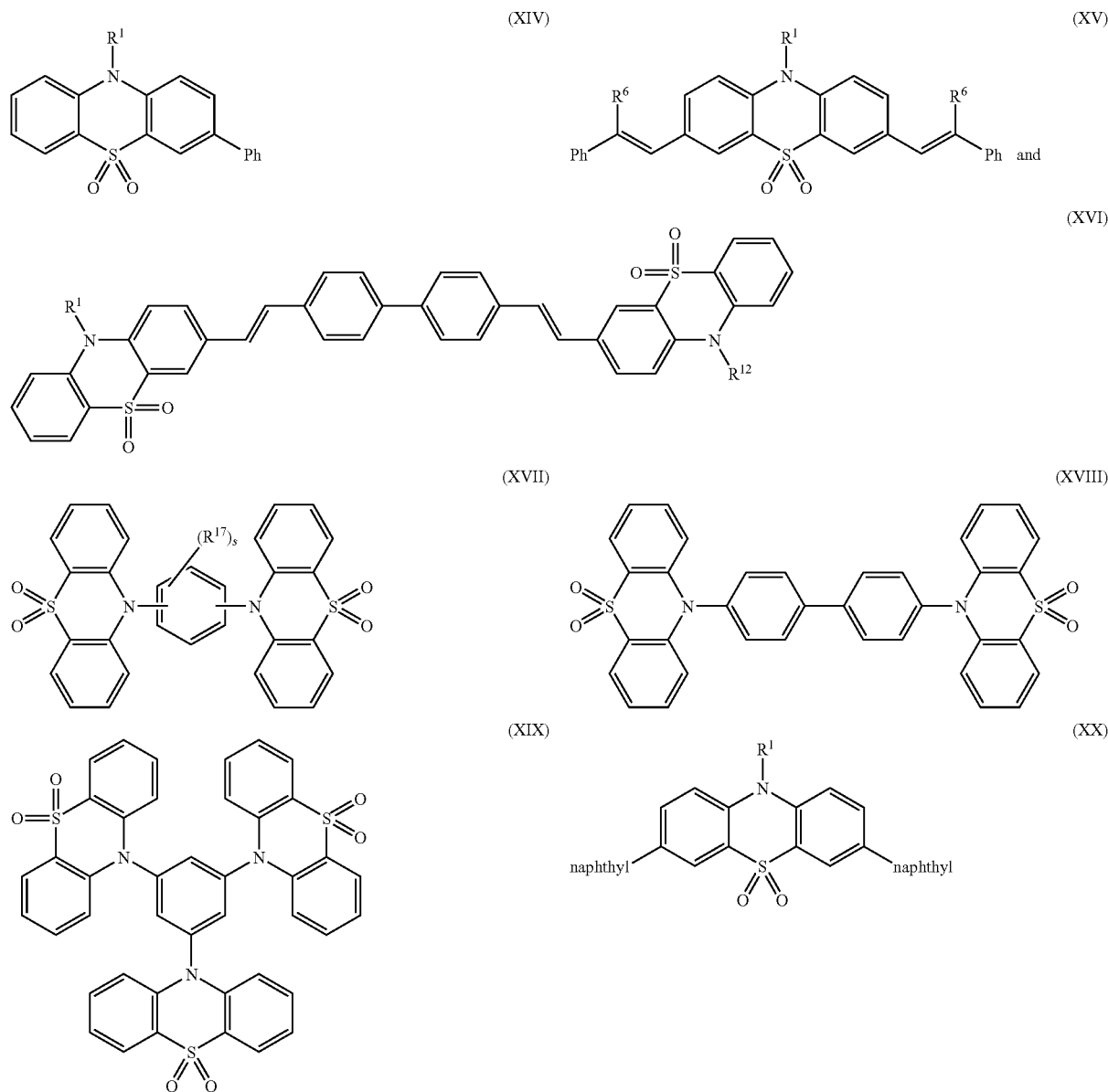

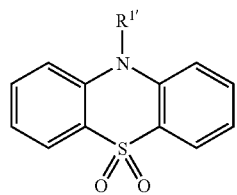
(XXI)

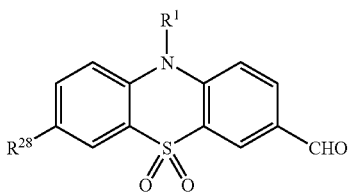
(XXII)

in which:
R$^1$, R$^{12}$ are each H, Me, Et or unsubstituted phenyl;
R$^1$ is 4-methoxyphenyl or mesityl;
R$^6$ is Me or unsubstituted phenyl;
R$^{17}$ is methoxy;
s is 0 or 2, where the substituents, in the case that s=2, are preferably arranged in the 2- and the 5-position;

Ph is unsubstituted phenyl;
naphthyl is 1- or 2-naphthyl; and
R$^{28}$ is H or —CHO
and
phenothiazine derivatives selected from the group consisting of compounds of the formulae XXIII, XXIV, XXV, XXVI, XXVII, XXVIII and XXIX

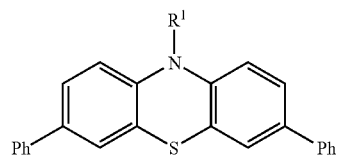
(XXIII)

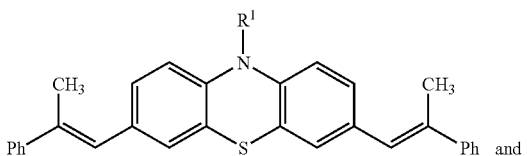
(XXIV)

and

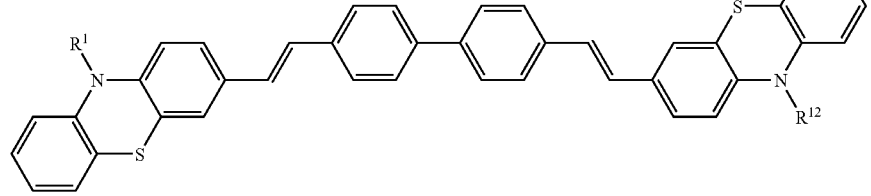
(XXV)

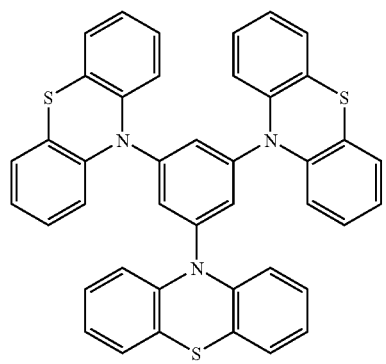
(XXVI)

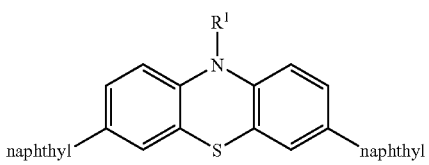
(XXVII)

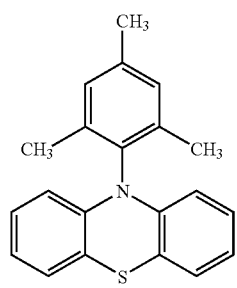
(XXVIII)

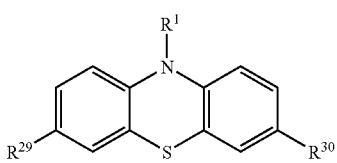
(XXIX)

in which:
$R^1$, $R^{12}$ are each H, Me, Et or unsubstituted phenyl;
Ph is unsubstituted phenyl;
naphthyl is 1- or 2-naphthyl; and
$R^{29}$, $R^{30}$ are each —CHO or

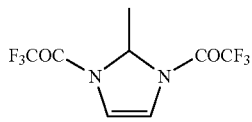

and
phenothiazine S-oxide derivatives of the formula XXX

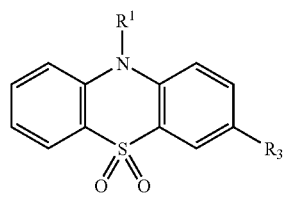

(XXX)

in which:
$R^1$ is H, Me, Et or unsubstituted phenyl; and
naphthyl is 1- or 2-naphthyl.

The present invention further provides phenothiazine S,S-dioxide derivatives selected from the group consisting of compounds of the formulae XXXI and XXXII and phenothiazine derivatives of the formula XXXIII

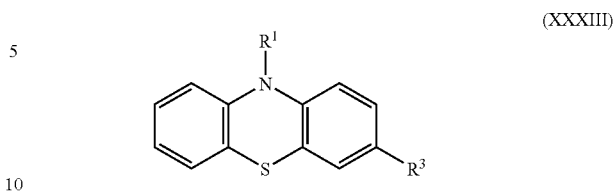

(XXXIII)

in which
$R^1$ is phenyl or pyridyl substituted by one OH, OC(O)Ph, OCH$_2$Ph or N-phenylbenzimidazolyl group, three CH$_3$ groups or two F radicals; preferably 2-hydroxyphenyl, 4-hydroxyphenyl, 2-benzoyloxyphenyl, 4-benzoyloxyphenyl, 3,5-difluorophenyl, mesitylenyl, 4-(2'-N-phenyl-benzimidazolyl)phenyl, 4-methoxyphenyl, 2-thienyl, 2-pyridyl,
$R^3$ is H or CHO, preferably H.

The aforementioned phenothiazine S,S-dioxide derivatives of the formulae XIV, XV, XVI, XVII, XVIII, XIX, XX, XXI and XXII and XXXI, XXXII and phenothiazine derivatives of the formulae XXIII, XXIV, XXV, XXVI, XXVII, XXVIII and XXIX and XXXIII, and the phenothiazine S-oxide derivatives of the formula XXX are particularly suitable for use in OLEDs, and the phenothiazine S,S-dioxide derivatives of the formula XXII and the phenothiazine derivatives of the formula XXIX are suitable especially as intermediates for preparing the inventive phenothiazine S,S-dioxide and phenothiazine derivatives. The inventive compounds of the formulae XIV, XV, XVI, XVII, XVIII, XIX, XX, XXI, XXII, XXIII, XXIV, XXV, XXVI, XXVII, XXVIII, XXIX and XXX and XXXI, XXXII and XXXIII are especially suitable as charge transport materials or emitter substances which

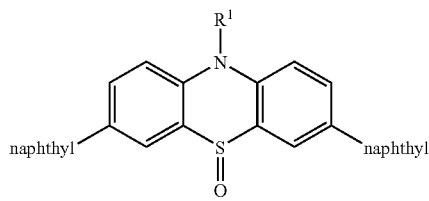

(XXXI)

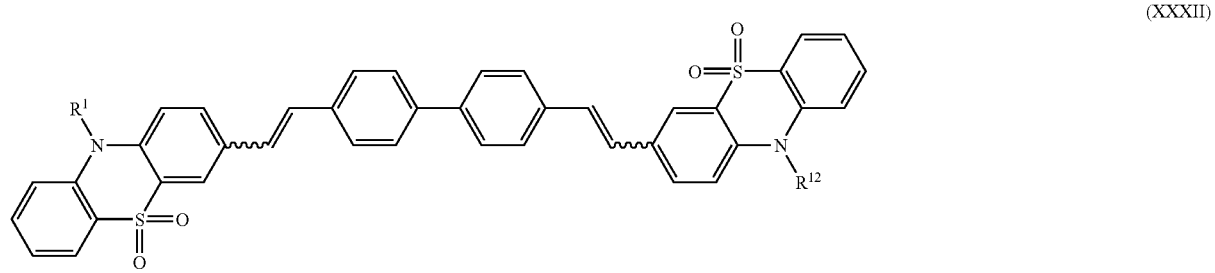

(XXXII)

in which
$R^1$ is phenyl or pyridyl substituted by one OH, OC(O)Ph, OCH$_2$Ph or N-phenylbenzimidazolyl group, three CH$_3$ groups or two F radicals; preferably 2-hydroxyphenyl, 4-hydroxyphenyl, 2-benzoyloxyphenyl, 4-benzoyloxyphenyl, 4-benzyloxyphenyl, 3,5-difluorophenyl, mesitylenyl, 4-(2'-N-phenyl-benzimidazolyl)phenyl, 4-methoxyphenyl, 2-thienyl, 2-pyridyl,
$R^3$ is H or CHO, preferably H,
$R^{12}$ is a phenyl substituted by three CH$_3$ groups, preferably mesitylenyl;

preferably emit light in the blue region of the electromagnetic spectrum. The inventive phenothiazine-S,S-dioxide derivatives and phenothiazine derivatives of the formulae XIV, XVII, XIX, XXI, XXII, XXIII, XXVI, XXVIII, XXIX, preferably XIV, XXI, XXII, XXIII, XXVII, XXIX and XXXI and XXXIII are particularly suitable as emitter blockers or hole blockers. In addition, the compounds of the formulae XV, XVI, XXIII, XXIV, XXV, XXVI, XXVII and XXVIII may be used as matrix materials. Preference is given to using the inventive compounds in the light-emitting layer of an OLED as emitter substances which preferably emit light in the blue region of the electromagnetic spectrum or as hole and exciton blockers. Very particular preference is given to using them as emitter substances in the light-emitting layer of an OLED or in the hole- and exciton-blocking layer.

The present application therefore further provides for the use of the inventive phenothiazine S,S-dioxide derivatives and of the inventive phenothiazine derivatives in OLEDs and an OLED comprising at least one of the inventive compounds. Preferred embodiments of suitable OLEDs and suitable materials for the individual layers of the OLEDs and for the cathode and anode are specified above.

Preference is given to using the inventive compounds in the light-emitting layer. The present application therefore further provides a light-emitting layer comprising at least one inventive phenothiazine S,S-dioxide derivative or phenothiazine derivative. The present application further provides an OLED comprising the inventive light-emitting layer. In a further preferred embodiment, the inventive compounds are used in the hole- and exciton-blocking layer. The invention therefore further provides a hole- and exciton-blocking layer comprising at least one inventive compound, and an OLED comprising the inventive hole- and exciton-blocking layer. Preferred embodiments of suitable OLEDs and suitable materials for the individual layers of the OLEDs and for the anode and cathode are specified above. Depending on the substitution pattern of the inventive compounds, the inventive compounds may fulfill different functions in the light-emitting layer or in the hole- and exciton-blocking layer. Preference is given to using the inventive compounds as emitter substances.

The inventive phenothiazine S,S-dioxide derivatives of the formulae XIV, XV, XVI, XVII, XVIII, XIX, XX, XXI and XXII and XXXI and XXXII and phenothiazine derivatives of the formulae XXIII, XXIV, XXV, XXVI, XXVII, XXVIII and XXIX and XXXIII and phenothiazine S-oxide derivatives of the formula XXX may be prepared by the above-specified processes. The corresponding processes for preparing the inventive phenothiazine S,S-dioxide derivatives of the formulae XIV, XV, XVI, XVII, XVIII, XIX, XX, XXI and XXII and the inventive phenothiazine derivatives of the formulae XXIII, XXIV, XXV, XXVI, XXVII, XXVIII and XXIX and XXXIII and phenothiazine S-oxide derivatives of the formula XXX likewise form part of the subject matter of the present application.

The examples which follow further illustrate the invention.

EXAMPLES

Example 1

3-Phenylphenothiazine 5,5-dioxide

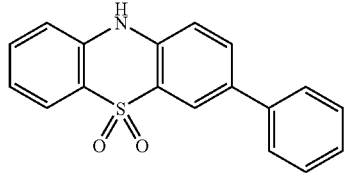

A suspension of 2.00 g (7.2 mmol) of 3-phenylphenothiazine (J. Cymerman-Craig, W. P. Rogers and G. P. Warwick, Aust. J. Chem. 1955, 8, 252-257) in 45 ml of methylene chloride was admixed at room temperature with stirring with 3.40 g (13.8 mmol) of 70% m-chloroperbenzoic acid in portions. After stirring at room temperature for 4 hours, the precipitate was filtered off, washed with methylene chloride and dried under reduced pressure. The crude product (0.95 g) was recrystallized twice from acetic acid. After the light gray solid had been dried at 100° C. under high vacuum, 0.492 g (22% of theory) of analytically pure substance having a melting point of 269-272° C. was obtained, whose solution in tetrahydrofuran fluoresced at $\lambda$=383 nm.

Example 2

10-Methyl-3,7-diphenylphenothiazine

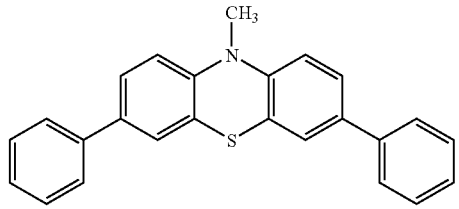

2.50 g (6.7 mmol) of 3,7-dibromo-10-methylphenothiazine (C. Bodea and M. Terdic, Acad. Rep. Rom. 1962, 13, 81-87), 1.85 g (14.9 mmol) of 98% phenylboronic acid, 0.11 g (0.14 mmol) of bis(triphenylphosphine)palladium dichloride and 1.03 g (7.4 mmol) of potassium carbonate were heated to boiling (75° C.) under reflux under nitrogen for 5 hours in 55 ml of dimethoxyethane and 28 ml of water. The reaction mixture was cooled to room temperature and stirred further overnight. The precipitate was filtered off with suction, washed successively with 125 ml of ethanol and hot water and dried at 70° C. under reduced pressure. The crude product (2.30 g) was heated to boiling under reflux in cyclohexane for two hours. After the hot suspension had been filtered, the residue was dried, dissolved in 40 ml of methylene chloride and filtered through a silica-gel-filled glass fit. After the solvent had been removed, 1.05 g (43% of theory) of light yellow, analytically pure solid having a melting point of 239-241° C. were obtained, whose solution in chloroform fluoresced at $\lambda$=464 nm.

Example 3

10-Methyl-3,7-diphenylphenothiazine 5,5-dioxide

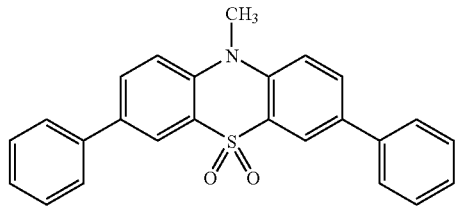

A solution of 1.95 g (5.3 mmol) of 10-methyl-3,7-diphenylphenothiazine in 65 ml of methylene chloride was admixed at room temperature with 2.67 g (10.7 mmol) of 70% m-chloroperbenzoic acid in portions and stirred at 20-25° C. for two hours. The reaction solution was subsequently extracted successively, twice in each case, with 10 ml of 10% potassium hydroxide solution, 10 ml of 5% hydrochloric acid and 10 ml of saturated sodium hydrogencarbonate solution. The organic phase was removed and purified by column chromatography (eluent: ethyl acetate). The resulting crude product (1.80 g) was recrystallized from toluene and subsequently sublimed under high vacuum. 0.65 g (31% of theory) of light beige-colored, analytically pure solid having a melting point of 242-245° C. was obtained, whose solution in chloroform fluoresced at $\lambda$=386 nm.

Example 4

10-methyl-3,7-bis(1-naphthyl)phenothiazine

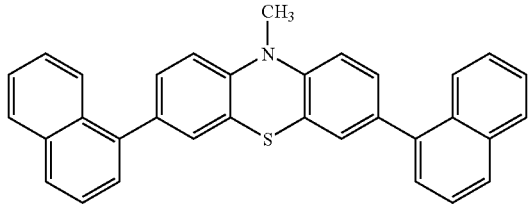

9.30 g (25.1 mmol) of 3,7-dibromo-10-methylphenothiazine, 9.50 g (55.2 mmol) of 1-naphthylboronic acid, 0.407 g (0.50 mmol) of bis(triphenylphosphane)palladium dichloride and 3.80 g (27.5 mmol) of potassium carbonate were heated to boiling under reflux under nitrogen for 5 hours in 204 ml of dimethoxyethane and 101 ml of water. The reaction mixture was cooled to room temperature, stirred further overnight and then filtered. The residue was washed with 470 ml of ethanol and hot water, and dried at 70° C. under reduced pressure. The solid was dissolved in 100 ml of methylene chloride and filtered through silica gel. After the solvent had been removed under reduced pressure, a tacky mass was obtained which, after 200 ml of methanol had been added, crystallized with stirring overnight. The crystals were filtered off with suction, washed with 300 ml of methanol and dried at 40° C. under reduced pressure. 10.33 g of light yellow microcrystals having a melting point of 185-190° C. were obtained. The crude product was recrystallized twice from ethyl acetate. 5.71 g (49% of theory) of analytically pure, almost colorless microcrystals having a melting point of 191-194° C. were obtained, whose solution in chloroform fluoresced at λ=468 nm.

Example 5

10-Methyl-3,7-bis(1-naphthyl)phenothiazine 5-oxide

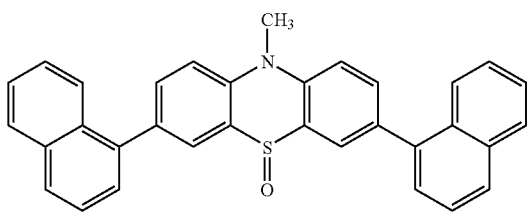

A solution of 1.20 g (5.35 mmol) of 77% m-chloroperbenzoic acid in 20 ml of methylene chloride was added dropwise to an ice-cooled suspension of 2.50 g (5.37 mmol) of 10-methyl-3,7-bis(1-naphthyl)phenothiazine in 60 ml of methylene chloride within 30 min. The reaction solution was stirred at 0-5° C. for 2 hours. Subsequently, a further 0.60 g (2.70 mmol) of m-chloroperbenzoic acid, dissolved in 10 ml of methylene chloride, was added dropwise. The solution was stirred at 0-5° C. for a further 2 hours and then warmed to room temperature. After the reaction solution had been extracted, in each case twice, with 15 ml of 10% KOH, 15 ml of 5% HCl and 25 ml of saturated sodium hydrogencarbonate solution, the organic phase was purified by column chromatography on silica gel (eluent: methylene chloride). The first fraction comprised the sulfone (see Example 6), from which 0.38 g (14% of theory) of analytically pure colorless solid having a melting point of 221-225° C. was isolated, whose solution in chloroform fluoresced at λ=385 nm. After the sulfone had been removed, the eluent was switched to ethyl acetate. After the solvent had been removed, a tacky paste was obtained which crystallized after water had been added. 1.53 g (59% of theory) of 10-methyl-3,7-bis(1-naphthyl)phenothiazine 8-oxide were obtained as an analytically pure, light brown solid having a decomposition point of >150° C., whose solution in chloroform fluoresced at λ=388 nm. 10-Methyl-3,7-bis(1-naphthyl)-phenothiazine 5,5-dioxide was obtained as a by-product.

Example 6

10-Methyl-3,7-bis(1-naphthyl)phenothiazine 5,5-dioxide

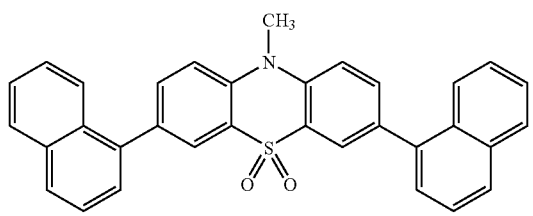

For the preparation as a by-product in the synthesis of 10-methyl-3,7-bis(1-naphthyl)phenothiazine 5-oxide, see under Example 5. For a selective preparation of the sulfone, at least two molar equivalents of m-chloroperbenzoic acid are used.

Colorless microcrystals having a melting point of 221-225° C. were obtained, whose solution in chloroform fluoresced at λ=385 nm.

Example 7

10-Methyl-3,7-bis(2-naphthyl)phenothiazine

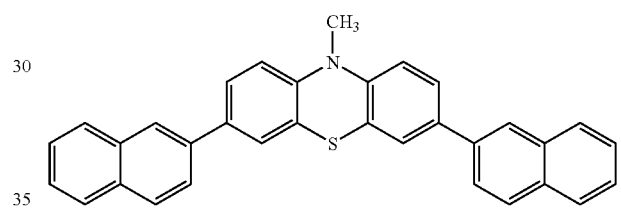

9.30 g (25.1 mmol) of 3,7-dibromo-10-methylphenothiazine, 9.50 g (55.2 mmol) of 2-naphthylboronic acid, 0.407 g (0.50 mmol) of bis(triphenylphosphine)palladium dichloride and 3.80 g (27.5 mmol) of potassium carbonate were heated to boiling under reflux under nitrogen for 5 hours in 204 ml of dimethoxyethane and 101 ml of water. The reaction mixture was cooled to room temperature, stirred further overnight and then filtered. The residue was washed with 470 ml of ethanol and hot water, and then dried at 70° C. under reduced pressure. The solid was dissolved in 200 ml of methylene chloride and filtered through silica gel. After the solvent had been removed under reduced pressure, 9.6 g of greenish-yellow solid were obtained (melting point 276-281° C.) and were recrystallized from 500 ml of toluene. 7.10 g (81% of theory) of analytically pure, shiny yellow microcrystals having a melting point of 285-289° C. were obtained, whose solution in chloroform fluoresced at λ=402 nm.

Example 8

10-Methyl-3,7-bis(2-naphthyl)phenothiazine 5-oxide

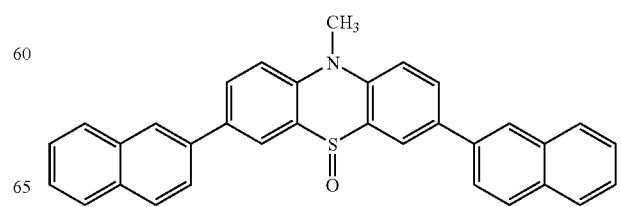

A solution of 1.20 g (5.35 mmol) of 77% m-chloroperbenzoic acid in 20 ml of methylene chloride was added dropwise to an ice-cooled suspension of 2.50 g (5.37 mmol) of 10-methyl-3,7-bis(2-naphthyl)phenothiazine in 60 ml of methylene chloride within 30 min. The reaction mixture was stirred at 0-5° C. for 2 hours. Subsequently, a further 0.60 g (2.70 mmol) of m-chloroperbenzoic acid, dissolved in 10 ml of methylene chloride, was added dropwise. The solution was stirred further at 0-5° C. for 2 hours and then warmed to room temperature. After the reaction mixture had been extracted, in each case twice, with 15 ml of 10% KOH, 15 ml of 5% HCl and 25 ml of saturated sodium hydrogencarbonate solution, the organic phase was purified by column chromatography on silica gel (eluent: methylene chloride). The first fraction comprised 0.62 g (see Example 9) which was recrystallized from 36 ml of o-dichlorobenzene. 0.44 g (16% of theory) of yellowish solid having a melting point of 328-332° C. was obtained. After the sulfone had been removed, the eluent was switched to ethyl acetate. After the solvent had been removed, 1.30 g of solid were obtained and were recrystallized from 134 ml of acetic acid. 0.54 g (21% of theory) of 10-methyl-3,7-bis(2-naphthyl)phenothiazine 5-oxide were obtained as an analytically pure beige solid having a melting point of 275-280° C., whose solution in chloroform fluoresced at λ=402 nm. 10-Methyl-3,7-bis(2-naphthyl)phenothiazine 5,5-dioxide was obtained as a by-product.

Example 9

10-Methyl-3,7-bis(2-naphthyl)phenothiazine 5,5-dioxide

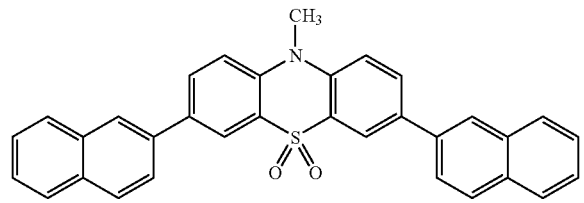

For the preparation as a by-product in the synthesis of 10-methyl-3,7-bis(2-naphthyl)phenothiazine 5-oxide, see under Example 8. For a selective preparation of the sulfone, at least two molar equivalents of m-chloroperbenzoic acid are used. Yellowish microcrystals having a melting point of 328-332° C. were obtained.

Example 10

10-Methyl-3,7-bis(2-phenylpropenyl)phenothiazine

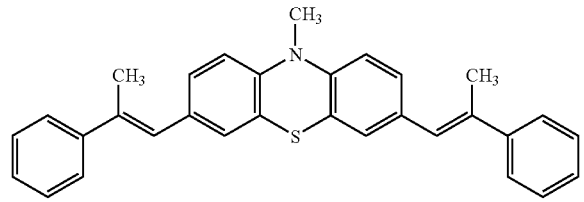

3.46 g (30.4 mmol) of potassium tert-butoxide and then 3.60 g (13.4 mmol) of 10-methylphenothiazine-3,7-dicarbaldehyde (H. Oelschläger and H. J. Peters, Arch. Pharm. (Weinheim) 320, 379-381, 1987) were added with stirring and at room temperature to a solution of 6.50 g (26.8 mmol) of diethyl (1-phenylethyl)phosphonate (Example 13 in U.S. Pat. No. 5,130,603) in 60 ml of anhydrous dimethyl sulfoxide, in the course of which the temperature rose from 25 to 41° C. After stirring at room temperature for 5 hours, the reaction solution was admixed with 150 ml of methanol, stirred for 15 min and filtered through a black band filter. The residue was washed with 300 ml of methanol and dried at 80° C. under reduced pressure. The crude product (3.6 g) was dissolved in 100 ml of methylene chloride, purified on silica gel and recrystallized from 480 ml of acetonitrile. 1.79 g (30% of theory) of analytically pure, luminous yellow microcrystals having a melting point of 189-191° C. were obtained, whose solution in chloroform fluoresced at λ=479 nm.

Example 11

10-Methyl-3,7-bis(2-phenylpropenyl)phenothiazine 5,5-dioxide

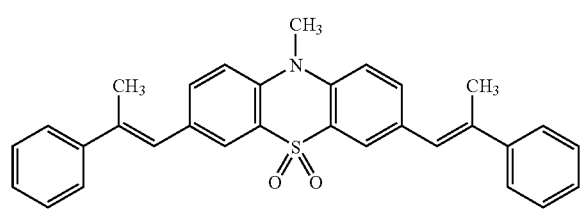

A solution of 1.70 g (3.81 mmol) of 10-methyl-3,7-bis(2-phenylpropenyl)phenothiazine in 65 ml of methylene chloride was admixed at room temperature with 1.90 g (7.60 mmol) of m-chloroperbenzoic acid in portions and stirred for a further two hours. The reaction solution was extracted, twice in each case, with 10 ml of 10% KOH, 10 ml of 5% HCl and 10 ml of saturated sodium hydrogencarbonate solution. The organic phase was diluted to 100 ml with methylene chloride and subsequently purified on silica gel, in the course of which the eluent was switched to ethyl acetate. The thus purified solid (1.00 g) was recrystallized from 40 ml of ethyl acetate. 0.57 g (31% of theory) of analytically pure colorless microcrystals having a melting point of 190-193° C. was obtained, whose solution in chloroform fluoresced at λ=394 nm.

Example 12

3,7-Bis(2,2-diphenylvinyl)-10-methylphenothiazine

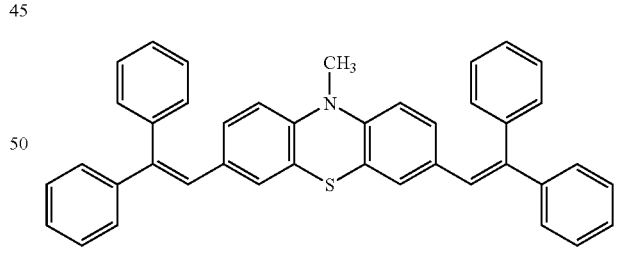

3.46 g (30.4 mmol) of potassium tert-butoxide and then 3.60 g (13.4 mmol) of 10-methylphenothiazine-3,7-dicarbaldehyde were added with stirring and at room temperature to a solution of 8.20 g (26.8 mmol) of diethyl benzhydrylphosphonate (prepared analogously to Example 13 in U.S. Pat. No. 5,130,603) in 60 ml of anhydrous dimethyl sulfoxide, in the course of which the temperature rose from 25 to 43° C. After stirring at room temperature for 5 hours, the reaction solution was admixed with 150 ml of methanol, stirred for 15 min and filtered through a black band filter. The residue was washed with 300 ml of methanol and dried at 80° C. under reduced pressure. The crude product (4.7 g) was dissolved in

Example 13

3,7-Bis(2,2-diphenylvinyl)-10-methylphenothiazine 5,5-dioxide

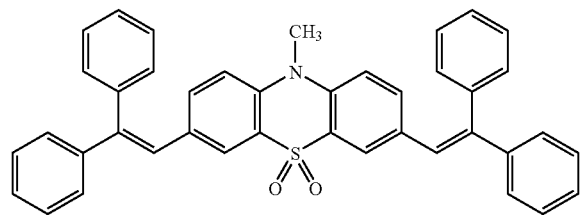

A solution of 1.80 g (3.16 mmol) of 10-methyl-3,7-bis(2-phenylpropenyl)phenothiazine in 65 ml of methylene chloride was admixed at room temperature with 1.60 g (6.5 mmol) of 70% m-chloroperbenzoic acid in portions and stirred for a further two hours. The reaction solution was extracted, twice in each case, with 10 ml of 10% KOH, 10 ml of 5% HCl and 10 ml of saturated sodium hydrogencarbonate solution. After the solvent had been removed, the solid (1.20 g) was recrystallized from 184 ml of acetic acid. 0.86 g (45% of theory) of analytically pure, almost colorless microcrystals having a melting point of 246-252° C. were obtained, which, dissolved in chloroform, fluoresced at λ=453 nm.

Example 14

3,7-Bis[1,3-bis(trifluoroacetyl)-2,3-dihydroimidazol-2-yl]-10-phenylphenothiazine

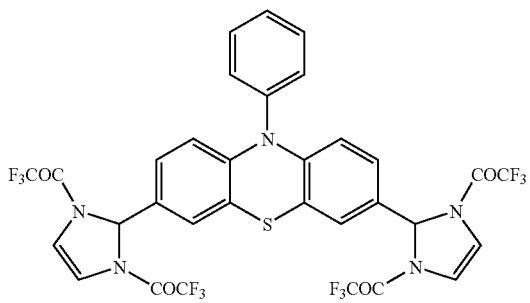

228.8 g (1.09 mol) of trifluoroacetic anhydride were added dropwise with stirring and under nitrogen within 5 min to a solution of 28.2 g (0.416 mol) of imidazole in 396 ml of anhydrous acetonitrile. After the solution had been heated to reflux temperature, 55.0 g (0.198 mol) of 10-phenylphenothiazine (J. Cymerman-Craig, W. P. Rogers and G. P. Warwick, Aust. J. Chem. 1955, 8, 252-257) were added. The solution was heated to boiling under reflux for 8 hours. Subsequently, the solvent was distilled off and the residue was admixed with ice/water and sodium carbonate. The solid was filtered off with suction and suspended in 825 ml of methanol. The suspension was sucked through a suction filter and the residue was washed twice with 50 ml each time of ether and dried under reduced pressure. 110 g of yellowish solid were obtained.

150 ml of methylene chloride, purified on silica gel and recrystallized from 83 ml of butylglycol. 3.56 g (23% of theory) of greenish microcrystals having a melting point of 233-241° C. were obtained.

Example 15

10-Phenylphenothiazine-3,7-dicarbaldehyde

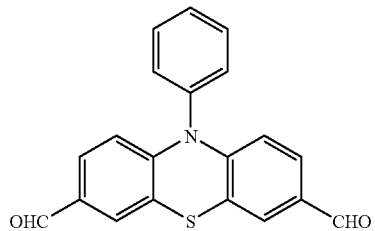

A solution of 14.0 g (17.6 mmol) of 3,7-bis[1,3-bis(trifluoroacetyl)-2,3-dihydroimidazol-2-yl]-10-phenylphenothiazine in 350 ml of acetonitrile, after 200 ml of 1.9 N HCl had been added, was heated to boiling under reflux for 3 hours. After cooling to room temperature, the suspension was filtered. After the filtrate had been concentrated, the precipitate formed was filtered off with suction, washed to neutrality with water and dried at 80° C. under reduced pressure (3.0 g of dark yellow solid). The solid was dissolved in 25 ml of methylene chloride and purified on silica gel. 1.29 g of orange solid having a melting point of 194-198° C. were obtained.

Example 16

3,7-Bis(2,2-diphenylvinyl)-10-phenylphenothiazine

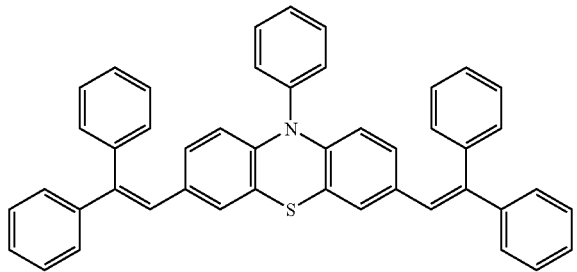

6.63 g (58.1 mmol) of potassium tert-butoxide and then 8.50 g (25.7 mmol) of 10-phenylphenothiazine-3,7-dicarbaldehyde were added at room temperature with stirring to a solution of 15.61 g (51.3 mmol) of diethyl benzhydrylphosphonate (prepared analogously to Example 13 in U.S. Pat. No. 5,130,603) in 121 ml of dimethyl sulfoxide dried over molecular sieve. After stirring at room temperature for 5 hours, the reaction solution was diluted with 1500 ml of methanol and stirred for a further 15 min. The precipitate was filtered off, washed with methanol and dried at 80° C. under reduced pressure. 6.92 g (43% of theory) of yellowish solid having a melting point of 232-237° C. were obtained.

Example 17

3,7-Bis(2,2-diphenylvinyl)-10-phenylphenothiazine 5,5-dioxide

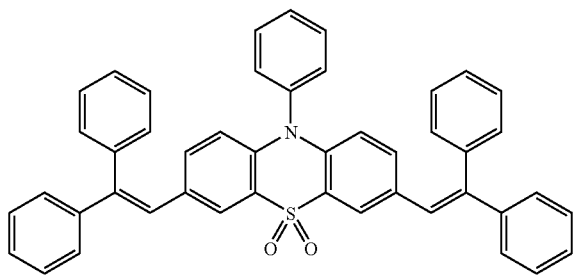

A solution of 6.85 g (10.8 mmol) of 3,7-bis(2,2-diphenylvinyl)-10-phenylphenothiazine in 250 ml of methylene chloride was admixed at room temperature with 5.84 g (20.1 mmol) of 77% m-chloroperbenzoic acid in portions and stirred for a further two hours. The reaction solution was extracted, twice in each case, with 30 ml of 10% KOH, 30 ml of 5% HCl and 30 ml of saturated sodium hydrogencarbonate solution. After the solvent had been removed, the solid (7.19 g) was dissolved in 40 ml of methylene chloride and purified on silica gel. After the solvent had been removed, 4.86 g (65% of theory) of analytically pure yellowish microcrystals having a melting point of 269-274° C. were obtained, whose solution in methylene chloride fluoresced at λ=454 nm.

Example 18

10-Methyl-3-(2-{4'-[2-(10-methylphenothiazin-3-yl)vinyl]biphenyl-4-yl}vinyl)phenothiazine

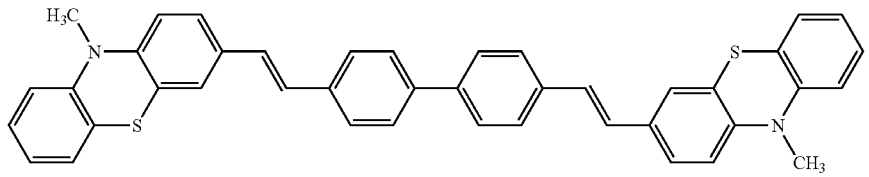

0.80 g (7.1 mmol) of potassium tert-butoxide and then 1.82 g (3.3 mmol) of 10-methylphenothiazine-3-carbaldehyde were added under nitrogen at room temperature with stirring to a solution of 1.42 g (3.14 mmol) of diethyl[4'-(diethoxyphosphoryl-methyl)biphenyl-4-ylmethyl]phosphonate (U.S. Pat. No. 3,984,399, Example 2, column 29, line 58-66) in 32 ml of dimethyl sulfoxide dried over molecular sieve. After stirring at room temperature for four hours, the reaction solution was diluted with 70 ml of methanol and stirred for a further 15 min. The precipitate was filtered off, washed with 172 ml of methanol and dried at 35° C. under reduced pressure. The crude product (1.70 g) was recrystallized in 255 ml of N-methylpyrrolidone. After the solvent residues had been removed at 225° C. under high vacuum, 0.98 g (50% of theory) of analytically pure yellow solid having a melting point of 380° C. was obtained, whose solution in N-methylpyrrolidone fluoresced at λ=576 nm.

Example 19

10-Methyl-3-(2-{4'-[2-(10-methyl-5,5-dioxophenothiazin-3-yl)-vinyl]biphenyl-4-yl}vinyl)phenothiazine 5,5-dioxide

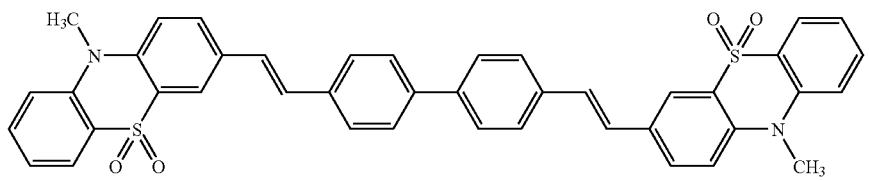

1.02 g (9.05 mmol) of potassium tert-butoxide and then 2.20 g (8.05 mmol) of 10-methyl-5,5-dioxophenothiazine-3-carbaldehyde (Example 21) were added under nitrogen at room temperature with stirring to a solution of 1.82 g (4.00 mmol) of diethyl[4'-(diethoxyphosphorylmethyl)biphenyl-4-ylmethyl]phosphonate in 41 ml of dimethyl sulfoxide dried over molecular sieve. After stirring at room temperature for four hours, the reaction solution was diluted with 90 ml of methanol and stirred for a further 15 min. The precipitate was filtered off, washed with 220 ml of methanol and dried at 35° C. under reduced pressure. The crude product (2.50 g) was recrystallized in 58 ml of dimethyl sulfoxide. After solvent residues had been removed under high vacuum at 200° C., 1.64 g (59% of theory) of analytically pure yellow solid having a melting point of 360° C. were obtained, whose solution in N-methylpyrrolidone fluoresced at λ=460 nm.

Example 20

10-Phenyl-3-(2-{4'-[2-(10-phenylphenothiazin-3-yl)vinyl]biphenyl-4-yl}vinyl)phenothiazine

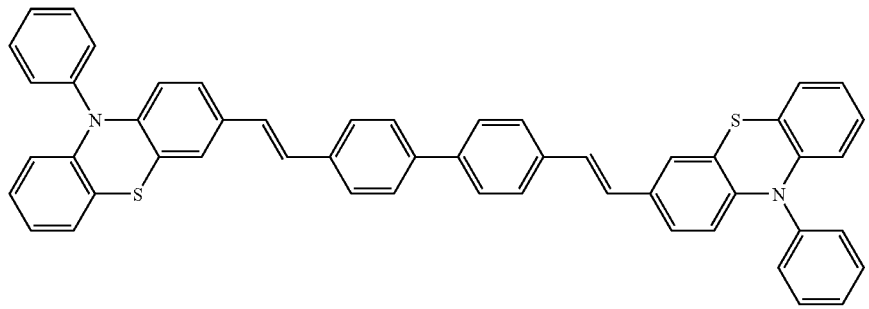

2.73 g (24.1 mmol) of potassium tert-butoxide and then 7.80 g (25.7 mmol) of 10-phenylphenothiazine-3-carbaldehyde were added under nitrogen at room temperature with stirring to a solution of 4.83 g (10.7 mmol) of diethyl[4'-(diethoxyphosphorylmethyl)biphenyl-4-ylmethyl]phosphonate in 80 ml of dimethyl sulfoxide dried over molecular sieve. After stirring at room temperature for four hours, the reaction solution was diluted with 200 ml of methanol and stirred for a further 15 min. The precipitate was filtered off, washed with 500 ml of methanol and dried at 35° C. under reduced pressure. The crude product (5.85 g) was recrystallized in 400 ml of toluene. 3.85 g of yellow solid having a melting point of 278-290° C. were obtained.

Example 21

10-Phenyl-5,5-dioxophenothiazine-3-carbaldehyde

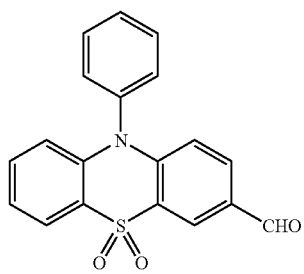

A solution of 1.01 g (3.33 mmol) of 10-phenylphenothiazine-3-carbaldehyde in 35 ml of methylene chloride was admixed at room temperature with 1.48 g (6.6 mmol) of 77% m-chloroperbenzoic acid in portions and stirred for a further two hours. The reaction solution was extracted, in each case twice, with 10 ml of 10% KOH, 10 ml of 5% HCl and 10 ml of saturated sodium hydrogencarbonate solution. After the solvent had been removed, the solid (0.87 g) was dissolved in a mixture of 19.6 ml of methylene chloride and 0.4 ml of methanol and purified on silica gel. After the solvent had been removed, 0.395 g of yellowish microcrystals having a melting point of 260-272° C. was obtained.

Example 22

10-Phenyl-3-(2-{4'-[2-(10-phenyl-5,5-dioxophenothiazin-3-yl)vinyl]-biphenyl-4-yl}vinyl)phenothiazine 5,5-dioxide

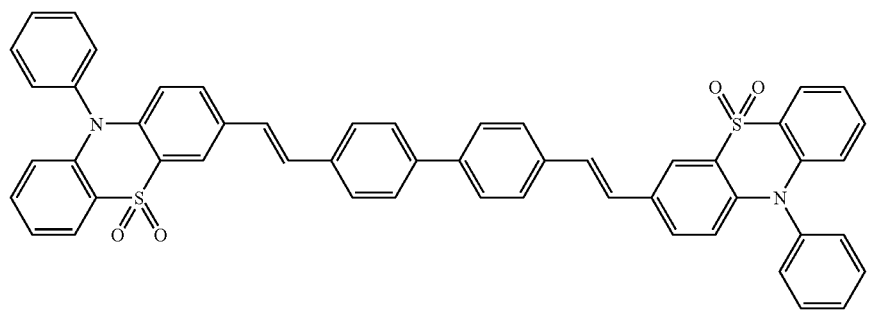

2.28 g (19.9 mmol) of potassium tert-butoxide and then 5.90 g (17.6 mmol) of 10-phenyl-5,5-dioxophenothiazine-3-carbaldehyde (Example 21) were added under nitrogen at room temperature with stirring to a solution of 4.00 g (8.80 mmol) of diethyl[4'-(diethoxyphosphorylmethyl)biphenyl-4-ylmethyl]phosphonate in 45 ml of dimethyl sulfoxide dried over molecular sieve. After stirring at room temperature for 72 h, the reaction solution was diluted with 200 ml of methanol and stirred for a further 1 h. The precipitate was filtered off, washed with 500 ml of methanol and dried at 80° C. under reduced pressure. The crude product (5.44 g) was recrystallized in 250 ml of o-dichlorobenzene. The crystals were filtered off with suction, washed successively with o-dichlorobenzene and ethanol, filtered off with suction and dried at 80° C. under reduced pressure. After solvent residues had been removed in high vacuum ($2\times10^{-5}$ mbar) at 250° C., 4.35 g (60% of theory) of yellow microcrystals having a melting point of 392° C. were obtained, whose solution in methylene chloride fluoresced at $\lambda$=456 nm.

Example 23

1,3-Phenylene-10,10% bis(phenothiazine)

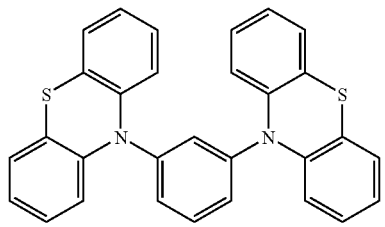

The preparation was effected according to K. Okada et al., J. Am. Chem. Soc. 1996, 118, 3047-3048.

18.5 g (91.9 mmol) of phenothiazine, 15.6 g (46.3 mmol) of 98% 1,3-diiodobenzene, 19.4 g (140 mmol) of potassium carbonate and 1.16 g (18.3 mmol) of activated copper powder were heated to 200° C. and stirred at this temperature for 24 h. The reaction mixture was cooled to 140° C. and with then admixed with 200 ml of ethyl acetate. The suspension was heated to boiling under reflux for one hour and subsequently hot-filtered. The filtrate was diluted with 300 ml of methanol, and a solid precipitated out and was filtered off with suction, washed with methanol and dried at 80° C. under reduced pressure. 8.91 g of pink solid having a melting point of 186-188° C. were obtained.

Example 24

1,3-Phenylene-10,10'-bis(phenothiazine 5,5-dioxide)

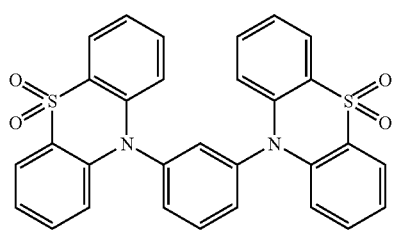

6.28 g (13.3 mmol) of 1,3-phenylene-10,10'-bis(phenothiazine) were dissolved in 220 ml of methylene chloride. After stirring at room temperature for 15 min, 17.9 g (79.9 mmol) of 77% m-chloroperbenzoic acid were added in portions. The reaction solution was stirred at room temperature for 24 h, during which a solid precipitated out. The solution was filtered, and the residue was washed with methylene chloride and suction-dried. The solid was suspended in hot water. The aqueous suspension was adjusted to pH 11 with 5% potassium hydroxide solution and subsequently hot-filtered. The residue was washed with hot water and dried at 80° C. under reduced pressure. The solid (5.07 g) was recrystallized from dimethylformamide. 3.72 g of colorless microcrystals having a melting point of 412° C. were obtained in analytically pure form, whose solution in toluene fluoresced at $\lambda$=375 nm (S).

Example 25

1,4-Phenylene-10,10'-bis(phenothiazine 5,5-dioxide)

a) 1,4-Phenylene-10,10'-bis(phenothiazine)

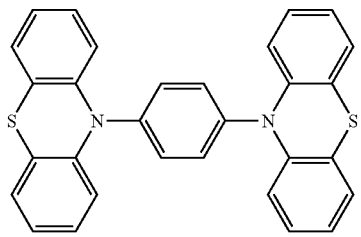

The preparation was effected according to K. Okada et al., J. Am. Chem. Soc. 1996, 118, 3047-3048.

19.9 g (98.9 mmol) of phenothiazine, 16.6 g (49.8 mmol) of 99% 1,4-diiodobenzene, 20.9 g (151 mmol) of potassium carbonate and 1.25 g (197 mmol) of activated copper powder were heated to 196° C. and stirred at this temperature for 17 h. After the reaction mixture had been cooled to room temperature, 200 ml of hot water were added. The suspension was stirred for one hour and subsequently filtered. The residue was washed with hot water and dried at 80° C. under reduced pressure. The crude product (21.6 g) was heated to boiling under reflux in 200 ml of methylene chloride for one hour. After the solution had been cooled to room temperature, it was filtered through silica gel. Three fractions were obtained, of which the first two were combined (11.7 g) and recrystallized from ethyl acetate. The third fraction contained the desired product of value (5.0 g). Overall, 13.47 g of beige solid having a melting point of 254-263° C. were obtained.

b) 1,4-Phenylene-10,10'-bis(phenothiazine 5,5-dioxide)

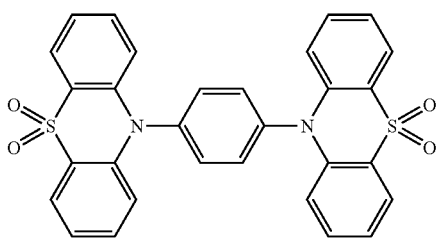

4.98 g (10.5 mmol) of 1,4-phenylene-10,10'-bis(phenothiazine) were dissolved in 175 ml of methylene chloride. After stirring at room temperature for 1 h, 10.41 g (46.5 mmol) of 77% m-chloroperbenzoic acid were added in portions. The reaction solution was stirred at room temperature for 24 h, during which a solid precipitated out. The solution was filtered, and the residue was washed with methylene chloride and suction-dried. The solid was suspended in 200 ml of hot water. The aqueous suspension was adjusted to pH 11.3 with 5 ml of 10% potassium hydroxide solution, stirred for 1 h and subsequently hot-filtered. The residue was washed with hot water and dried at 80° C. under reduced pressure. The residue (5.37 g) was recrystallized twice from sulfolane. 2.87 g (51%) of pale pink microcrystals having a melting point of >360° C. were obtained in analytically pure form, whose solution in methylene chloride fluoresced at λ=480 nm.

Example 26

10-Methylphenothiazine 5,5-dioxide

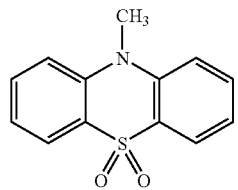

The preparation was effected according to M. Tosa et al., Heterocyclic Commun. 7 (2001) 277-282.

A solution of 10.0 g (45.9 mmol) of 98% 10-methylphenothiazine in 350 ml of methylene chloride was admixed at room temperature with 22.65 g (91.9 mmol) of 70% m-chloroperbenzoic acid and stirred at 20-25° C. for 5 h. After the solution had been filtered, the filtrate was extracted successively twice with in each case 100 ml of 10% potassium hydroxide solution, 100 ml of 5% hydrochloric acid and 70 ml of saturated sodium hydrogencarbonate. The organic phase was concentrated to 150 ml and then filtered through silica gel. From the second fraction, 4.89 g (43% of theory) of beige microcrystals having a melting point of 226-235° C. (lit. 225-226° C.) were isolated in analytically pure form. Recrystallization in acetic acid afforded colorless crystals which melted at 226-233° C. A solution of the substance in chloroform fluoresced at λ=351, 376 (S) nm.

Example 27

10-Phenylphenothiazine 5,5-dioxide a) 10-Phenylphenothiazine

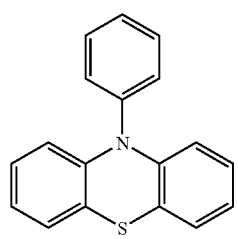

The preparation was effected according to D. Li et al., Dyes and Pigments 49 (2001) 181-186.

96.0 g (482 mmol) of phenothiazine, 298.5 g (1434 mmol) of 98% iodobenzene, 80.0 g (579 mmol) of potassium carbonate and 2.00 g (31.5 mmol) of copper powder were heated to 190-200° C. and stirred at this temperature for 6 h. Subsequently, the excess iodobenzene was distilled off. The reaction mixture was diluted with 480 ml of ethanol and heated to boiling under reflux for 1 h. The solution was hot-filtered. After cooling, the precipitate was filtered off with suction, washed with ethanol and dried under reduced pressure. 77.7 g (58.5% of theory) of gray microcrystals having a melting point of 95-96° C. (lit. 95-97° C.) were obtained.

b) 10-Phenylphenothiazine 5,5-dioxide

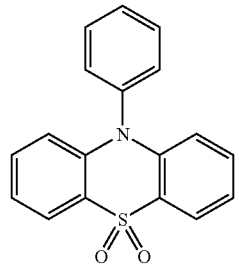

The compound known from the literature (H. Gilman and R. O. Ranck, J. Org. Chem. 1958, 23, 1903-1906) was prepared in analogy to M. Tosa et al., Heterocyclic Commun. 7 (2001) 277-282.

A solution of 5.50 g (20.0 mmol) of 10-phenylphenothiazine in 220 ml of methylene chloride was admixed at room temperature with 11.84 g (48.0 mmol) of 70% m-chloroperbenzoic acid and stirred at 20-25° C. for 8 h. The solution was concentrated to dryness. The residue was suspended in hot water and heated to 80-85° C. At this temperature, the pH was adjusted to 7-8 with 32 ml of 10% potassium hydroxide solution. The solution was stirred for a further 30 min, then filtered, washed with hot water and dried at 80° C. under reduced pressure. The crude product (5.77 g) was dissolved in 30 ml of methylene chloride and filtered through silica gel. From the second fraction, 2.92 g (47% of theory) of beige microcrystals having a melting point of 212-217° C. (lit. 212-213° C.) were isolated in analytically pure form. Recrystallization in acetic acid afforded colorless crystals which melted at 212-217° C. A solution of the substance in chloroform fluoresced at λ=348, 386 (S), 452 (S) nm.

Example 28

10-(4-Methoxyphenyl)phenothiazine 5,5-dioxide a) 10-(4-Methoxyphenyl)phenothiazine

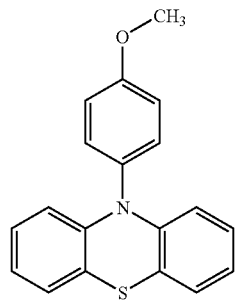

18.77 g (94.2 mmol) of phenothiazine, 66.5 g (284 mmol) of 98% 4-iodoanisole, 15.7 g (114 mmol) of potassium carbonate and 0.392 g (6.17 mmol) of copper powder were heated to 190-200° C. and stirred at this temperature for 48 h. Subsequently, the excess iodobenzene was distilled off. The reaction mixture was admixed with 200 ml of hot water and heated at 90° C. for 1 h. The solution was hot-filtered. After cooling, the precipitate was filtered off with suction, washed with ethanol and dried under reduced pressure. The crude product (29.0 g) was recrystallized from 345 ml of acetic acid. 22.54 g (78.4% of theory) of beige microcrystals having a melting point of 173-176° C. (lit. 172-174° C. (E. R. Biehl et al., J. Heterocyclic Chem. 12 (1975) 397-399)) were obtained.

b) 10-(4-Methoxyphenyl)phenothiazine 5,5-dioxide

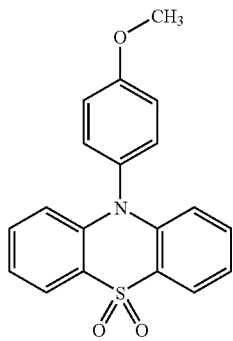

A solution of 5.00 g (16.4 mmol) of 10-(methoxyphenyl)phenothiazine in 175 ml of methylene chloride was admixed at room temperature with 9.76 g (39.6 mmol) of 70% m-chloroperbenzoic acid and stirred at 20-25° C. for 4 h. The solution was concentrated to dryness. The residue was taken up with 200 ml of hot water and dried to 80-85° C. At this temperature, the pH was adjusted to 7-8 with 25 ml of 10% potassium hydroxide solution. The solution was stirred for a further 30 min, then filtered, washed with hot water and dried at 80° C. under reduced pressure. The crude product (5.25 g) was dissolved in 70 ml of methylene chloride and filtered through silica gel. After the solvent had been removed, 4.41 g (80% of theory) of colorless microcrystals having a melting point of 265-266° C. were isolated in analytically pure form. Recrystallization in acetic acid afforded colorless crystals which melted at 264-270° C. A solution of the substance in chloroform fluoresced at λ=474 nm.

Example 29

10-Mesitylphenothiazine 5,5-dioxide a) 10-Mesitylphenothiazine

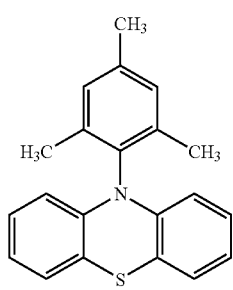

9.92 g (49.8 mmol) of phenothiazine, 25.0 g (99.6 mmol) of 98% 2,4,6-trimethyl-iodobenzene, 8.30 g (60.0 mmol) of potassium carbonate and 0.207 g (3.26 mmol) of copper powder were heated to 180° C. and stirred at this temperature for 24 h. Subsequently, the excess 2,4,6-trimethyliodobenzene was distilled off. The reaction mixture was admixed with 300 ml of water and stirred overnight. The suspension was filtered, washed to neutrality with hot water and dried at 80° C. under reduced pressure. The crude product (16.6 g) was heated to boiling under reflux in 500 ml of ethanol for 2 h and then diluted with 200 ml of water. The precipitate was filtered off with suction, dried at 80° C. under reduced pressure (10.5 g) and dissolved in 150 ml of toluene. The solution was filtered through silica gel. After the filtrate had been concentrated, 7.22 g of light brown microcrystals having a melting point of 192-200° C. were obtained.

b) 10-Mesitylphenothiazine 5,5-dioxide

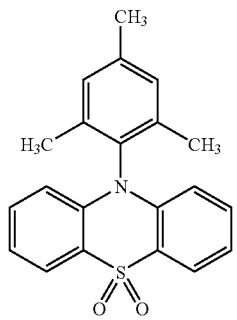

A solution of 1.50 g (4.73 mmol) of 10-mesitylphenothiazine in 55 ml of methylene chloride was admixed at room temperature with 2.80 g (11.4 mmol) of 70% m-chloroperbenzoic acid and stirred at 20-25° C. for 8 h. The solution was extracted successively twice with in each case 20 ml of 10% potassium hydroxide solution, 20 ml of 5% hydrochloric acid and 15 ml of saturated sodium hydrogencarbonate solution. The solution was filtered through silica gel. After the filtrate had been concentrated, 1.43 g (86% of theory) of beige microcrystals having a melting point of 242-246° C. were isolated in analytically pure form. Recrystallization in acetic acid afforded colorless crystals which melted at 240-246° C. A solution of the substance in chloroform fluoresced at λ=349, 370 (S) nm.

Example 30

1,3,5-Phenylene-10,10',10"-tris(phenothiazine 5,5-dioxide)

a) 1,3,5-Phenylene-10,10',10"-tris(phenothiazine)

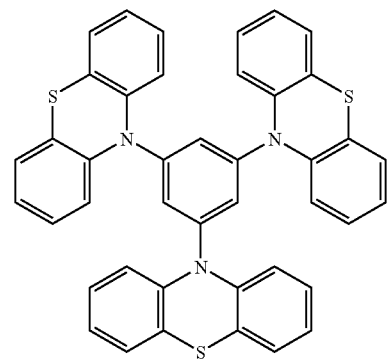

30.19 g (150 mmol) of phenothiazine were added at room temperature with stirring and under nitrogen to a suspension of 6.00 g (150 mmol) of sodium hydride (60% dispersion in paraffin oil) in 150 ml of anhydrous dimethylformamide, in the course of which the reaction temperature rose to 40° C. After the hydrogen evolution had ended (approx. 20 min), a solution of 6.20 g (46.0 mmol) of 98% 1,3,5-trifluorobenzene in 10 ml of dimethylformamide was added dropwise to the reaction solution within 15 min. Subsequently, the reaction solution was heated first at 80° C. for 2 hours, then at 100° C. for 16 hours. After cooling to room temperature, the reaction solution was precipitated in 500 ml of ice-water. The precipitate was filtered off with suction, washed to neutrality with hot water and then dispersed in 500 ml of methanol. The suspension was heated to boiling under reflux for one hour. After cooling to room temperature, the solid was filtered off with suction, washed with methanol and dried at 50° C. under reduced pressure. 24.80 g of solid were obtained which were heated to boiling under reflux in ethyl acetate for one hour. After cooling to room temperature, the solid was filtered off with suction, washed with ethyl acetate and heated to boiling under reflux once more in ethyl acetate for one hour. After cooling to room temperature, the solid was filtered off with suction, washed with ethyl acetate and dried at 80° C. under reduced pressure. 23.34 g (76% of theory) of light gray solid having a melting point of 264-268° C. were obtained.

b) 1,3,5-Phenylene-10,10',10''-tris(phenothiazine 5,5-dioxide)

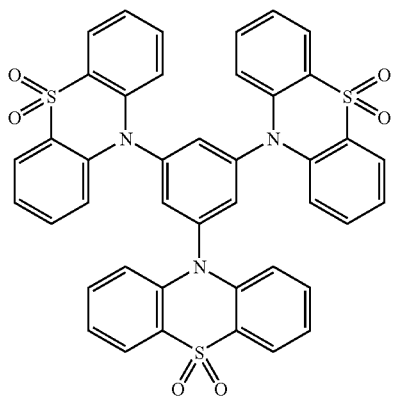

A solution of 6.70 g (10.0 mmol) of 1,3,5-phenylene-10, 10',10''-tris(phenothiazine) in 180 ml of methylene chloride was admixed at room temperature with 22.19 g (90.0 mmol) of 70% m-chloroperbenzoic acid in portions and stirred at 20-25° C. for 24 h. The reaction mixture was concentrated to dryness, then admixed with 150 ml of hot water and 46 ml of 10% potassium hydroxide solution. The solid was filtered off with suction, washed to neutrality with hot water and dried at 80° C. under reduced pressure. 7.63 g of beige microcrystals having a melting point of >360° C. were obtained.

Example 31

4-(5,5-Dioxophenothiazin-10-yl)phenyl benzoate a) 10-(2-Hydroxyphenyl)phenothiazine

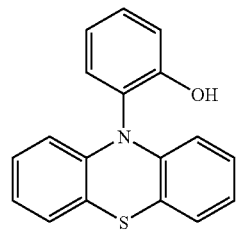

35.9 g (180 mmol) of phenothiazine, 44.5 g (198 mmol) of 98% 4-iodophenol (2-iodophenol can likewise be used), 29.9 g (216 mmol) of potassium carbonate and 0.75 g (12 mmol) of copper powder were heated to 198° C. and stirred at this temperature for 3.5 h. The reaction melt was cooled to 140° C. and then admixed with 150 ml of water within 3 min, in the course of which the reaction mixture solidified. After cooling with dry ice, the solid was isolated, comminuted in a mortar and admixed with 150 ml of water. The suspension was subjected to a steam distillation in order to remove excess iodophenol. Subsequently, the solid was filtered off with suction and washed with water. The water-moist solid was suspended in 400 ml of ethanol, dried at room temperature overnight, then filtered off with suction, washed with ethanol and dried at 80° C. under reduced pressure. The crude product (16.6 g) was heated to boiling under reflux in 500 ml of ethanol for 2 h and then diluted with 200 ml of water. The precipitate was filtered off with suction, dried at 80° C. under reduced pressure (10.5 g) and dissolved in 150 ml of toluene. The solution was filtered through silica gel. After the filtrate had been concentrated, 7.22 g of light brown microcrystals having a melting point of 192-200° C. were obtained.

b) 2-(Phenothiazin-10-yl)phenyl benzoate

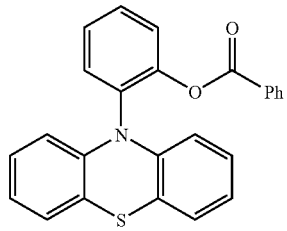

16.0 g (114 mmol) of benzoyl chloride were added dropwise at 0-5° C. with stirring to a solution of 4.00 g (13.7 mmol) of 10-(2-hydroxyphenyl)phenothiazine in 24 ml of pyridine within 30 min. After stirring at room temperature for 2 h, the reaction solution was heated to 60-65° C. and stirred at this temperature for 15 min. After cooling to room temperature, the suspension was then stirred overnight. After adding 300 ml of ice-water, the suspension was admixed slowly with 19 ml of conc. hydrochloric acid (pH 0.9) and stirred for 1 h. The suspension was filtered through a glass frit. The residue was washed to neutrality with 2 l of water and dried at 60° C. under reduced pressure. 2.87 g (53% of theory) of colorless microcrystals having a melting point of 144-148° C. were obtained.

c) 2-(5,5-Dioxophenothiazin-10-yl)phenyl benzoate

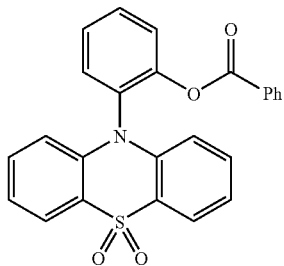

A solution of 1.32 g (3.33 mmol) of 2-(phenothiazin-10-yl)phenyl benzoate in 50 ml of methylene chloride was admixed at room temperature with 1.81 g (7.33 mmol) of 70% m-chloroperbenzoic acid and stirred at 20° C. for 24 h. The solution was concentrated to dryness under reduced pressure. The residue was taken up in 50 ml of water. The suspension was heated to 80° C. and, after adding 4.5 ml of 10% potassium hydroxide solution, stirred for 20 min. The beige solid was filtered off with suction while hot, washed with hot water and dried at 70° C. (1.285 g). A solution of the solid in 22 ml of methylene chloride was filtered through MN 60 silica gel, which was subsequently washed with a mixture of 100 parts of methylene chloride and 1 part of methanol. After the filtrate had been concentrated, the residue was recrystallized from acetic acid. 0.93 g (65% of theory) of colorless microcrystals was obtained, which melted at 228-232° C.

Example 32

10-(2-Hydroxyphenyl)phenothiazine 5,5-dioxide

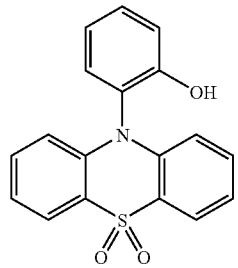

A solution of 1.50 g (5.14 mmol) of 10-(2-hydroxyphenyl)phenothiazine in 50 ml of methylene chloride was admixed at room temperature with 2.79 g (11.31 mmol) of 70% m-chloroperbenzoic acid and stirred at room temperature for 5.5 h. The solution was concentrated to dryness under reduced pressure. The residue was taken up in 100 ml of water. The suspension was heated to 80° C. and, after adding 7.5 ml of 10% potassium hydroxide solution, stirred for 20 min. The solid was filtered off with suction while hot, washed with hot water and dried at 70° C. (1.45 g). The beige solid was recrystallized twice from 42 ml of acetic acid each time. 0.92 g (55% of theory) of colorless microcrystals were obtained, which melted at 282-287° C.

Example 33

4-(5,5-Dioxophenothiazin-10-yl)phenyl benzoate a) 4-Iodophenyl benzyl ether

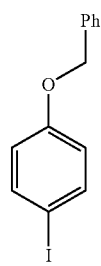

A reaction mixture composed of 21.40 g (95.3 mmol) of 98% 4-iodophenol, 12.19 g (95.3 mmol) of 99% benzyl chloride, 20.73 g (150 mmol) of potassium carbonate and 250 ml of acetone was heated to reflux temperature and heated to boiling for 30 hours. After cooling to room temperature, the reaction mixture was filtered. The filtrate was concentrated and then cooled in an ice bath, in the course of which a solid precipitated out. This was removed by means of a blue-band filter and then dried. The crude product (23.22 g) was recrystallized from 70 ml of ethanol. 17.20 g (58% of theory) of colorless microcrystals having an m.p. of 61-62° C. (lit. 62° C.) were obtained.

b) 10-(4-Benzyloxyphenyl)phenothiazine

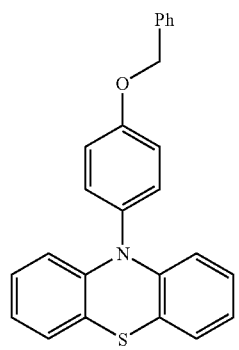

5.56 g (27.9 mmol) of phenothiazine, 8.65 g (27.9 mmol) of 4-iodophenyl benzyl ether, 4.64 g (33.5 mmol) of potassium carbonate and 0.116 g (1.82 mmol) of copper powder were heated to 190° C. and stirred at this temperature for 24 h. The reaction melt was cooled to 110° C., then diluted with 200 ml of toluene and stirred at 112° C. for 1 hour. The solution was hot-filtered. The filtrate cooled to room temperature was purified on silica gel in toluene. The beige crude product (6.52 g) was recrystallized from 125 ml of ethanol.

4.79 g (45% of theory) of beige microcrystals having an m.p. of 144-146° C. were obtained.

c) 10-(4-Benzyloxyphenyl)phenothiazine 5,5-dioxide

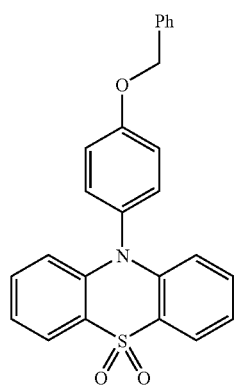

A solution of 4.60 g (12.1 mmol) of 10-(4-benzyloxyphenyl)phenothiazine in 130 ml of methylene chloride was admixed at room temperature with 6.53 g (26.5 mmol) of 70% m-chloroperbenzoic acid and stirred at room temperature for 3 h. The solution was concentrated to dryness under reduced pressure. The residue was taken up in 150 ml of water. The suspension was heated to 80° C. and, after adding 14 ml of 10% potassium hydroxide solution, stirred for 20 min. The solid was filtered off with suction while hot, washed with hot water and dried at 100° C. 4.78 g (96% of theory) of beige solid having an m.p. of 203-208° C. were obtained. In order to remove methylene chloride residues, 0.96 g of solid was sublimed at 200° C. under high vacuum. 0.78 g of analytically pure colorless microcrystals was obtained, which melted at 204-208° C.

d) 10-(4-Hydroxyphenyl)phenothiazine 5,5-dioxide

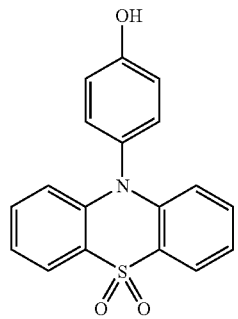

3.10 g (7.50 mmol) of 10-(4-benzyloxyphenyl)phenothiazine 5,5-dioxide, 2.30 g (35.7 mmol) of 98% ammonium formate and 7.5 g of 10% palladium on activated carbon were heated to boiling under reflux in 225 ml of acetone for 1 hour. After cooling to room temperature, the solution was filtered. The filtrate was concentrated and, after adding 10 ml of methanol, stirred overnight. The solid was filtered off with suction, washed with methanol and dried at 110° C. in a vacuum drying cabinet. 1.47 g (61% of theory) of analytically pure light gray microcrystals having an m.p. of 308-311° C. were obtained.

e) 4-(5,5-Dioxophenothiazin-10-yl)phenyl benzoate

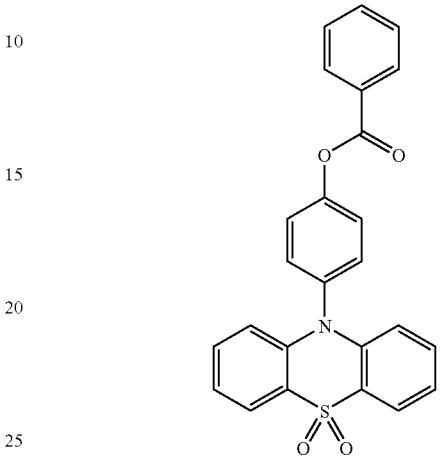

0.68 g (6.68 mmol) of triethylamine and 0.34 g (2.44 mmol) of benzoyl chloride were added to a solution of 0.72 g (2.22 mmol) of 10-(4-hydroxyphenyl)phenothiazine 5,5-dioxide in 120 ml of acetonitrile. After stirring at room temperature for 45 min, the solvent was distilled off. The residue was taken up in 100 ml of hot water and stirred at 75° C. for 30 min. The solid was filtered off with suction while hot, washed with hot water and dried at 120° C. in a forced-air drying cabinet. 0.87 g (92% of theory) of colorless microcrystals having an m.p. of 233-235° C. were obtained.

Example 34

10-(3,5-Difluorophenyl)phenothiazine 5,5-dioxide a) 10-(3,5-Difluorophenyl)phenothiazine

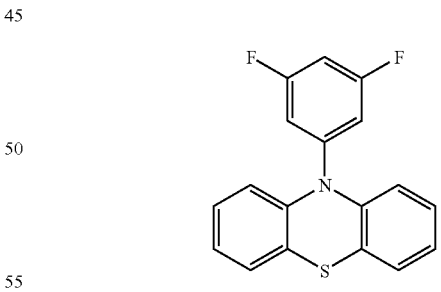

10.07 g (50.0 mmol) of phenothiazine were added at room temperature with stirring and under nitrogen to a suspension of 2.00 g (50.0 mmol) of sodium hydride (60% dispersion in paraffin oil) in 100 ml of anhydrous dimethylformamide within 10 min, in the course of which the reaction temperature rose to 32° C. After the end of hydrogen evolution (approx. 20 min), a solution of 7.41 g (55.0 mmol) of 98% 1,3,5-trifluorobenzene in 50 ml of dimethylformamide was added dropwise to the reaction solution heated to 85° C. within 15 min. Subsequently, the reaction solution was stirred at this temperature for 24 hours. After cooling to room temperature, the reaction solution was precipitated slowly in 500 ml of ice-water. After addition of 18 g of sodium chloride, the aqueous suspension was stirred for 2 h and then filtered. The residue was washed with water and dried. The solid was suspended in 200 ml of hexane and heated under reflux for 1 h. After cooling to room temperature, the suspension was filtered. The filtrate was concentrated to dryness under reduced pressure. The residue (7.00 g) was stirred in 230 ml of mixture of 40 parts of hexane and 1 part of ethyl acetate and filtered. The filtrate was chromatographed on silica gel with an eluent composed of 40 parts of hexane and 1 part of ethyl acetate. After the solvent had been removed, the residue was dried at 80° C. and 1.8×10$^{-5}$ mbar, in the course of which some of the substance sublimed. The solid which remained in the vessel was recrystallized from 40 ml of ethanol. 1.18 g (7.6% of theory) of analytically pure colorless microcrystals having a melting point of 111-115° C. were obtained.

b) 10-(3,5-Difluorophenyl)phenothiazine 5,5-dioxide

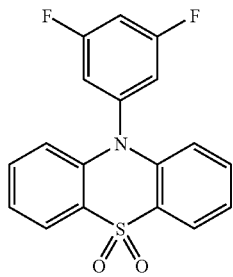

A solution of 1.40 g (4.50 mmol) of 10-(3,5-difluorophenyl)phenothiazine in 40 ml of methylene chloride was admixed at room temperature with 2.46 g (10.0 mmol) of 70% m-chloroperbenzoic acid and stirred at room temperature for 2 h. The solution was concentrated to dryness under reduced pressure. The residue was stirred in 100 ml of water at 50° C. for 30 min. The suspension was admixed with 7.5 ml of 10% potassium hydroxide solution, stirred for 30 min and then filtered. The solid was filtered off with suction while hot, washed with hot water and dried at 80° C. The beige solid (1.54 g) was recrystallized twice from acetic acid. After drying at 130° C. under high vacuum, 0.73 g (47% of theory) of analytically pure colorless microcrystals were obtained, which melted at 255-258° C.

Example 35

10-(2-Pyridyl)phenothiazine 5,5-dioxide a) 10-(2-Pyridyl)phenothiazine

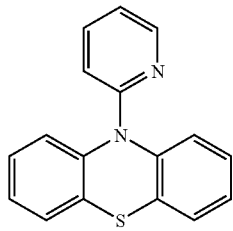

4.46 g (22.4 mmol) of phenothiazine, 9.36 g (47.6 mmol) of 98% 2-iodopyridine, 3.72 g (26.9 mmol) of potassium carbonate and 0.093 g (1.5 mmol) of copper powder were heated to 192° C. and stirred at this temperature for 24 h. The reaction melt was cooled to 100° C., then diluted slowly with 200 ml of ethanol and heated to boiling under reflux for 1 hour. After cooling to room temperature, the reaction mixture was filtered, which left a tacky paste which was dissolved in 100 ml of methylene chloride. The methylene chloride solution was purified on silica gel to obtain two fractions. The second fraction was concentrated to dryness. 2.55 g (41% of theory) of beige microcrystals having a melting point of 107-109° C. (lit.: 109-110° C.) were obtained.

b) 10-(2-Pyridyl)phenothiazine 5,5-dioxide

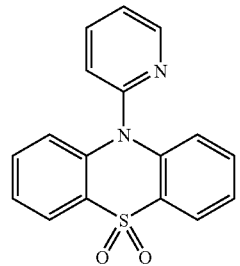

A solution of 2.20 g (7.96 mmol) of 10-(2-pyridyl)phenothiazine in 80 ml of methylene chloride was admixed at room temperature with 4.32 g (17.5 mmol) of 70% m-chloroperbenzoic acid with cooling and stirred at room temperature for 2 h. The solution was concentrated to dryness under reduced pressure. The residue was taken up in 200 ml of water at 70° C. and admixed with 10 ml of 10% KOH. After stirring for 30 min, the suspension was filtered. The residue was washed with hot water and dried at 50° C. under reduced pressure. The colorless solid (1.87 g) was dissolved in 20 ml of a mixture of 99 parts of methylene chloride and one part of methanol, and purified on silica gel. The purified solution was concentrated to dryness. After the residue had been dried at 70° C. under reduced pressure, it was recrystallized from 10 ml of acetic acid. 1.09 g (44% of theory) of analytically pure colorless microcrystals were obtained, which melted at 186-190° C. After prolonged standing of the filtrate in acetic acid at room temperature, another 0.32 g of colorless microcrystals having a melting point of 184-188° C. precipitated out (total yield: 57%).

Example 36

10-[4-(N-Phenyl-2-benzimidazolyl)phenyl]phenothiazine 5,5-dioxide a) N-Phenyl-2-(4-iodophenyl)benzimidazole

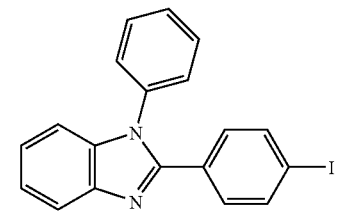

37.47 g (136 mmol) of 97% 4-iodobenzoyl chloride and 12.82 g (68.2 mmol) of 98% o-aminodiphenylamine were heated to 100° C., in the course of which a stirrable melt formed from 85-90° C. Once the gas evolution had ended (5 min), the melt solidified. The reaction mixture was kept at 100° C. for another 3 hours. After cooling, it was admixed with 100 ml of ethanol with stirring. The precipitate was filtered off with suction, washed with ethanol and stirred up again in 400 ml of ethanol. The suspension was heated to 75° C., which formed a solution which was adjusted to pH 8 with 29 ml of 25% ammonia. After cooling to 5-10° C., the precipitate was filtered off with suction, washed with cold ethanol and dried at 75° C. in a vacuum drying cabinet. 18.37 g (68% of theory) of light gray microcrystals having an m.p. of 178-181° C. were obtained.

b) 10-[4-(N-Phenyl-2-benzimidazolyl)phenyl]phenothiazine

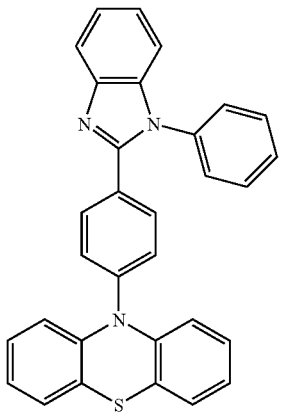

7.77 g (39.0 mmol) of phenothiazine, 17.00 g (42.9 mmol) of N-phenyl-2-(4-iodophenyl)benzimidazole, 6.47 g (46.8 mmol) of potassium carbonate and 0.162 g (2.54 mmol) of copper powder were heated to 195-200° C. and stirred at this temperature for 19 h. The reaction melt was cooled to 130° C. and then diluted with 100 ml of ethanol. After heating under reflux for 30 min, the solution was hot-filtered. The suspension was concentrated to dryness and then admixed with 150 ml of methylene chloride. After filtration, the filtrate was filtered through silica gel. 11.03 g of beige microcrystals were obtained.

c) 10-[4-(N-Phenyl-2-benzimidazolyl)phenyl]phenothiazine 5,5-dioxide

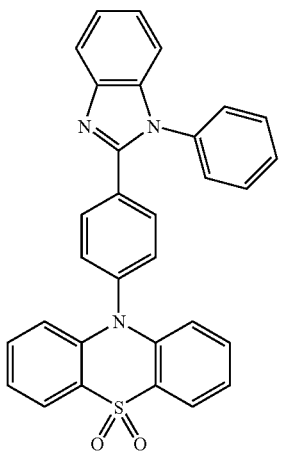

A solution of 6.14 g of 10-[4-(N-phenyl-2-benzimidazolyl)phenyl]phenothiazine in 180 ml of methylene chloride was admixed at room temperature with 7.17 g (28.9 mmol) of 70% m-chloroperbenzoic acid with cooling and stirred at room temperature for 1 h. The solution was admixed with 60 ml of 10% KOH. After the methylene chloride had been removed, the suspension was diluted with 100 ml of hot water. The precipitate was filtered off with suction, washed with hot water and dried at 80° C. under reduced pressure. The crude product (4.82 g) was recrystallized from 48 ml of acetic acid. 3.02 g (46% of theory) of beige microcrystals having an m.p. of 286-288° C. were obtained.

Example 37

10-Mesityl-3-(2-{4'-[2-(10-mesityl-5,5-dioxophenothiazin-3-yl)-vinyl]biphenyl-4-yl}vinyl)phenothiazine 5,5-dioxide a) 10-Mesitylphenothiazine-3-carbaldehyde

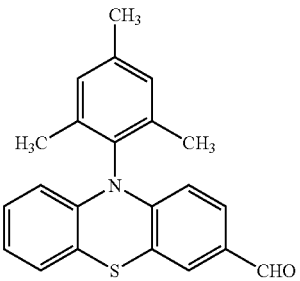

3.66 g (23.6 mmol) of 99% phosphorus oxychloride were added dropwise at 20° C. with stirring and ice cooling to a solution of 5.00 g (15.8 mmol) of 10-mesitylphenothiazine and 3.23 g (23.6 mmol) of 99% N-methylformanilide in 5 ml of o-dichlorobenzene within 15 min. After stirring at 20° C. for 30 min, the reaction solution was heated to 70° C. and kept at this temperature for 4 hours. The reaction solution was admixed with a solution of 16 g of sodium acetate in 35 ml of water within 5 min. After stirring at 70° C. for 1 hour, N-methylformanilide and o-dichlorobenzene were removed with a steam distillation. 250 ml of methylene chloride were added to the distillation bottoms. The organic phase was removed and filtered through silica gel. The filtrate was concentrated and dried at 40° C. under reduced pressure. 5.05 g (93% of theory) of analytically pure greenish powder having a melting point of 136-140° C. were obtained.

b) 10-Mesityl-5,5-dioxophenothiazine-3-carbaldehyde

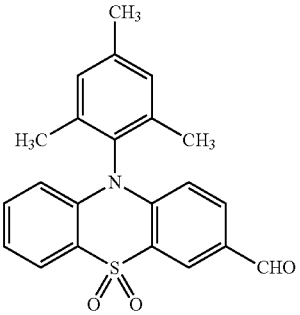

A solution of 4.00 g (11.6 mmol) of 10-mesitylphenothiazine-3-carbaldehyde in 150 ml of methylene chloride was admixed at room temperature with 6.28 g (25.5 mmol) of 70% m-chloroperbenzoic acid in portions and stirred at room temperature for 3 h. The solution was concentrated to dryness under reduced pressure. The residue was dissolved in 25 ml of a solvent mixture of 98 parts of methylene chloride and 2 parts of methanol, and purified by column chromatography on silica gel. The solution was concentrated to dryness and dried at 50° C. under reduced pressure. 2.75 g (63% of theory) of yellowish microcrystals were obtained, which melted at 194-197° C.

c) 10-Mesityl-3-(2-{4'-[2-(10-mesityl-5,5-dioxophenothiazin-3-yl)vinyl]biphenyl-4-yl}vinyl)phenothiazine 5,5-dioxide

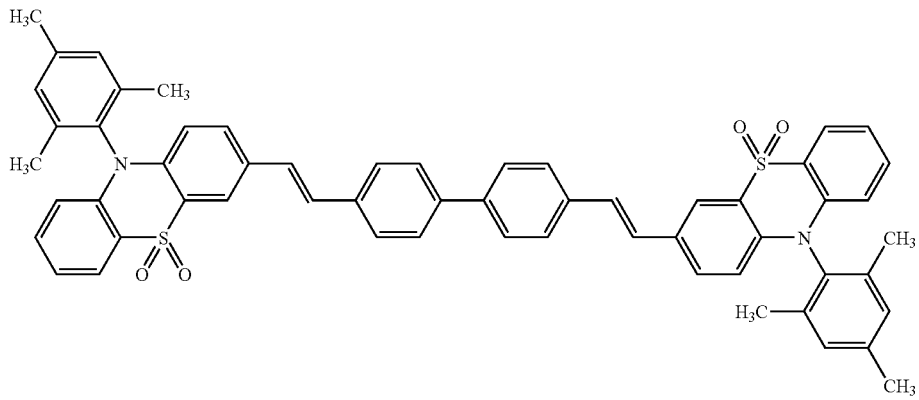

0.93 g (8.1 mmol) of potassium tert-butoxide and then 2.70 g (7.16 mmol) of 10-mesityl-5,5-dioxophenothiazine-3-carbaldehyde (example 35b) were added at room temperature with stirring under nitrogen to a solution of 1.63 g (3.58 mmol) of diethyl[4'-(diethoxyphosphorylmethyl)biphenyl-4-ylmethyl]phosphonate (U.S. Pat. No. 3,984,399, example 2, column 29, lines 58-66) in 40 ml of dimethyl sulfoxide which has been dried over a molecular sieve. After stirring at room temperature for 4 h, the reaction solution was diluted with 200 ml of methanol and stirred for a further 1 h. The precipitate was filtered off, washed with 100 ml of methanol, stirred up again in 300 ml of methanol, filtered again and dried at 35° C. under reduced pressure. The crude product (2.90 g) was recrystallized twice from dimethylformamide and once from chlorobenzene. The crystals were filtered off with suction, washed successively with chlorobenzene and ethanol, filtered off with suction and dried at 80° C. under reduced pressure. After the removal of solvent residues under high vacuum ($2 \times 10^{-5}$ mbar) at 250° C., 0.98 g (30% of theory) of analytically pure luminous yellow microcrystals having an m.p. of >350° C. were obtained, whose solution in chloroform fluoresced at $\lambda$=456, 485 (S), 522 (S) nm.

Example 38

10-(2-Thiophenyl)phenothiazine 5,5'-dioxide a) 10-(2-thiophenyl)phenothiazine

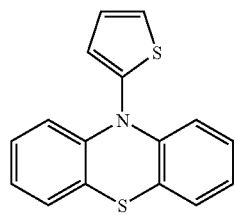

8.4 g (42 mmol) of phenothiazine, 9.1 g (42 mmol) of 98% 2-iodothiophene, 7.0 g (51 mmol) of potassium carbonate and 0.18 g (2.8 mmol) of copper powder were heated to 140° C. and stirred at this temperature for 7 hours. The reaction melt was cooled, admixed with 200 ml of ethanol, heated under reflux and hot-filtered. The residue was washed twice with ethanol. The ethanol solution was concentrated and, after column chromatography (eluent: 2:5 ethyl acetate/cyclohexane), 3.13 g of product of value were obtained, which were utilized immediately for the subsequent reaction step b).

b) 10-(2-Thiophenyl)phenothiazine 5,5'-dioxide

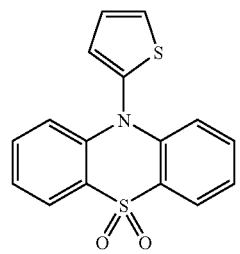

3.13 g (11.1 mmol) of 10-(2-thiophenyl)phenothiazine from reaction step a) were dissolved in 100 ml of methylene chloride. At 0-5° C., 5.52 g (22.4 mmol) of 77% m-chloroperbenzoic acid were added in portions. The reaction solution was stirred at room temperature for 2 hours. The reaction mixture was concentrated and the residue was dissolved in 250 ml of methylene chloride. The organic phase was washed three times with 20 ml each time of 10% potassium hydroxide solution and five times with 50 ml each time of demineralized water. After column chromatography (eluent: methylene chloride), the product of value was obtained, which was purified further by crystallization from acetic acid and subsequent sublimation. 0.34 g (10% of theory) of colorless microcrystals having a melting point of 230-234° C. were obtained.

Example 39

2,5-(1,4-Dimethoxyphenylene)-10,10'-bis(phenothiazine) 5,5'-dioxide a) 2,5-(1,4-Dimethoxyphenylene)-10,10'-bis(phenothiazine)

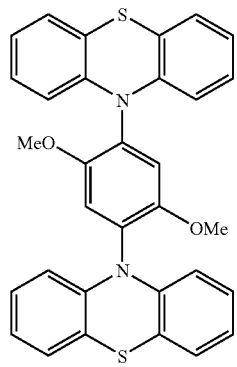

The preparation was effected according to K. Okada et al., J. Am. Chem. Soc. 1996, 118, 3047-3048.

0.8 g (4.0 mmol) of phenothiazine, 0.88 g (2.2 mmol) of 97% 1,4-diiodo-2,5-dimethoxybenzene, 0.66 g (4.8 mmol) of potassium carbonate and 0.016 g (0.25 mmol) of activated copper powder were heated to 140° C. in DMSO (10 ml) and stirred at this temperature for 15 hours. After the reaction mixture had been cooled to room temperature, 30 ml of methylene chloride were added and the suspension was filtered. The methylene chloride solution was washed three times with 25 ml each time of 0.1 molar hydrochloric acid, dried and concentrated. 0.99 g of the target compound was obtained as a colorless solid.

b) 2,5-(1,4-Dimethoxyphenylene)-10,10'-bis(phenothiazine) 5,5'-dioxide

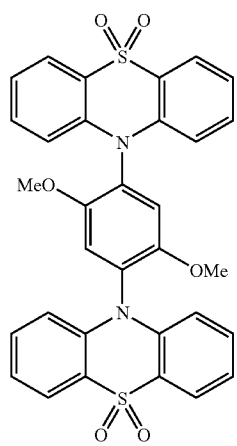

0.43 g (0.81 mmol) of 2,5-(1,4-dimethoxyphenylene)-10,10'-bis(phenothiazine) from reaction step a) was dissolved in 15 ml of methylene chloride. After stirring at room temperature for 1 hour, 0.56 g (3.2 mmol) of 77% m-chloroperbenzoic acid was added in portions. The reaction solution was stirred at room temperature for 24 hours, in the course of which a solid precipitated out. The suspension was concentrated and the residue in demineralized water was adjusted to pH 12 with 10 ml of 10% sodium hydroxide solution, stirred at 70° C. for 1 hour and then filtered. The residue was washed with hot water and dried at 80° C. under reduced pressure. 0.20 g (41%) of product of value was obtained.

Example 40

Production of an OLED

An OLED having the following layer structure was produced by vapor deposition of the individual layers: ITO/NPD (40 nm)/3,7-bis(2,2-diphenylvinyl)-10-methylphenothiazine 5,5-dioxide (Example 13) (40 nm)/BCP (6 nm)/LiF (1 nm)/aluminum.

NPD=4,4'-bis[N-(1-naphthyl)-N-phenylamino]biphenyl

BCP=2,9-dimethyl-4,7-diphenyl-1,10-phenanthroline

LiF=lithium fluoride

The OLED had a maximum photometric efficiency of 2.7 cd/A at a voltage of 4 V and a maximum illumination density of 5750 cd/m$^2$ at 9 V. The intensity maximum of the electroluminescence was at 455 nm.

Example 41

Production of an OLED (mPTO2 as a Hole and Exciton Blocker)

An OLED having the following layer structure was produced by vapor deposition of the individual layers: ITO/DPBIC (28 nm)/ester: CN-PMIC (33%) (20 nm) mPTO2 (example 5) (5 nm)/TPBI (40 nm)/LiF (0.7 nm)/aluminum.

DPBIC (whole conductor and exciton blocker) =

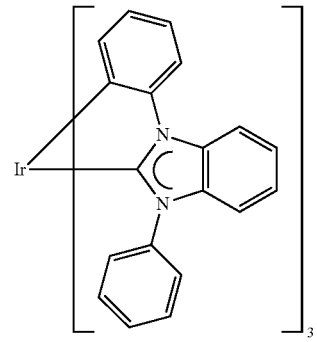

Ester (matrix for emitter) =

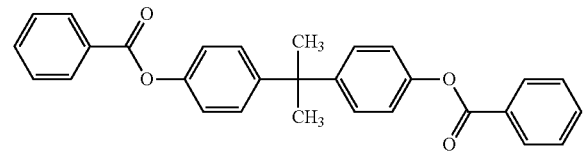

-continued

CN-PMIC (emitter) = 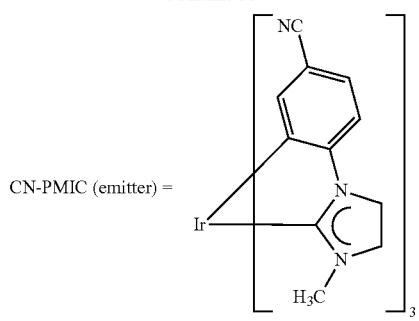

mPTO2 (hole and exciton blocker)=1,3-phenylene-10,10'-bis(phenothiazine 5,5-dioxide)

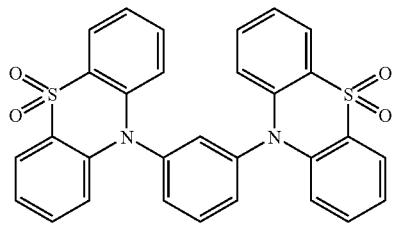

TPBI (electron conductor)=1,3,5-phenylene-2,2',2''-tris(1-phenylbenzimidazole)

LiF=lithium fluoride

The above-described OLED had the following electrooptical data:

| | |
|---|---|
| Emission maximum | 464 nm |
| CIE color coordinates (x, y) | 0.15; 0.15 |
| Maximum photometric efficiency | 15.1 cd/A |
| Photometric efficiency at 100 cd/m² (600 cd/m²) | 14.4 cd/A (12.1 cd/A) |
| Power efficiency | 11.1 lm/W |
| External quantum yield | 12.1% |
| Maximum luminance | 2000 cd/m² |

What is claimed is:

1. An organic light-emitting diode comprising as emitter substances or hole and exciton blockers compounds based on Formula I

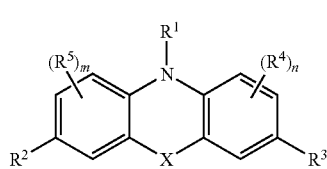
(I)

in which:

X is $SO_2$, SO;

$R^1$ is H, alkyl, aryl, heteroaryl;

or

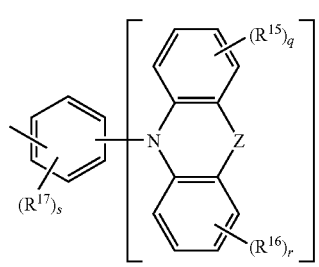
(IV)

or

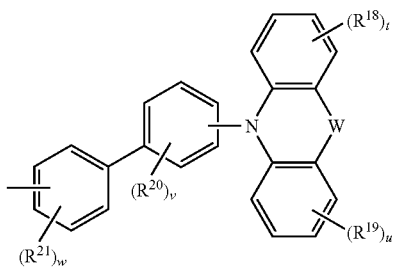
(V)

$R^2$, $R^3$ are each independently H, alkyl, aryl or $COR^{31}$, where $R^2$ and $R^3$ are not at the same time H, wherein aryl is selected from the group consisting of phenyl, naphthyl, indanyl, 1,2-dihydronaphthenyl, 1,4-dihydronaphthenyl, indenyl and 1,2,3,4-tetrahydronaphthyl, which may each be unsubstituted or substituted by one or more further radicals, with the proviso that when aryl is substituted phenyl, further radicals are selected from the group consisting of alkyl, alkoxy, and halogen, or at least one of the $R^2$ or $R^3$ radicals is a radical of formula II

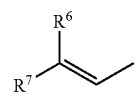
(II)

where the further $R^2$ or $R^3$ radical has the same definition or is H, alkyl, aryl, $NR^{22}R^{23}$; the further $R^2$ or $R^3$ radical is optionally likewise a radical of formula II, or one of the $R^2$ or $R^3$ radicals is a radical of formula III

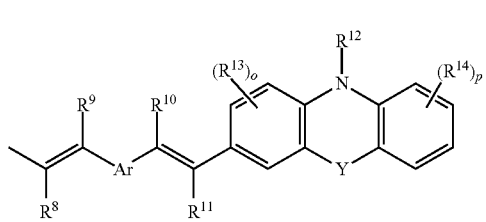
(III)

where the further $R^2$ or $R^3$ radical is H, alkyl, aryl, $NR^{22}R^{23}$;

$R^4$, $R^5$, $R^{13}$, $R^{14}$, $R^{15}$, $R^{16}$, $R^{18}$, $R^{19}$, $R^{20}$, $R^{21}$ are each independently alkyl, aryl, alkenyl, alkynyl or alkylaryl;

$R^{17}$ is halogen, alkoxy, alkyl, aryl, alkenyl, alkynyl or alkylaryl;

m, n are each 0, 1, 2 or 3;
o, p, q, r, s, t, u, v, w
  are each 0, 1, 2, 3 or 4;
z is 1 or 2;
$R^6$, $R^7$ are each independently H, alkyl, aryl, alkenyl, alkynyl, alkylaryl, alkoxy, aryloxy or $NR^{22}R^{23}$;
$R^8$, $R^9$, $R^{10}$, $R^{11}$
  are each independently H, alkyl, aryl, alkenyl, alkynyl or alkylaryl;
$R^{12}$ is H, alkyl or aryl;
$R^{22}$, $R^{23}$
  are each independently H, alkyl, aryl;
  or $R^{22}$ and $R^{23}$ together form a cyclic radical;
Y, Z, W are each S, $SO_2$; O, SO; and
Ar is arylene; and
$R^{31}$ is H, alkyl or aryl.

2. The organic light-emitting diode according to claim 1, wherein the emitter substance or the hole or exciton blocker of formula I is used, in which the symbols and radicals are each defined as follows:
  X is S or $SO_2$;
  $R^1$ is H, methyl, ethyl, unsubstituted phenyl or 4-alkoxyphenyl; or phenyl, 4-methoxyphenyl, thienyl or pyridyl substituted by one OH, OC(O)Ph, $OCH_2Ph$ or N-phenylbenzimidazolyl group, two F radicals, three $CH_3$ groups or

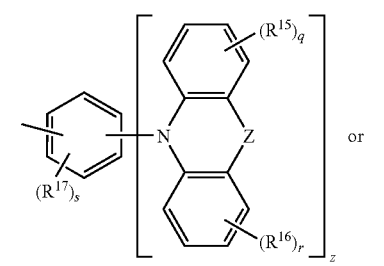

(IV)

or

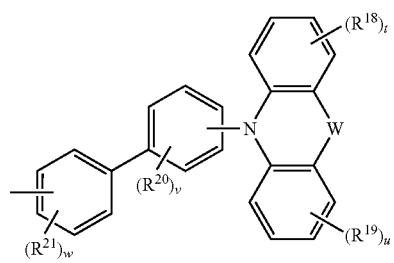

(V)

$R^2$, $R^3$ are each H, unsubstituted phenyl, 1-naphthyl, 2-naphthyl or CHO, where at least one of the $R^2$ or $R^3$ radicals is unsubstituted phenyl, 1-naphthyl or 2-naphthyl,
or
$R^2$ and $R^3$ are each

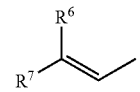

(II)

or $R^2$ is H and $R^3$ is

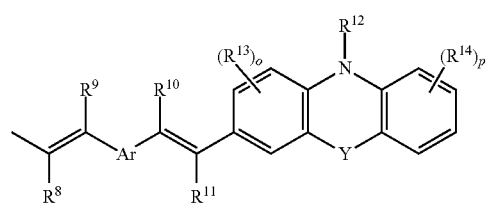

(III)

m, n, o, p, q, r, s, t, u, v and w
  are each 0, 1 or 2, preferably 0;
z is 1 or 2;
$R^6$, $R^7$ are each unsubstituted phenyl;
$R^8$, $R^9$, $R^{10}$, $R^{11}$
  are each H;
$R^{12}$ is H, methyl, ethyl, unsubstituted phenyl or 4-alkoxyphenyl or phenyl substituted by three $CH_3$ groups;
$R^{17}$ is alkyl, alkoxy, preferably methoxy;
$R^{22}$, $R^{23}$ are each aryl;
Y, Z, W are each S or $SO_2$; and
Ar is phenylene, naphthylene or biphenylene.

3. An organic light-emitting diode comprising as emitter substance a compound selected from the group consisting of compounds of formulae Ia, Ib, Ic, Id, Ie, If and Ig

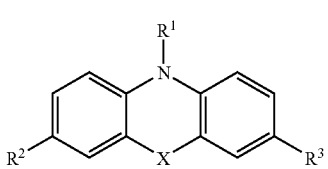

(Ia)

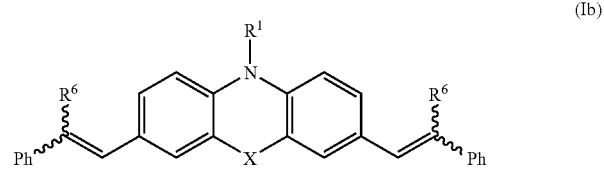

(Ib)

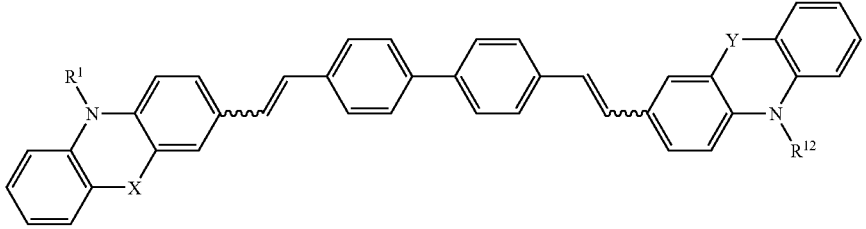

(Ic)

(Id)
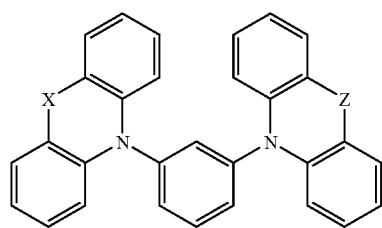

(Ie)
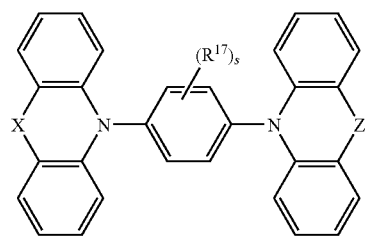

(If)
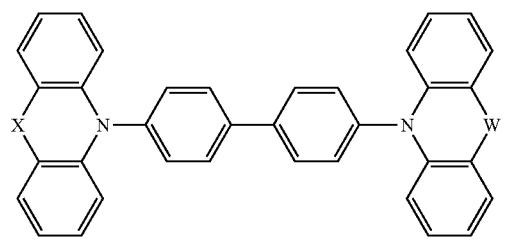

(Ig)
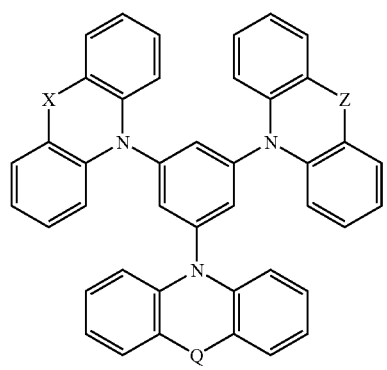

in which:
X, Y, Z, W, Q
  are each independently S or $SO_2$; and
$R^1$, $R^{12}$ are each H, methyl, ethyl or unsubstituted phenyl;
$R^2$, $R^3$ are each H or unsubstituted phenyl, where at least $R^2$ or $R^3$ is unsubstituted phenyl;
$R^6$ is methyl or unsubstituted phenyl;
$R^{17}$ is methoxy;
s is 0 or 2, where the substituents, in the case that s=2, are optionally arranged in the 2- and the 5-position; and
Ph is unsubstituted phenyl.

4. An organic light-emitting diode comprising as emitter substance a compound selected from the group consisting of compounds of formulae Ih and Ii;

in which
X, Y are each independently S or $SO_2$;
$R^1$ is phenyl, 4-methoxyphenyl, thienyl or pyridyl substituted by one OH, OC(O)Ph, $OCH_2Ph$ or N-phenylbenzimidazolyl group, three $CH_3$ groups or two F radicals;
$R^2$ is H;
$R^3$ is H or CHO; and
$R^{12}$ is phenyl substituted by three $CH_3$ groups.

5. An organic light-emitting diode comprising a hole or exciton blocker selected from the group consisting of compounds of the formulae Ia, Id, Ie, Ig and Ih (Ih)
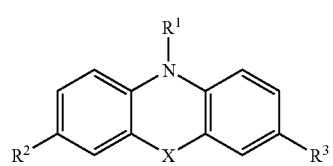

(Ii)
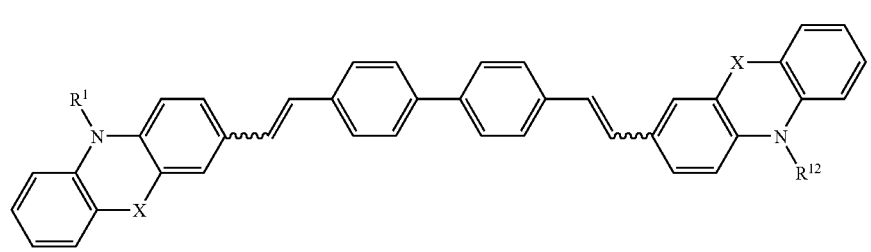

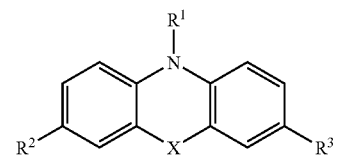
(Ia)

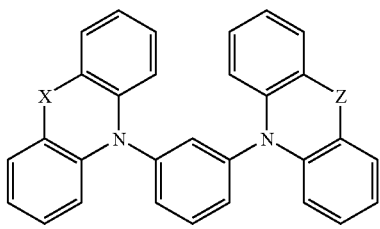
(Id)

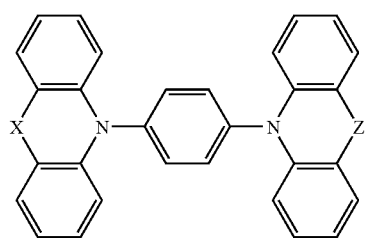
(Ie)

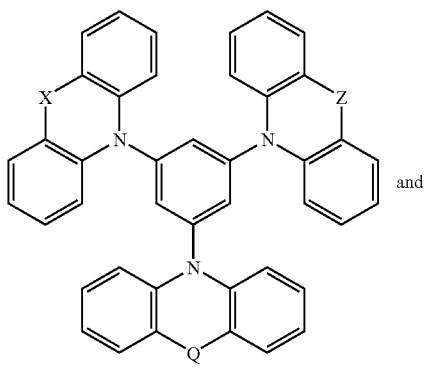
(Ig)

and

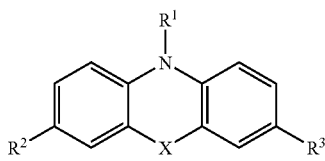
(Ih)

-continued in which:

X, Z, Q are each independently S or SO$_2$; and

R$^1$ is H, methyl, ethyl or unsubstituted phenyl, or phenyl, 4-methoxyphenyl, thienyl or pyridyl substituted by one OH, OC(O)Ph, OCH$_2$Ph or N-phenylbenzimidazolyl group, three CH$_3$ groups or two F radicals;

R$^2$, R$^3$ are each H or unsubstituted phenyl, where at least R$^2$ or R$^3$ is unsubstituted phenyl, or, in the case that R$^1$ is phenyl, 4-methoxyphenyl, thienyl or pyridyl substituted by one OH, OC(O)Ph, OCH$_2$Ph or N-phenylbenzimidazolyl group, three CH$_3$ groups or two F radicals, R$^2$ is H; and R$^3$ is H or CHO; preferably H.

6. An organic light-emitting diode comprising a light-emitting layer, wherein the light-emitting layer comprises at least one emitter substance of the formula I according to claim 1.

7. A light-emitting layer comprising at least one emitter substance of the formula I according to claim 1.

8. A light-emitting layer consisting of one or more emitter substances of the formula I according to claim 1.

9. An organic light-emitting diode comprising a light-emitting layer according to claim 7.

10. An organic light-emitting diode comprising a blocking layer for holes and excitons, wherein the blocking layer for holes and excitons comprises at least one compound of the formula I according to claim 1.

11. A device selected from the group consisting of stationary visual display units of computers and televisions, visual display units in printers, kitchen appliances and advertising panels, illuminations, information panels and mobile visual display units in mobile telephones, laptops, digital cameras, vehicles and destination displays on buses and trains, comprising an organic light-emitting diode according to claim 6.

12. A phenothiazine S,S-dioxide derivative selected from the group consisting of compounds of formulae XIV, XVI, XVII, XVIII, XIX, XX and XXII

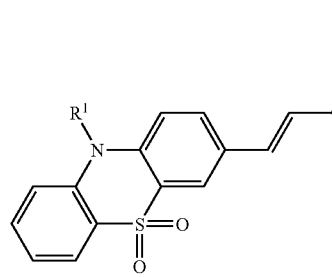
(XIV)

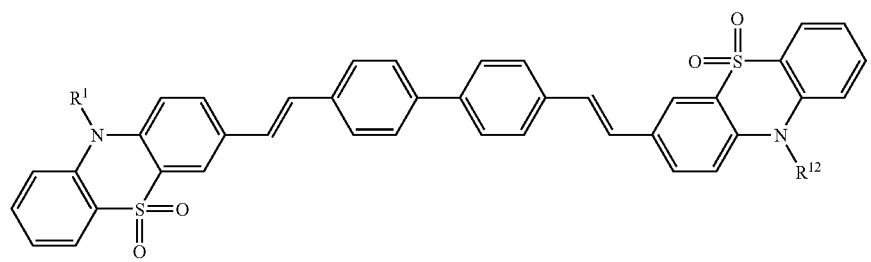
(XVI)

(XVII)
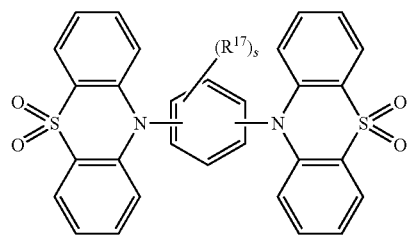

(XVIII)
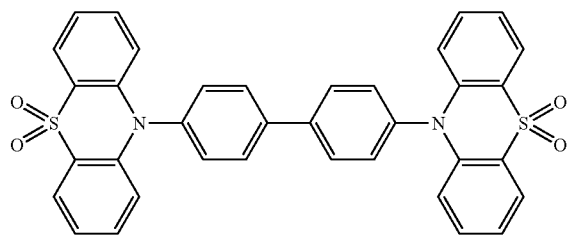

(XIX)
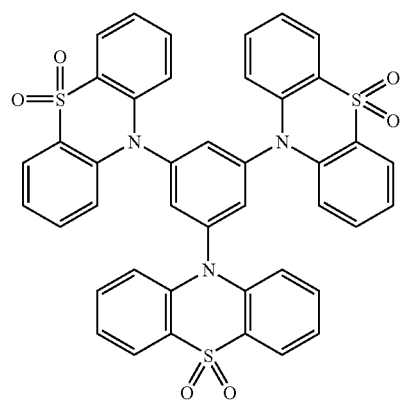

(XX)
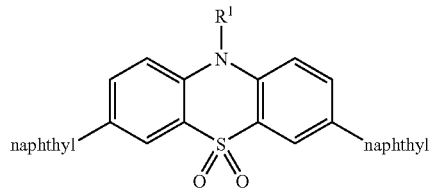

(XXII)
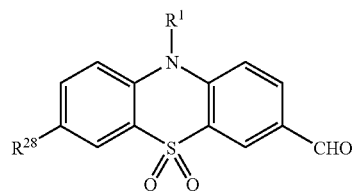

in which:
$R^1$, $R^{12}$ are each H, Me, Et or unsubstituted phenyl;
$R^6$ is Me or unsubstituted phenyl;
$R^{17}$ is methoxy;
s is 0 or 2, where the substituents, in the case that s=2, are optionally arranged in the 2- and the 5-position;
Ph is unsubstituted phenyl;
naphthyl is 1- or 2-naphthyl; and
$R^{28}$ is H or —CHO.

13. A phenothiazine derivative selected from the group consisting of compounds of formulae XXIII, XXV, XXVI, XXVII and XXIX (XXIII)
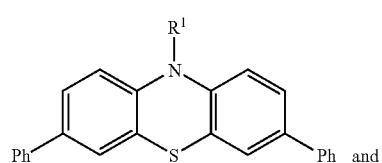
and (XXV)
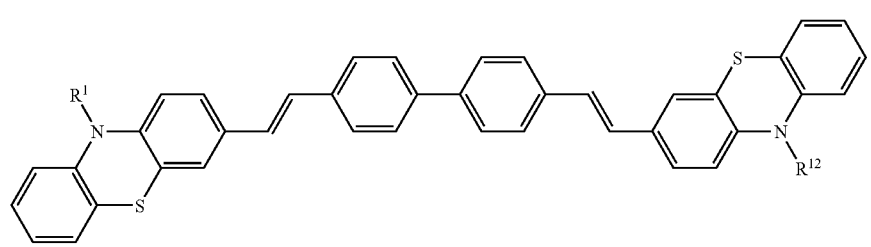

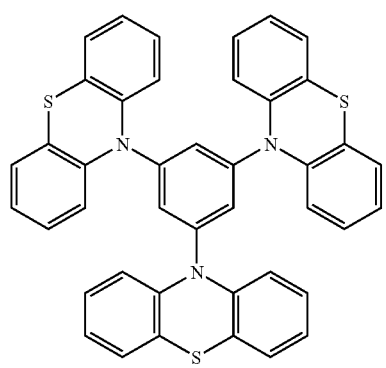

(XXVI)

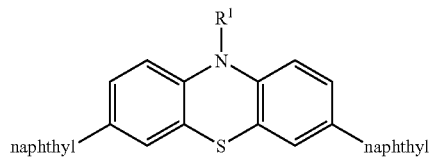

(XXVII)

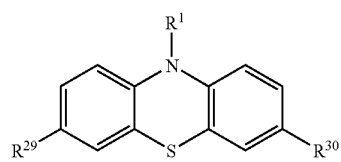

in which:
R¹, R¹² are each H, Me, Et or unsubstituted phenyl;
Ph is unsubstituted phenyl;
naphthyl is 1- or 2-naphthyl; and
R²⁹, R³⁰ are each —CHO or

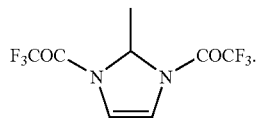

14. A phenothiazine S-oxide derivative of formula XXX

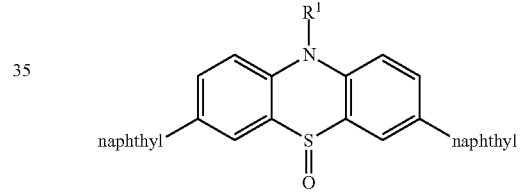

(XXX)

in which:
R¹ is H, Me, Et or unsubstituted phenyl; and
naphthyl is 1- or 2-naphthyl.

15. A phenothiazine S,S-dioxide derivative selected from the group consisting of compounds of formulae XXXI and XXXII (XXXI)

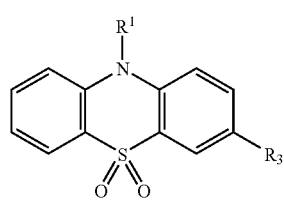

(XXXII)

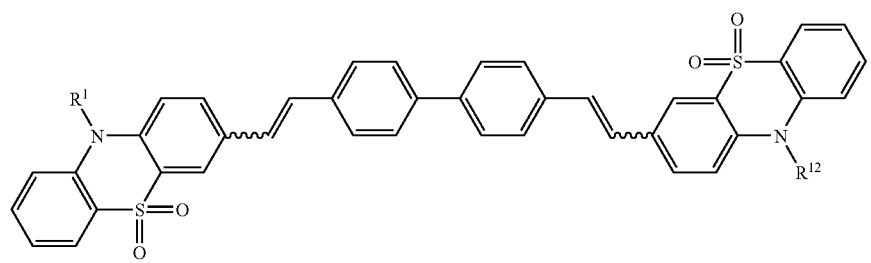

in which
R¹ is phenyl, 4-methoxyphenyl, 2-thienyl or pyridyl substituted by one OH, OC(O)Ph, OCH₂Ph or N-phenylbenzimidazolyl group, three CH₃ groups or two F radicals,
R³ is CHO, and
R¹² is a phenyl substituted by three CH₃ groups.

16. A phenothiazine derivative of formula XXXIII

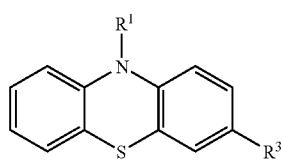

XXXIII in which
R¹ is phenyl or pyridyl substituted by one OH, OC(O)Ph, OCH₂Ph or N-phenylbenzimidazolyl group, three CH₃ groups or two F radicals, and
R³ is CHO.

17. An OLED comprising at least one phenothiazine S,S-dioxide derivative according to claim 12.

18. A light-emitting layer comprising at least one phenothiazine S,S-dioxide derivative according to claim 12.

19. An OLED comprising a light-emitting layer according to claim 18.

20. A hole- and exciton-blocking layer comprising at least one phenothiazine S,S-dioxide derivative of formulae XIV, XVII, XIX, or XXII according to claim 12.

21. An OLED comprising a hole- and exciton-blocking layer according to claim 20.

22. A device selected from the group consisting of stationary visual display units of computers and televisions, visual display units in printers, kitchen appliances and advertising panels, illuminations, information panels and mobile visual display units in mobile telephones, laptops, digital cameras, vehicles and destination displays on buses and trains, comprising an organic light-emitting diode according to claim 10.

23. An OLED comprising at least one phenothiazine S,S-dioxide derivative according to claim 15.

24. A light-emitting layer comprising at least one phenothiazine S,S-dioxide derivative according to claim 15.

25. A hole- and exciton-blocking layer comprising at least one phenothiazine S,S-dioxide derivative of formulae XXXI, or XXXIII according to claim 15.

26. An OLED comprising at least one phenothiazine derivative according to claim 13.

27. A light-emitting layer comprising at least one phenothiazine derivative according to claim 13.

28. A hole- and exciton-blocking layer comprising at least one phenothiazine derivative of formulae XXIII, XXVI, XXXVIIII, or XXIX according to claim 13.

29. An OLED comprising at least one phenothiazine derivative according to claim 16.

30. A light-emitting layer comprising at least one phenothiazine derivative according to claim 16.

31. A hole- and exciton-blocking layer comprising at least one phenothiazine derivative of formula XXXIII according to claim 16.

32. An OLED comprising at least one phenothiazine S-oxide derivative according to claim 14.

33. A light-emitting layer comprising at least one phenothiazine S-oxide derivative according to claim 14.

34. An organic light-emitting diode comprising as emitter substances or hole and exciton blockers compounds of formula I

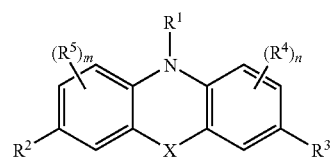

(I)

in which:
X is S or O;
R¹ is H, alkyl, aryl, heteroaryl;
or

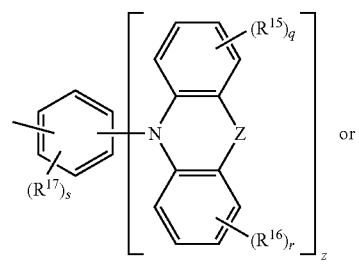

(IV)

or

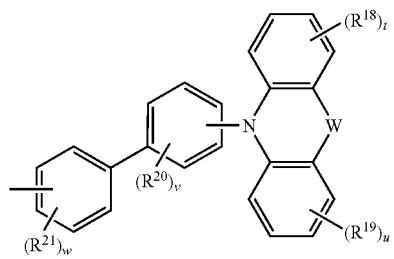

(V)

R²,
R³ are each independently H, alkyl, unsubstituted phenyl, 1-naphthyl, 2-naphthyl, or COR³¹, where R² and R³ are not at the same time H,
or
at least one of the R² or R³ radicals is a radical of formula II

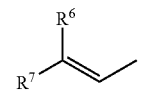

(II)

where the further R² or R³ radical has the same definition or is H, alkyl, aryl, NR²²R²³; the further R² or R³ radical is optionally likewise a radical of formula II,
or
one of the R² or R³ radicals is a radical of formula III

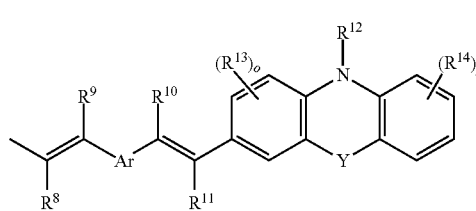

(III)

where the further $R^2$ or $R^3$ radical is H, alkyl, aryl, $NR^{22}R^{23}$;

$R^4$, $R^5$, $R^{13}$, $R^{14}$, $R^{15}$, $R^{16}$, $R^{18}$, $R^{19}$, $R^{20}$, $R^{21}$
  are each independently alkyl, aryl, alkenyl, alkynyl or alkylaryl;

$R^{17}$ is halogen, alkoxy, alkyl, aryl, alkenyl, alkynyl or alkylaryl;

m, n are each 0, 1, 2 or 3;

o, p, q, r, s, t, u, v, w
  are each 0, 1, 2, 3 or 4;

z is 1 or 2;

$R^6$, $R^7$ are each independently H, alkyl, aryl, alkenyl, alkynyl, alkylaryl, alkoxy, aryloxy or $NR^{22}R^{23}$;

$R^8$, $R^9$, $R^{10}$, $R^{11}$
  are each independently H, alkyl, aryl, alkenyl, alkynyl or alkylaryl;

$R^{12}$ is H, alkyl or aryl;

$R^{22}$, $R^{23}$
  are each independently H, alkyl, aryl;
  or $R^{22}$ and $R^{23}$ together form a cyclic radical;

Y, Z, W are each S, $SO_2$; O, SO; and

Ar is arylene; and $R^{31}$ is H, alkyl or aryl.

* * * * *